(12) United States Patent
Nahmias

(10) Patent No.: US 11,913,031 B2
(45) Date of Patent: Feb. 27, 2024

(54) METHOD TO REPRODUCE CIRCADIAN RHYTHMS ON A MICROFLUIDIC CHIP

(71) Applicant: Yissum Research Development Company of the Hebrew University of Jerusalem Ltd., Jerusalem (IL)

(72) Inventor: Yaakov Nahmias, Mevaseret Zion (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 536 days.

(21) Appl. No.: 16/905,987

(22) Filed: Jun. 19, 2020

(65) Prior Publication Data
US 2020/0318077 A1 Oct. 8, 2020

Related U.S. Application Data

(63) Continuation of application No. PCT/IL2018/051404, filed on Dec. 27, 2018.

(60) Provisional application No. 62/611,034, filed on Dec. 28, 2017.

(51) Int. Cl.
| | |
|---|---|
| C12N 5/071 | (2010.01) |
| C12M 3/06 | (2006.01) |
| C12M 1/34 | (2006.01) |
| C12N 5/0797 | (2010.01) |

(52) U.S. Cl.
CPC .......... *C12N 5/0697* (2013.01); *C12M 23/16* (2013.01); *C12M 41/12* (2013.01); *C12M 41/44* (2013.01); *C12N 5/067* (2013.01); *C12N 5/069* (2013.01); *C12N 5/0623* (2013.01); *C12N 5/0686* (2013.01); *C12N 2500/30* (2013.01); *C12N 2500/32* (2013.01); *C12N 2501/30* (2013.01); *C12N 2501/305* (2013.01)

(58) Field of Classification Search
CPC .. C12N 5/0697; C12N 5/067; C12N 2500/30; C12N 2501/30; C12N 2501/305; C12M 41/44; G01N 33/743
See application file for complete search history.

(56) References Cited

U.S. PATENT DOCUMENTS

2017/0081625 A1* 3/2017 Wikswo .............. F04B 43/0045

FOREIGN PATENT DOCUMENTS

| EP | 3190172 | 7/2017 |
| WO | WO 2019/130313 | 7/2019 |

OTHER PUBLICATIONS

Liu et al. Hepatocyte Cocultures with Endothelial Cells and Fibroblasts on Micropatterned Fibrous Mats to Promote Liver-Specific Functions and Capillary Formation Capabilities. Biomacromolecules 2014, 15, 1044-1054 (Year: 2014).*
International Preliminary Report on Patentability dated Jul. 9, 2020 From the International Bureau of WIPO Re. Application No. PCT/IL2018/051404. (9 Pages).
International Search Report and the Written Opinion dated Mar. 8, 2019 From the International Searching Authority Re. Application No. PCT/IL2018/051404. (17 Pages).
Adamovich et al. "Circadian Clocks and Feeding Time Regulate the Oscillations and Levels of Hepatic Triglycerides", Cell Metabolism, 19(2): 319-330, Feb. 4, 2014.
Bavli et al. "Real-Time Monitoring of Metabolic Function in Liver-O-Chip Microdevices Tracks the Dynamics of Mitochondrial Dysfunction", PNAS 113(16): E2231-E2240, Apr. 4, 2016.
Bavli et al. "Real-Time Monitoring of Metabolic Function in Liver-on-Chip Microdevices Tracks the Dynamics of Mitochondrial Dysfunction", Proc. Natl. Acad. Sci. USA, PNAS, XP055375339, 113(16): E2231-E2240, Published Online Apr. 4, 2016.
Benattar "Rosetrees Trust Interdisciplinary Prize Awarded to Hebrew University Scientists", 2 Pages, Downloaded from Internet, Sep. 19, 2017.
Cyr et al. "Circadian Hormone Control in a Human-On-A-Chip: In Vitro Bbiology's Ignored Component?", Experimental Biology and Medicine, 242: 1714-1731, Oct. 25, 2017.
Deng et al. "Synchronizing Stochastic Circadian Oscillators in Single Cells of Neurospora Crassa", Scientific Reports, 6(35828): 1-18, Oct. 27, 2016.
Ehrlich et al. "Microphysiological flux balance platform unravels the dynamics of drug induced steatosis", Lab on a Chip, 18(17): 2510-2522, Jul. 2, 2018.
Gagliano "Development of A 'Lap-on-Chip' Platform for Studying the Control of the Circadian Clock by Metabolic Cycles", PhD Thesis, Universita Degli Studi di Padova, Dipartimento di Ingegneria Industriale, Scuola di Dottorato di Ricerca in Ingegneria Industriale, Indirizzo Ingegneria Chimica, dei Materiali e della Produzione, Ciclo XXVII, p. 1-187, Jan. 1, 2018.
Kanda et al. "A Microfluidic Platform to Generate Robust Gas-Liquid Interface for Organotypic Slice Culture Over a Long Period", 17th International Conference on Miniaturized Systems for Chemistry and Life Sciences, Freiburg, Germany, Oct. 27-31, 2013, p. 1063-1065, Oct. 27, 2013.

(Continued)

*Primary Examiner* — Taeyoon Kim
(74) *Attorney, Agent, or Firm* — The Roy Gross Law Firm, LLC; Roy Gross

(57) ABSTRACT

Provided are in-vitro methods and devices for sustaining a synchronized circadian rhythm in cells of a cell culture by exposing the cells to a continuous flow of medium and to at least two stimuli provided in an oscillating manner with a periodicity of 24±4 hours, wherein a first stimulus and a second stimulus of said at least two stimuli are distinct, wherein said first stimulus is provided in a first time period and reaches a first peak in a first peak time period, and wherein a second stimulus is provided in a second time period and reaches a second peak in a second peak time period, and wherein an interval between end of time period of said first peak and beginning of said time period of said second peak is at least about 2 hours.

23 Claims, 27 Drawing Sheets
(26 of 27 Drawing Sheet(s) Filed in Color)
Specification includes a Sequence Listing.

(56) References Cited

OTHER PUBLICATIONS

Prill et al. "Real-Time Monitoring of Oxygen Uptake in Hepatic Bioreactor Shows CYP450-Independent Mitochondrial Toxicity of Acetaminophen and Amiodarone", Archives of Toxicology, XP035866592, 90(5): 1181-1190, Published Online Jun. 5, 2015.
Yamada et al. "A Simple Process for Long-Term Culture of Adherent Mammalian Cells in Micro-Flow Chamber Based on PDMS and Polystyrene", Proceedings of the 2011 International Conference on Microtechnologies in Medicine and Biology, Lucerne, Switzerland, May 4-6, 2011, W2P.5: 10-11, May 4, 2011.
Communication Pursuant to Article 94(3) EPC dated May 30, 2022 From the European Patent Office Re. Application No. 18836534.0. (8 Pages).
Communication Pursuant to Article 94(3) EPC dated Jul. 6, 2021 From the European Patent Office Re. Application No. 18836534.0. (.

\* cited by examiner

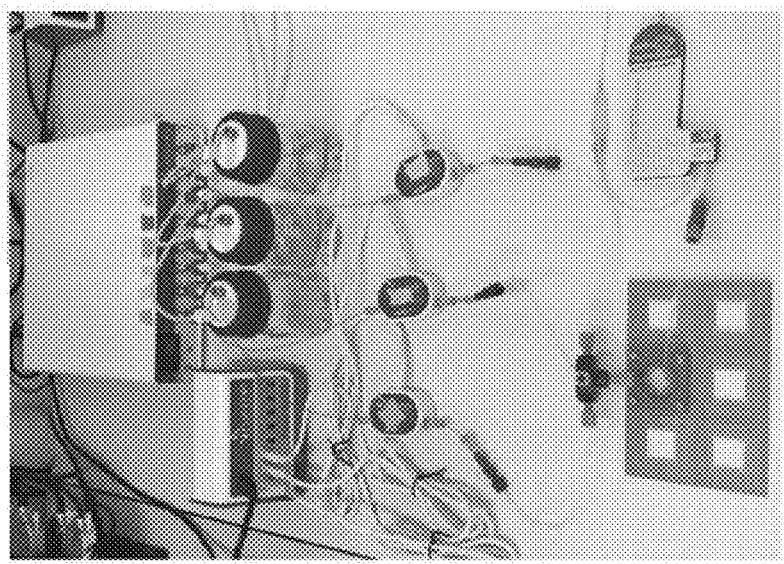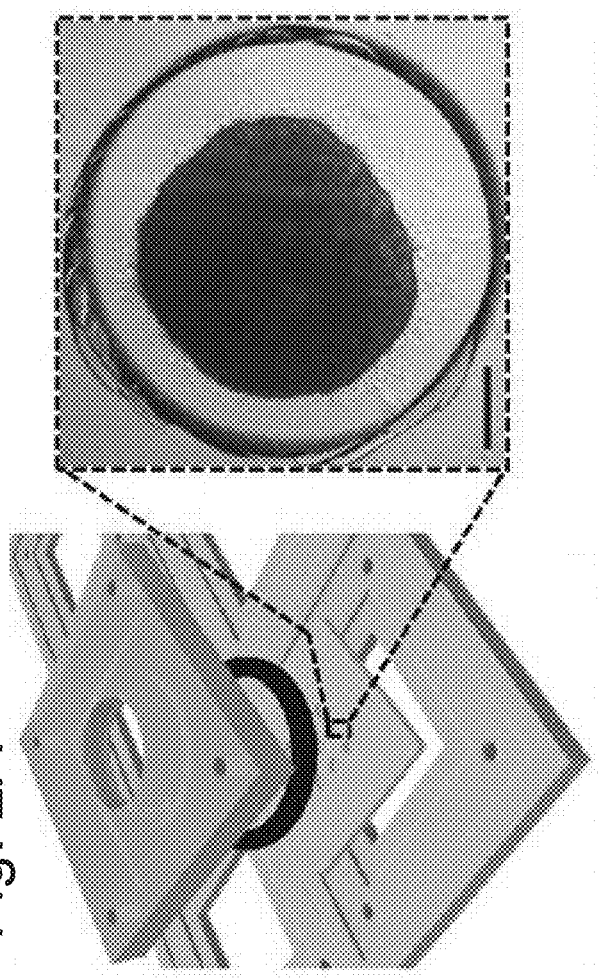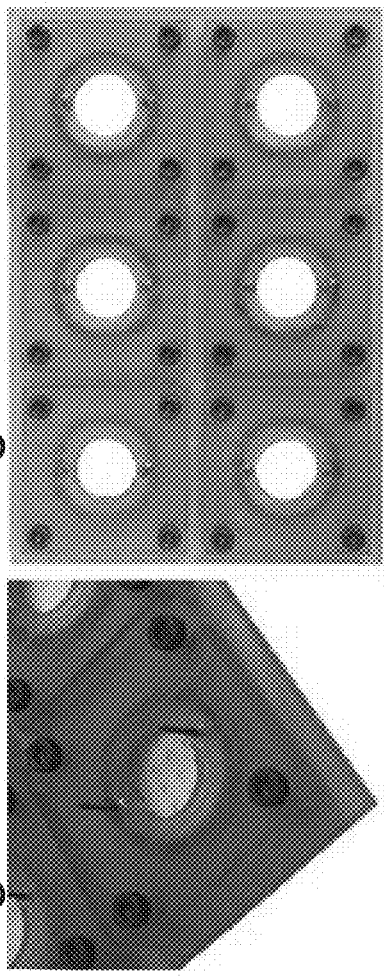

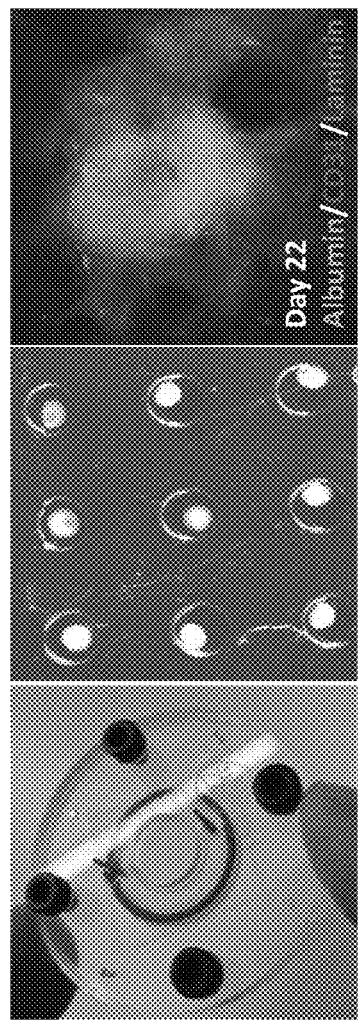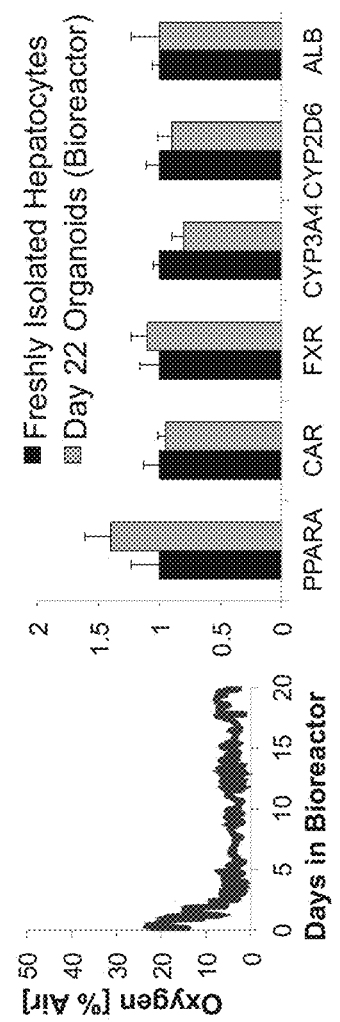

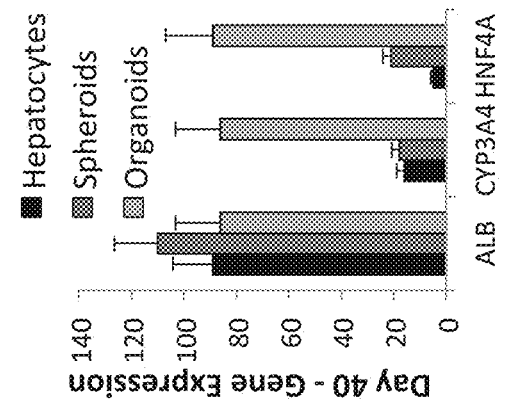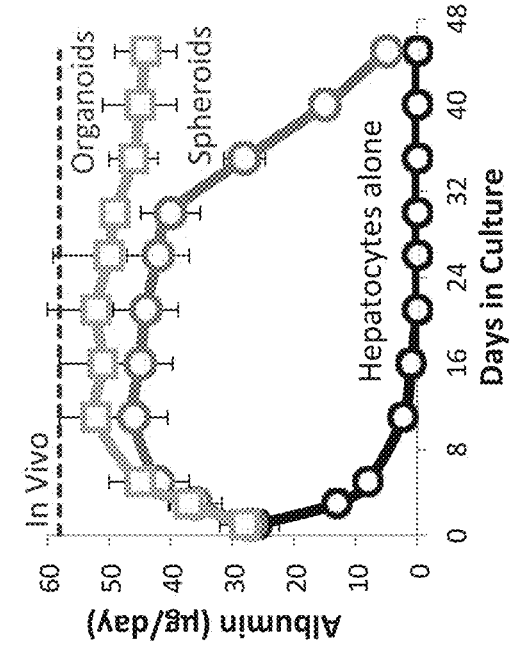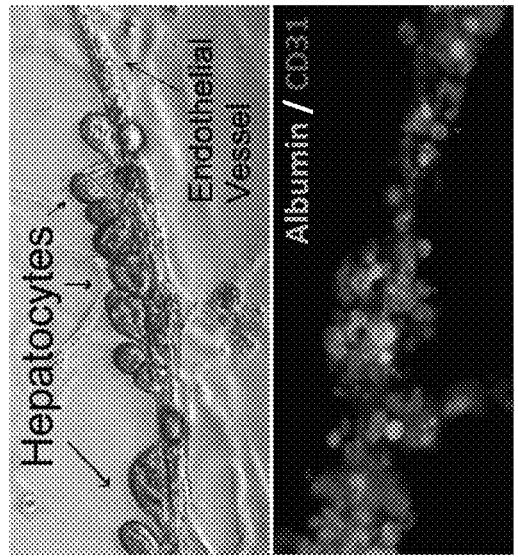

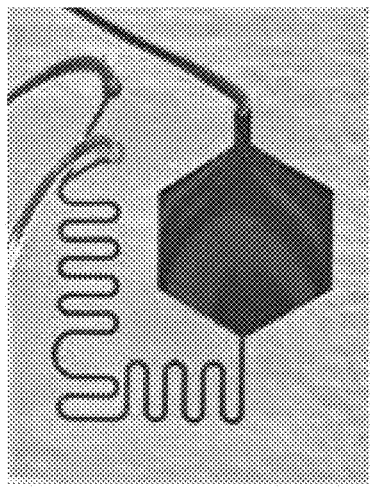
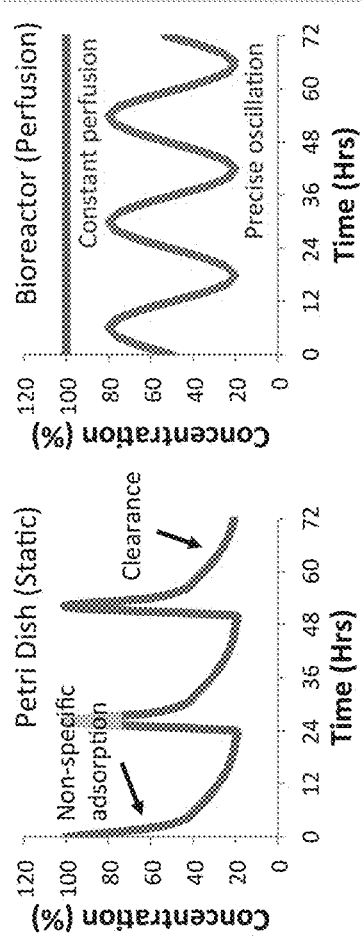
Fig. 9A  Fig. 9B  Fig. 9C

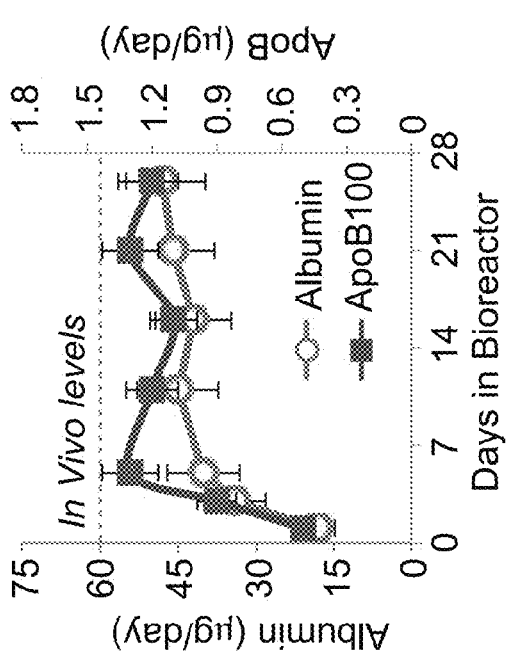
Fig. 10A
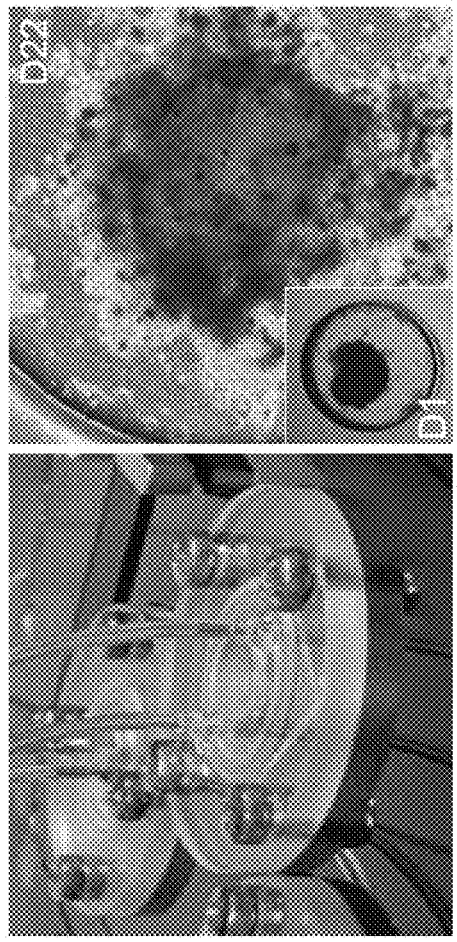
Fig. 10B
Fig. 10C
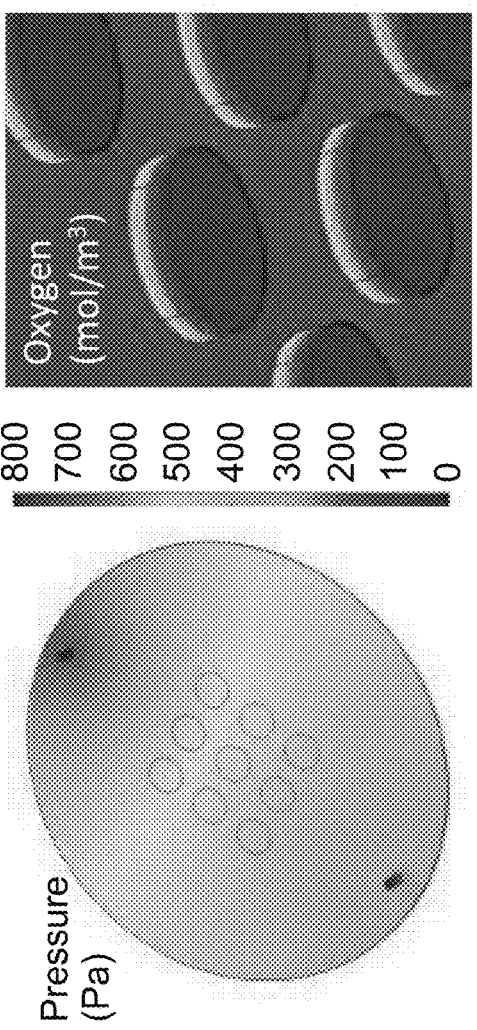
Fig. 10D
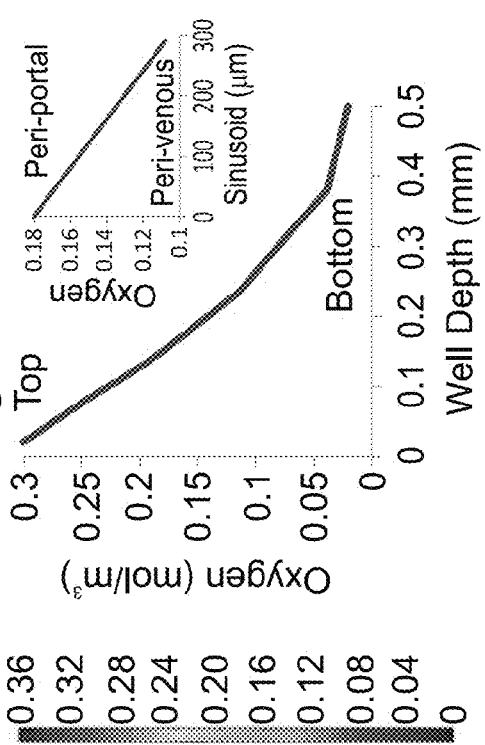
Fig. 10E

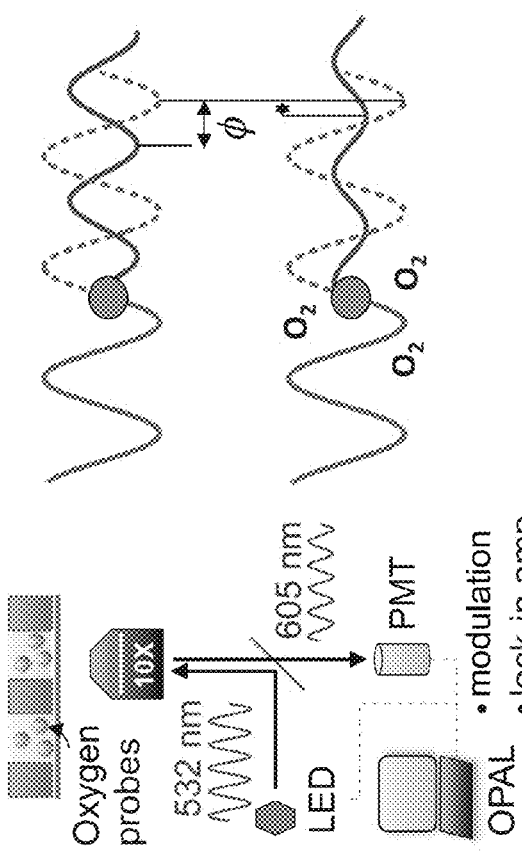
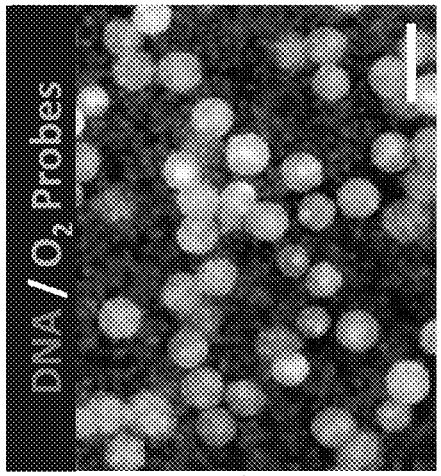
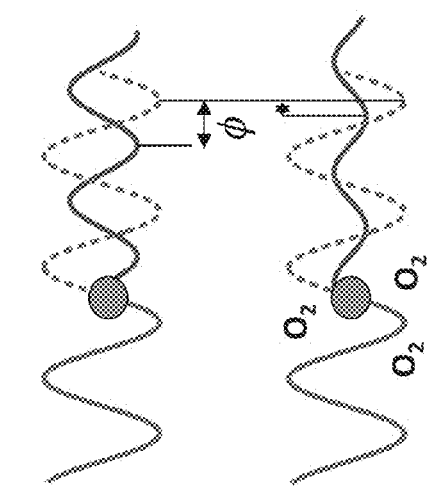
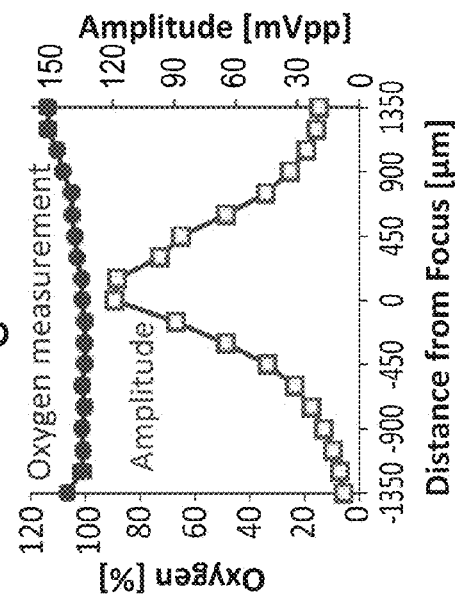
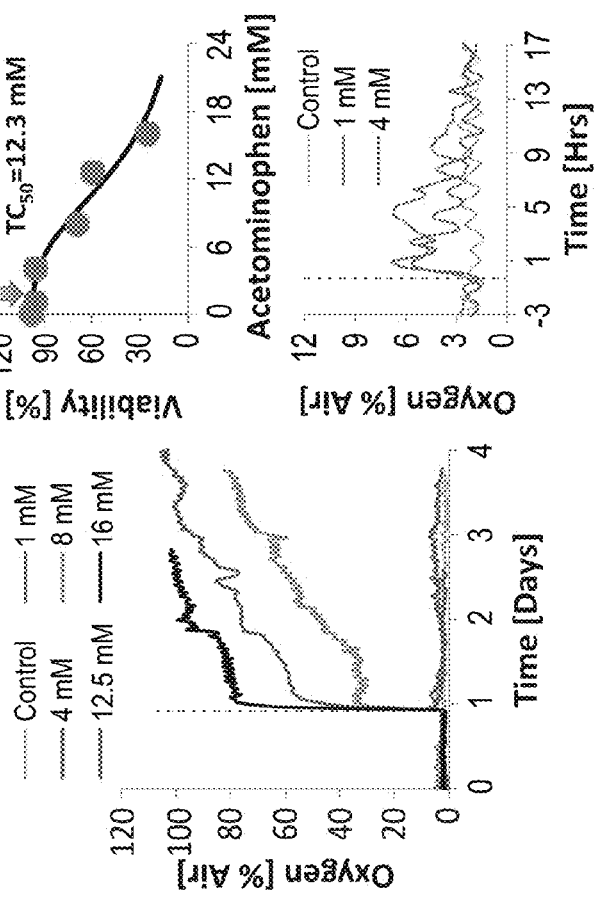

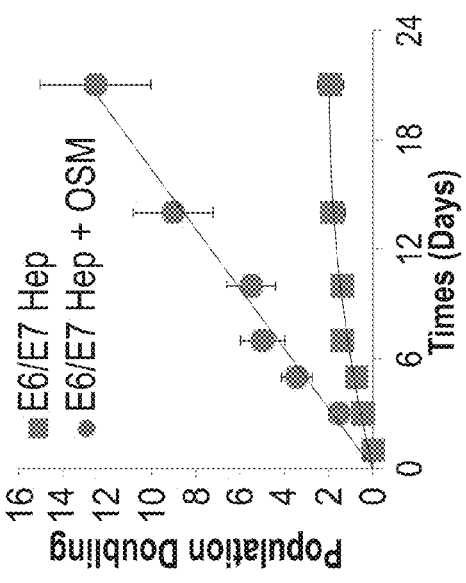
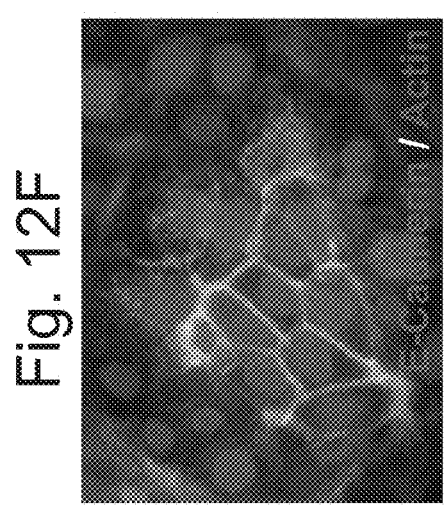
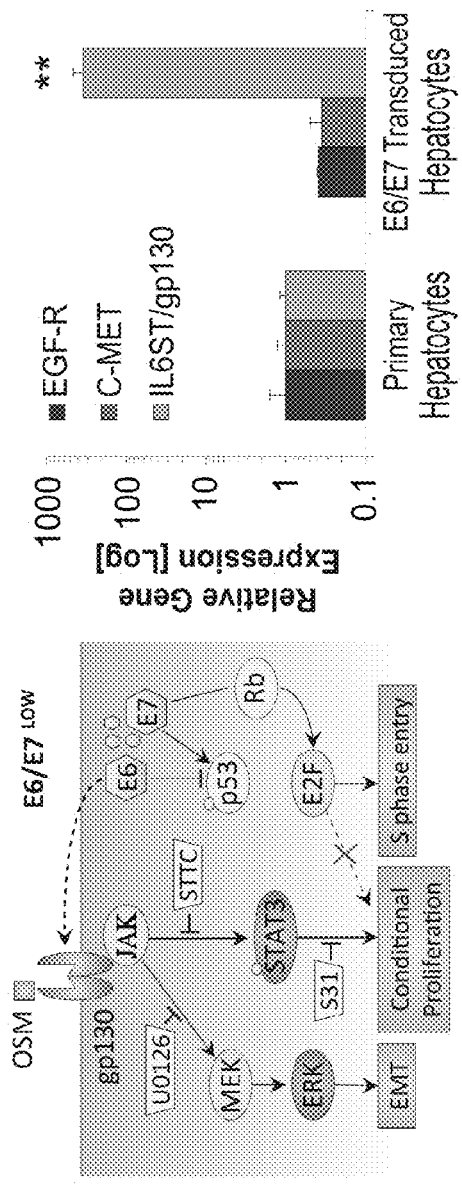
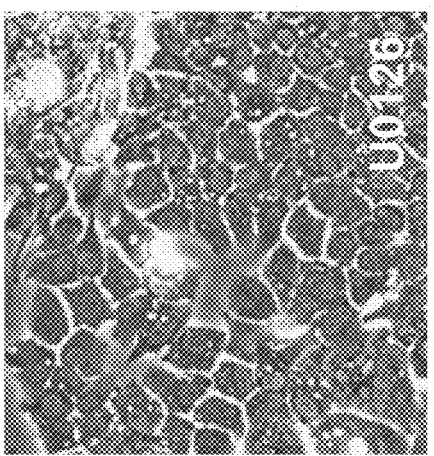
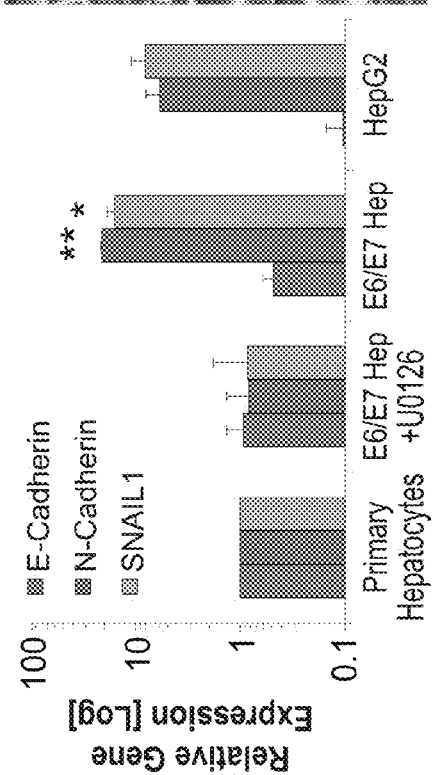

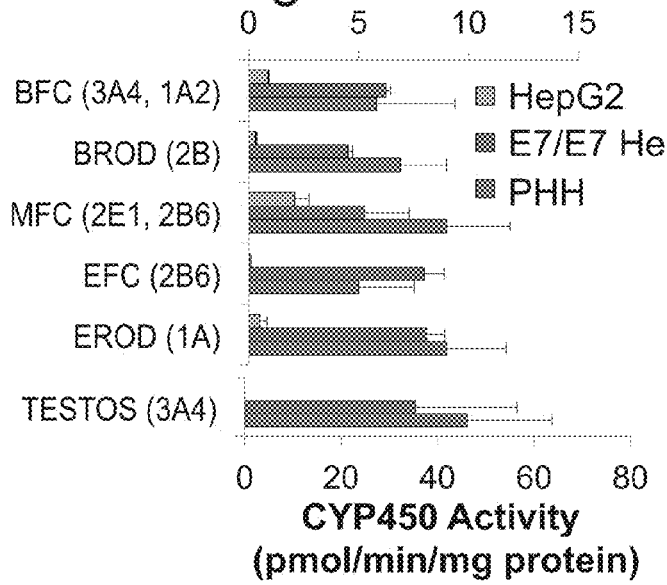
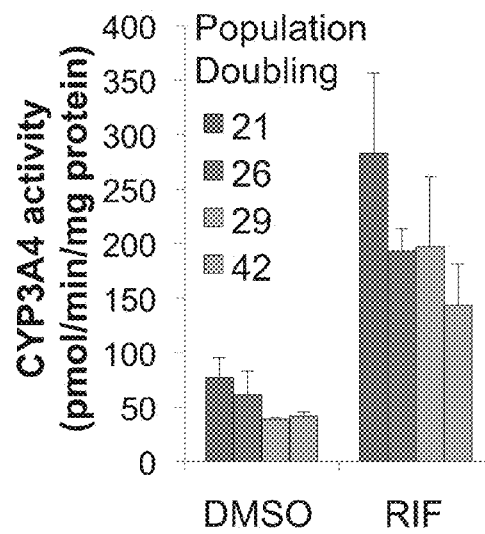
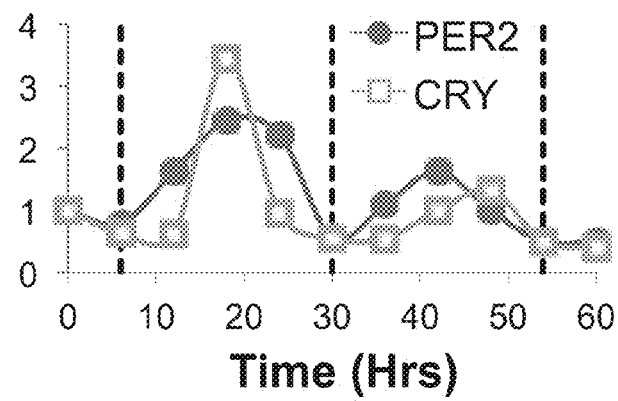
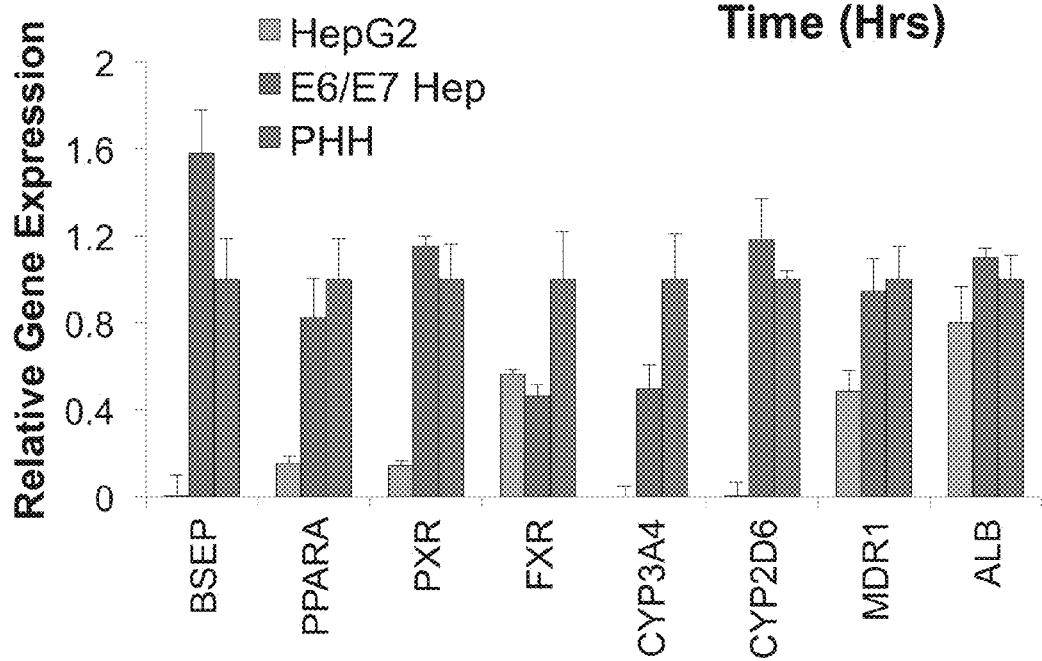

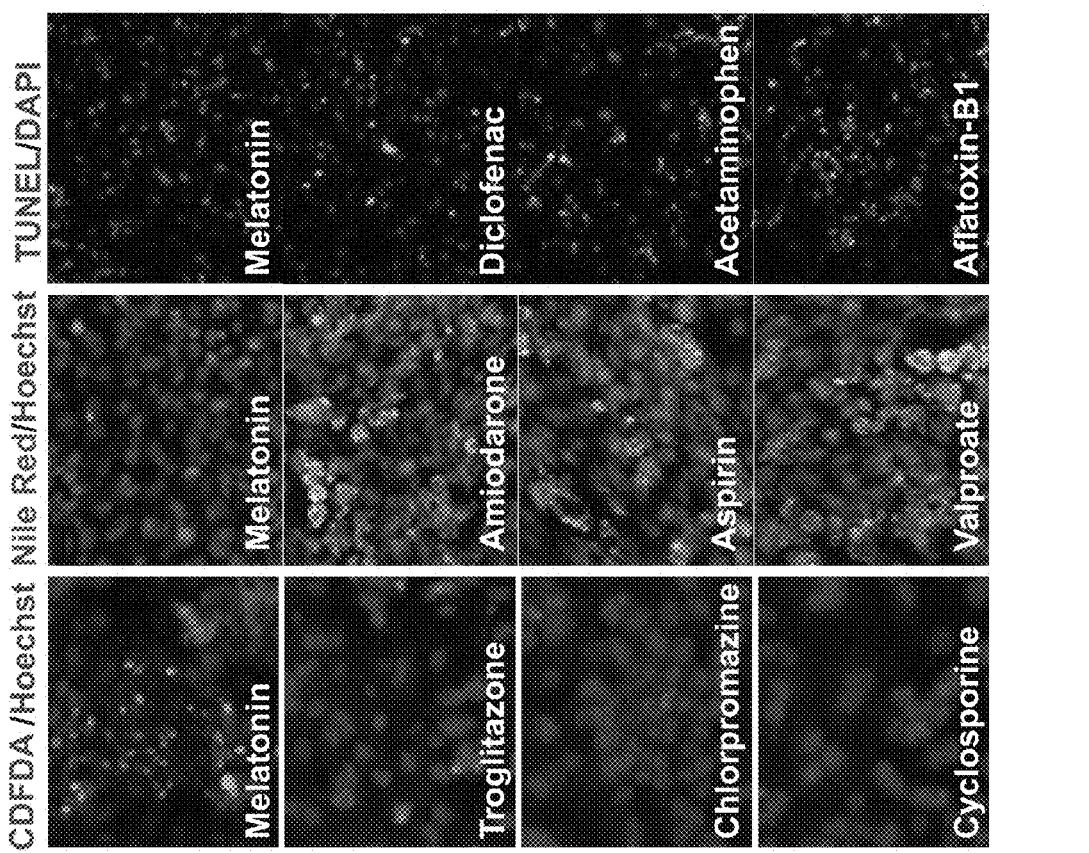
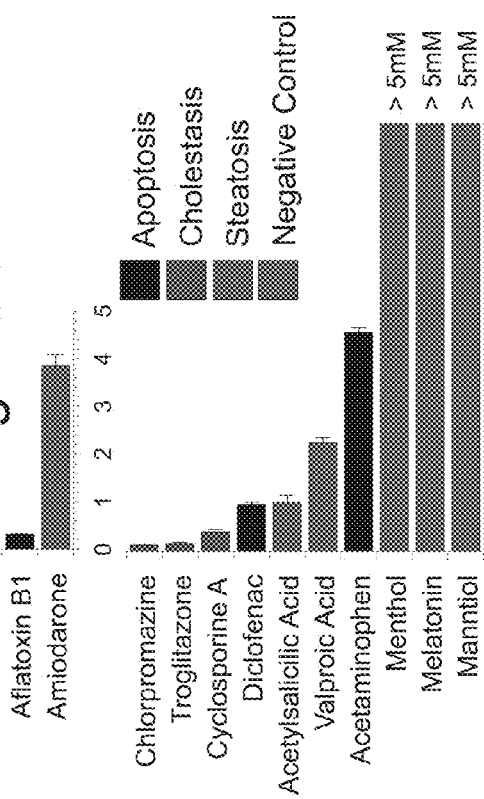
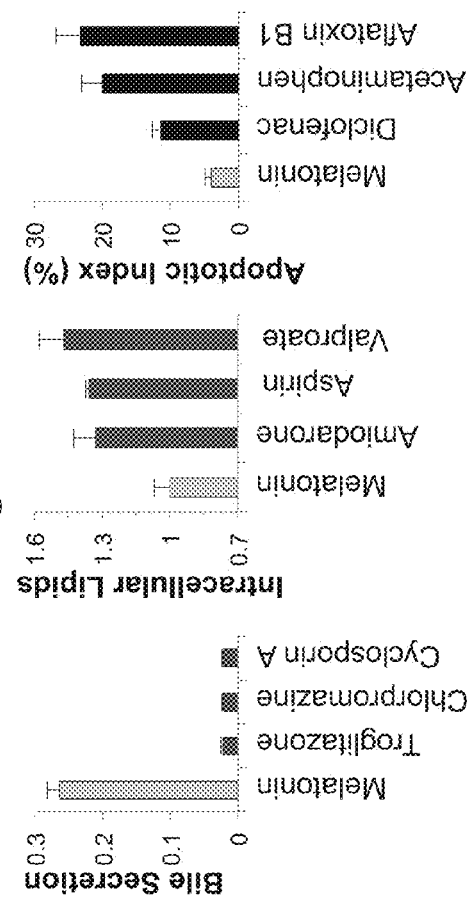

Two phase synchronization

Computer controlled microfluidics can mimic the complex dynamics of hormonal regulation using a simple microfluidic mixer 3 Input mixing

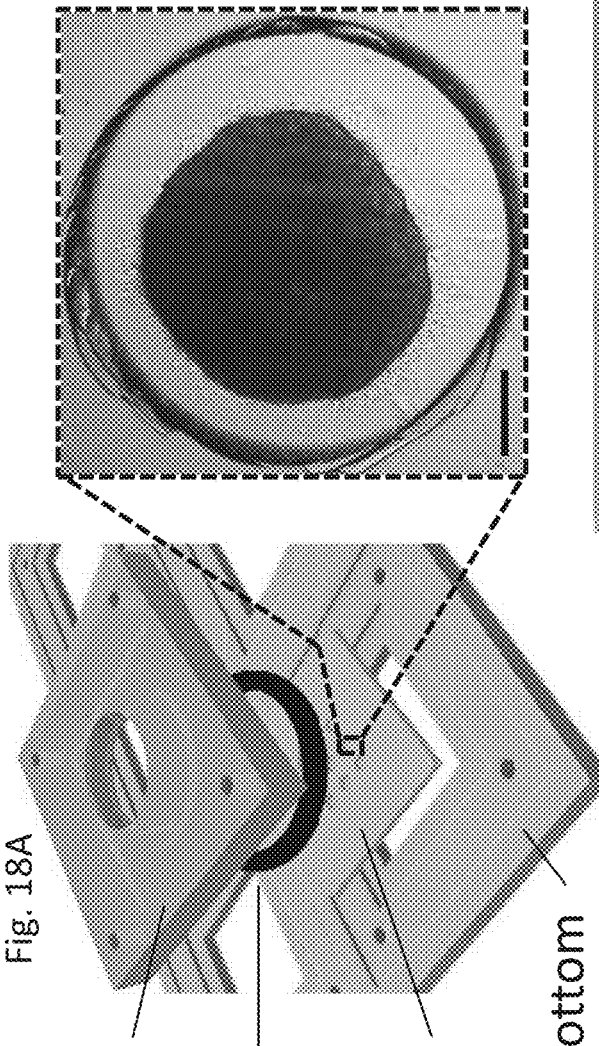
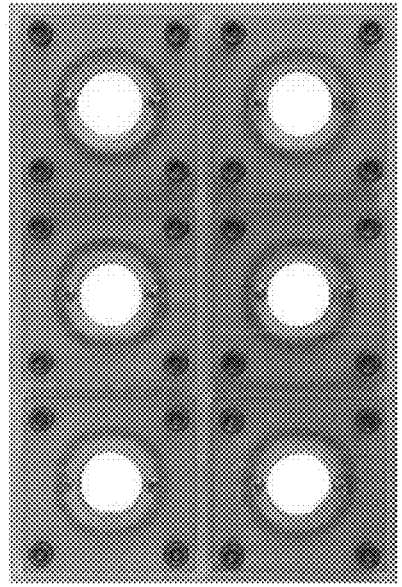
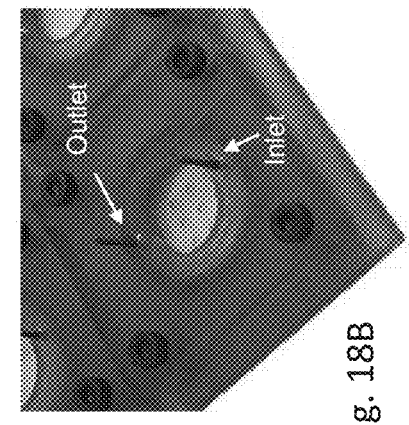
Fig. 18A Microfluidic system: cover with coverslip window, O-ring, PDMS laser cut well with coverslip bottom
- Biocompatible
- Low adhesion
- Low absorbance
- Open configuration
- Seeding
- Multi-plate
Fig. 18B
Fig. 18C Multi-BR system

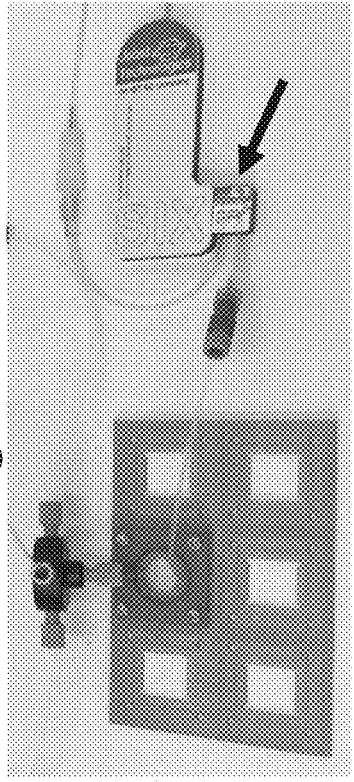
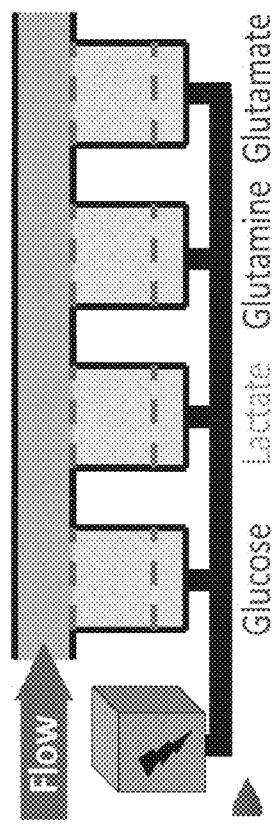
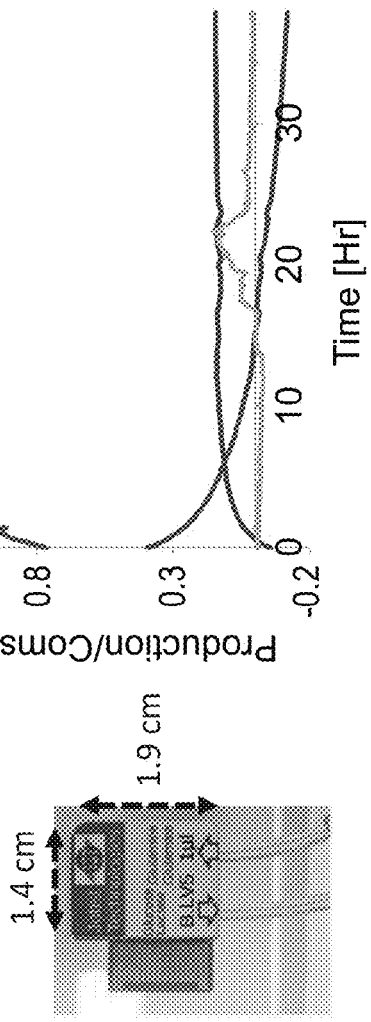

Fig. 22C
| Basal medium | |
|---|---|
| BSA (bovine serum albumin) | 3.75 mg/ml |
| Insulin | 1 μg/ml |
| Transferrin | 7 nM |
| Selenite | 4 nM |
| Glutamine | 2 mM |
| Day peak medium | |
| Dexamethasone | 100 μM |
| Night peak medium | |
| Melatonin | 200 μM |
| GH (growth-hormone) | 30 ng/ml |
| T3 (triiodothyronine) | 10 nM |
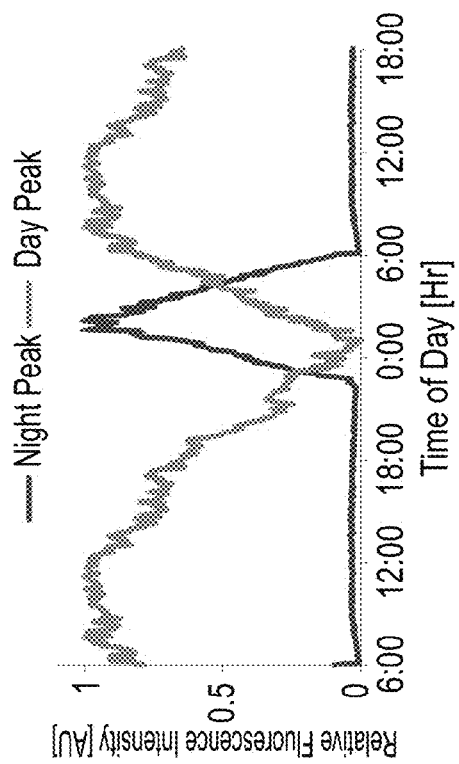
Fig. 22A
Two phase synchronization in vitro
Fig. 22B

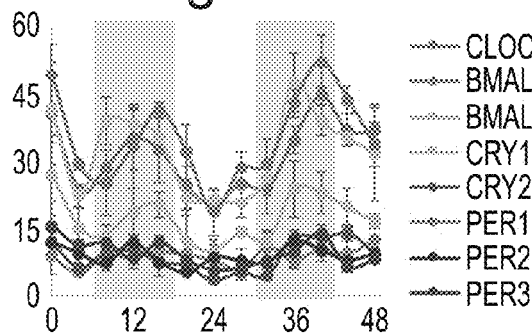
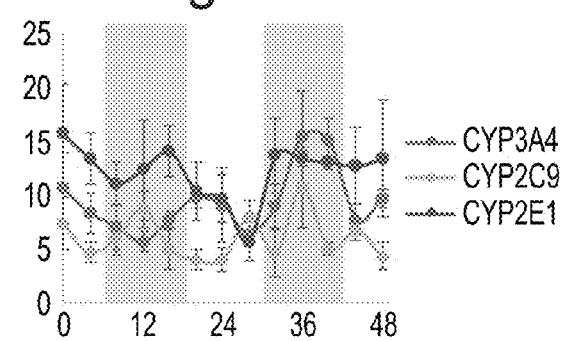
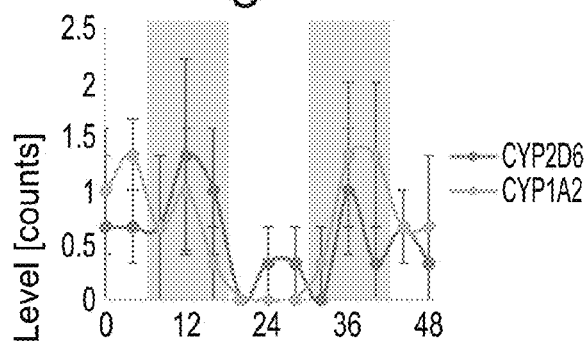
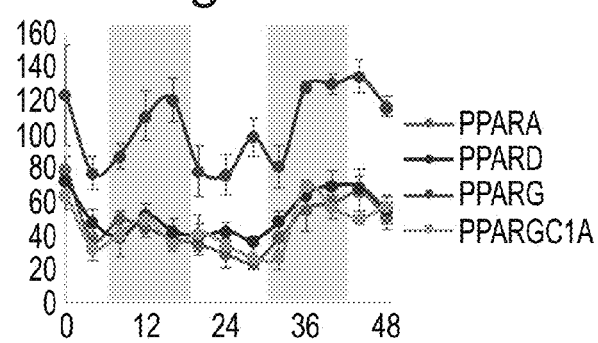
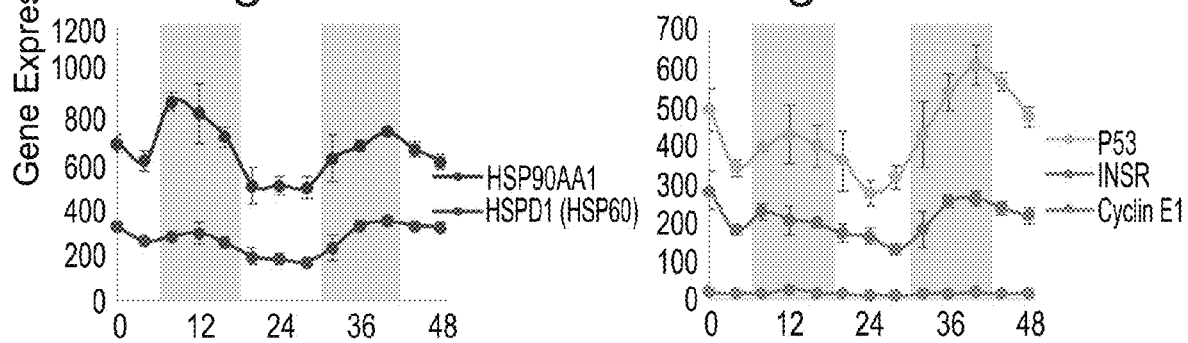
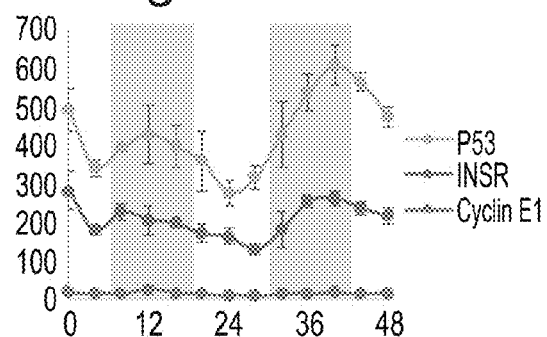
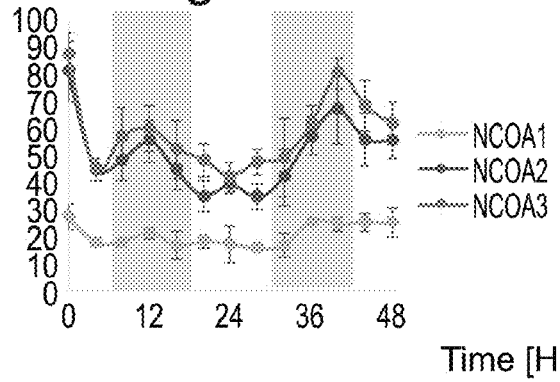
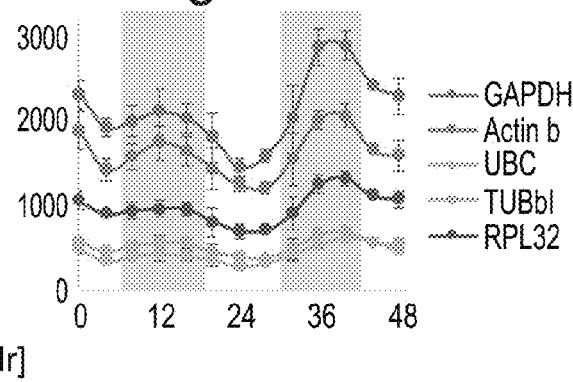

SEQUENCE LISTING

```
<160> NUMBER OF SEQ ID NOS: 30

<210> SEQ ID NO 1
<211> LENGTH: 244
<212> TYPE: PRT
<213> ORGANISM: homo sapiens

<400> SEQUENCE: 1

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160
```

Ala Tyr His Ile Thr Val Tyr Met Lys Asp Val Lys Val Ser Leu Phe
            165                 170                 175

Lys Lys Asp Lys Ala Met Leu Phe Thr Tyr Asp Gln Tyr Gln Glu Asn
        180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 2
<211> LENGTH: 110
<212> TYPE: PRT
<213> ORGANISM: homo sapiens

<400> SEQUENCE: 2

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 3
<211> LENGTH: 209
<212> TYPE: PRT
<213> ORGANISM: homo sapiens

<400> SEQUENCE: 3

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu

His Leu Pro Gly Asn Lys Ser Pro His Arg Asp Pro Ala Pro Arg Gly
145                 150                 155                 160

Pro Ala Arg Phe Leu Pro Leu Gly Leu Pro Pro Ala Leu Pro Glu
            165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
            195                 200                 205

Ser

<210> SEQ ID NO 4
<211> LENGTH: 217
<212> TYPE: PRT
<213> ORGANISM: homo sapiens

<400> SEQUENCE: 4

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 5
<211> LENGTH: 202
<212> TYPE: PRT
<213> ORGANISM: homo sapiens

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Asn Pro Gln Thr Ser Leu Cys
        50                  55                  60

Phe Ser Glu Ser Ile Pro Thr Pro Ser Asn Arg Glu Glu Thr Gln Gln
65                  70                  75                  80

Lys Ser Asn Leu Glu Leu Leu Arg Ile Ser Leu Leu Leu Ile Gln Ser
                85                  90                  95

Trp Leu Glu Pro Val Gln Phe Leu Arg Ser Val Phe Ala Asn Ser Leu
            100                 105                 110

Val Tyr Gly Ala Ser Asp Ser Asn Val Tyr Asp Leu Leu Lys Asp Leu
        115                 120                 125

Glu Glu Gly Ile Gln Thr Leu Met Gly Arg Leu Glu Asp Gly Ser Pro
    130                 135                 140

Arg Thr Gly Gln Ile Phe Lys Gln Thr Tyr Ser Lys Phe Asp Thr Asn
145                 150                 155                 160

Ser His Asn Asp Asp Ala Leu Leu Lys Asn Tyr Gly Leu Leu Tyr Cys
                165                 170                 175

Phe Arg Lys Asp Met Asp Lys Val Glu Thr Phe Leu Arg Ile Val Gln
            180                 185                 190

Cys Arg Ser Val Glu Gly Ser Cys Gly Phe
        195                 200

<210> SEQ ID NO 6
<211> LENGTH: 177
<212> TYPE: PRT
<213> ORGANISM: homo sapiens

<400> SEQUENCE: 6

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Asn Leu Glu Leu Leu Arg Ile
        50                  55                  60

Ser Leu Leu Leu Ile Gln Ser Trp Leu Glu Pro Val Gln Phe Leu Arg
65                  70                  75                  80

Ser Val Phe Ala Asn Ser Leu Val Tyr Gly Ala Ser Asp Ser Asn Val
                85                  90                  95

Tyr Asp Leu Leu Lys Asp Leu Glu Glu Gly Ile Gln Thr Leu Met Gly
            100                 105                 110

Arg Leu Glu Asp Gly Ser Pro Arg Thr Gly Gln Ile Phe Lys Gln Thr
        115                 120                 125

Tyr Ser Lys Phe Asp Thr Asn Ser His Asn Asp Asp Ala Leu Leu Lys
    130                 135                 140

Asn Tyr Gly Leu Leu Tyr Cys Phe Arg Lys Asp Met Asp Lys Val Glu
145                 150                 155                 160

Thr Phe Leu Arg Ile Val Gln Cys Arg Ser Val Glu Gly Ser Cys Gly
                165                 170                 175

Phe

<210> SEQ ID NO 7

<211> LENGTH: 227
<212> TYPE: PRT
<213> ORGANISM: homo sapiens

<400> SEQUENCE: 7

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro Leu Pro Ile Cys
            20                  25                  30

Pro Gly Gly Ala Ala Arg Cys Gln Val Thr Leu Arg Asp Leu Phe Asp
        35                  40                  45

Arg Ala Val Val Leu Ser His Tyr Ile His Asn Leu Ser Ser Glu Met
50                  55                  60

Phe Ser Glu Phe Asp Lys Arg Tyr Thr His Gly Arg Gly Phe Ile Thr
65                  70                  75                  80

Lys Ala Ile Asn Ser Cys His Thr Ser Ser Leu Ala Thr Pro Glu Asp
                85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
        115                 120                 125

Glu Val Arg Gly Met Gln Glu Ala Pro Glu Ala Ile Leu Ser Lys Ala
130                 135                 140

Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
                165                 170                 175

Val Trp Ser Gly Leu Pro Ser Leu Gln Met Ala Asp Glu Glu Ser Arg
            180                 185                 190

Leu Ser Ala Tyr Tyr Asn Leu Leu His Cys Leu Arg Arg Asp Ser His
        195                 200                 205

Lys Ile Asp Asn Tyr Leu Lys Leu Leu Lys Cys Arg Ile Ile His Asn
    210                 215                 220

Asn Asn Cys
225

<210> SEQ ID NO 8
<211> LENGTH: 138
<212> TYPE: PRT
<213> ORGANISM: homo sapiens

<400> SEQUENCE: 8

Met Thr Ala Leu Phe Leu Met Ser Met Leu Phe Gly Leu Thr Cys Gly
1               5                   10                  15

Gln Ala Met Ser Phe Cys Ile Pro Thr Glu Tyr Thr Met His Ile Glu
            20                  25                  30

Arg Arg Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Ile Tyr Arg
65                  70                  75                  80

Thr Val Glu Ile Pro Gly Cys Pro Leu His Val Ala Pro Tyr Phe Ser
                85                  90                  95

Tyr Pro Val Ala Leu Ser Cys Lys Cys Gly Lys Cys Asn Thr Asp Tyr
            100                 105                 110

Ser Asp Cys Ile His Glu Ala Ile Lys Thr Asn Tyr Cys Thr Lys Pro
        115                 120                 125

Gln Lys Ser Tyr Leu Val Gly Phe Ser Val
        130                 135

<210> SEQ ID NO 9
<211> LENGTH: 93
<212> TYPE: PRT
<213> ORGANISM: homo sapiens

<400> SEQUENCE: 9

Met Leu Ser Phe Leu Phe Phe Pro Gln Asp Ile Asn Gly Lys Leu Phe
1               5                   10                  15

Leu Pro Lys Tyr Ala Leu Ser Gln Asp Val Cys Thr Tyr Arg Asp Phe
            20                  25                  30

Ile Tyr Arg Thr Val Glu Ile Pro Gly Cys Pro Leu His Val Ala Pro
        35                  40                  45

Tyr Phe Ser Tyr Pro Val Ala Leu Ser Cys Lys Cys Gly Lys Cys Asn
    50                  55                  60

Thr Asp Tyr Ser Asp Cys Ile His Glu Ala Ile Lys Thr Asn Tyr Cys
65                  70                  75                  80

Thr Lys Pro Gln Lys Ser Tyr Leu Val Gly Phe Ser Val
                85                  90

<210> SEQ ID NO 10
<211> LENGTH: 164
<212> TYPE: PRT
<213> ORGANISM: homo sapiens

<400> SEQUENCE: 10

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140

Arg Leu Val Gln Leu Ala Gly Ala Pro Glu Pro Phe Glu Pro Ala Gln
145                 150                 155                 160

Pro Asp Ala Tyr

<210> SEQ ID NO 11
<211> LENGTH: 4629
<212> TYPE: DNA
<213> ORGANISM: homo sapiens

```
<400> SEQUENCE: 11
aggctgttga ggctgggcca tctcctcctc acttccattc tgactgcagt ctgtggttct      60
gattccatac cagaggagac gggatttcac catgttgtcc aggctggtct gaaactcctg     120
acatcagggc tcaggatgct gttgctggga gctgttctac tgctattagc tctgcccggt     180
catgaccagg aaaccacgac tcaagggccc ggagtcctgc ttcccctgcc caaggggcc      240 tgcacaggtt ggatggcggg catcccaggg catccgggcc ataatgggc cccaggccgt      300 gatggcagag atggcacccc tggtgagaag ggtgagaaag gagatccagg tcttattggt     360
cctaagggag acatcggtga accggagta cccggggctg aaggtccccg aggctttccg      420
ggaatccaag gcaggaaagg agaacctgga gaaggtgcct atgtataccg ctcagcattc     480
agtgtgggat tggagactta cgttactatc cccaacatgc ccattcgctt taccaagatc     540
ttctacaatc agcaaaacca ctatgatggc tccactggta aattccactg caacattcct     600
gggctgtact actttgccta ccacatcaca gtctatatga aggatgtgaa ggtcagcctc     660
ttcaagaagg acaaggctat gctcttcacc tatgatcagt accaggaaaa taatgtggac     720
caggcctccg gctctgtgct cctgcatctg gaggtgggcg accaagtctg gctccaggtg     780 tatgggaag gagagcgtaa tggactctat gctgataatg acaatgactc caccttcaca     840
ggctttcttc tctaccatga caccaactga tcaccactaa ctcagagcct cctccaggcc     900
aaacagcccc aaagtcaatt aaaggctttc agtacggtta ggaagttgat tattatttag     960
ttggaggcct ttagatatta ttcattcatt tactcattca tttattcatt cattcatcga    1020
gtaactttaa aaaatcata tgctatgttc ccagtcctgg ggagcttcac aaacatgacc     1080
agataactga ctagaaagaa gtagttgaca gtgctatttt gtgcccactg tctctcctga    1140
tgctcatatc aatcctataa ggcacaggga acaagcattc tcctgttttt acagattgta    1200
tcctgaggct gagagagtta agtgaatgtc taaggtcaca cagtattaag tgacagtgct    1260
agaaatcaaa cccagagctg tggactttgt tcactagact gtgccctttt atagaggtac    1320
atgttctctt tggagtgttg gtaggtgtct gtttcccacc tcacctgaga gccattgaat    1380
ttgccttcct catgaattaa aacctccccc aagcagagct tcctcagaga agtggttct     1440 atgatgacgt cctgtcttgg aaggactact actcaatggc ccctgcacta ctctacttcc    1500
tcttacctat gtcccttctc atgccttttcc ctccaacggg aaagccaac tccatctcta    1560 agtgccgaac tcatccctgt tcctcaaggc cacctggcca ggagcttctc tgatgtgata    1620 tccactttt tttttttga gatggagtct cactctgtca cccaggctgg agtacagtga     1680
cacgacctcg gctcactgca gcctccttct cctgggtcca agcaattatt gtgcctcagc    1740
ctcccgagta gctgagactt caggtgcatt ccaccacaca tggctaattt ttgtattttt    1800
agtagaaatg gggtttcgtc atgttggcca ggctggtctc gaactcctgg cctaggtgat    1860
ccacccgcct cgacctccca aagtgctggg attacaggca tgagccacca tgcccagtcg    1920
atatctcact ttttattttg ccatggatga gagtcctggg tgtgaggaac acctcccacc    1980
aggctagagg caactgccca ggaaggactg tgcttccgtc acctctaaat cccttgcaga    2040
tccttgataa atgcctcatg aagaccaatc tcttgaatcc catatctacc cagaattaac    2100
tccattccag tctctgcatg taatcagttt tatccacaga aacattttca ttttaggaaa    2160
tccctggttt taagtatcaa tccttgttca gctggacaat atgaatcttt tccactgaag    2220
ttagggatga ctgtgatttt cagaacacgt ccagaatttt tcatcaagaa ggtagcttga    2280
gcctgaaatg caaaacccat ggaggaattc tgaagccatt gtctccttga gtaccaacag    2340
```

```
ggtcagggaa gactgggcct cctgaattta ttattgttct ttaagaatta caggttgagg    2400
tagttgatgg tggtaaacat tctctcagga gacaataact ccagtgatgt tcttcaaaga    2460
ttttagcaaa aacagagtaa atagcattct ctatcaatat ataaatttaa aaaactatct    2520
ttttgcttac agttttaaat tctgaacaat tctctcttat atgtgtattg ctaatcatta    2580
aggtattatt ttttccacat ataaagcttt gtcttttgt tgttgttgtt gtttttaaga    2640
tggagtttcc ctctgttgcc aggctagagt gcagtggcat gatctcggct tactgcaacc    2700
tttgcctccc aggttcaagc gattcttctg cctcagcctc ccgagtagct gggaccacag    2760
gtgcctacca ccatgccagg ctaattttg tattttagt aaagacaggg tttcaccata    2820
ttggccaggc tggtctcgaa ctcctgacct tgtgatctgc ccgcctccat ttttgttgtt    2880 atttttgag aaagatagat atgaggttta gagagggatg aagaggtgag agtaagcctt    2940
gtgttagtca gaactctgtg ttgtgaatgt cattcacaac agaaaccca aaatattatg    3000 caaactactg taagcaagaa aaataaagga aaatggaaa catttattcc tttgcataat    3060
agaaattacc agagttgttc tgtctttaga taaggtttga accaaagctc aaaacaatca    3120 agacccttt ctgtatgtcc ttctgttctg ccttccgcag tgtaggcttt accctcaggt    3180
gctacacagt atagttctag ggtttccctc ccgatatcaa aaagactgtg gcctgcccag    3240
ctctcgtatc cccaagccac accatctggc taaatggaca tcatgttttc tggtgatgcc    3300
caaagaggag agaggaagct ctctttccca gatgccccag caagtgtaac cttgcatctc    3360
attgctctgg ctgagttgtg tgcctgtttc tgaccaatca ctgagtcagg aggatgaaat    3420
attcatattg acttaattgc agcttaagtt aggggtatgt agaggtattt tccctaaagc    3480
aaaattggga cactgttatc agaaatagga gagtggatga tagatgcaaa ataatacctg    3540
tccacaacaa actcttaatg ctgtgtttga gctttcatga gtttcccaga gagacatagc    3600
tggaaaattc ctattgattt tctctaaaat ttcaacaagt agctaaagtc tggctatgct    3660
cacagtctca catctggttg gggtgggctc cttacagaac acgctttcac agttacccta    3720
aactctctgg ggcagggtta ttcctttgtg gaaccagagg cacagagaga gtcaactgag    3780
gccaaaagag gcctgagaga aactgaggtc aagatttcag gattaatggt cctgtgatgc    3840
tttgaagtac aattgtggat ttgtccaatt ctctttagtt ctgtcagctt ttgcttcata    3900
tattttagcg ctctattatt agatatatac atgtttagta ttatgtctta ttggtgcatt    3960
tactctctta tcattatgta atgtccttct ttatctgtga aattttctg tgttctgaag    4020 tctactttgt ctaaaaataa catacgcact caacttcctt ttctttcttc cttccttct    4080 ttcttccttc ctttctttct ctctctctct ctttccttcc ttccttcctc cttttctttc    4140
tctctctctc tctctctctt tttttgacag actctcgttc tgtggccctg gctggagttc    4200
agtggtgtga tcttggctca ctgctacctc taccatgagc aattctcctg cctcagcctc    4260
ccaagtagct ggaactacag gctcatgcca ctgcgcccag ctaattttg tattttcgt    4320 agagacgggg tttcaccaca ttcgtcaggt tggttcaaa ctcctgactt tgtgatccac    4380
ccgcctcggc ctcccaaagt gctgggatta caggcatgag ccatcacacc tggtcaactt    4440
tcttttgatt agtgttttg tggtatatct ttttccatca tgttacttta aatatatcta    4500
tattattgta tttaaaatgt gtttcttaca gactgcatgt agttgggtat aattttatc    4560 cagtctaaaa atatctgtct tttaattggt gtttagacaa tttatattta ataaaattgt    4620
tgaatttaa                                                           4629
```

<210> SEQ ID NO 12
<211> LENGTH: 4542
<212> TYPE: DNA
<213> ORGANISM: homo sapiens

<400> SEQUENCE: 12

```
attctgactg cagtctgtgg ttctgattcc ataccagagg ggctcaggat gctgttgctg      60
ggagctgttc tactgctatt agctctgccc ggtcatgacc aggaaaccac gactcaaggg     120
cccggagtcc tgcttcccct gcccaagggg gcctgcacag gttggatggc gggcatccca     180
gggcatccgg gccataatgg ggccccaggc cgtgatggca gagatggcac ccctggtgag     240
aagggtgaga aaggagatcc aggtcttatt ggtcctaagg gagacatcgg tgaaaccgga     300
gtacccgggg ctgaaggtcc ccgaggcttt ccgggaatcc aaggcaggaa aggagaacct     360
ggagaaggtg cctatgtata ccgctcagca ttcagtgtgg gattggagac ttacgttact     420
atccccaaca tgcccattcg ctttaccaag atcttctaca atcagcaaaa ccactatgat     480
ggctccactg gtaaattcca ctgcaacatt cctgggctgt actactttgc ctaccacatc     540
acagtctata tgaaggatgt gaaggtcagc ctcttcaaga aggacaaggc tatgctcttc     600
acctatgatc agtaccagga aaataatgtg gaccaggcct ccggctctgt gctcctgcat     660
ctggaggtgg gcgaccaagt ctggctccag gtgtatgggg aaggagagcg taatggactc     720
tatgctgata atgacaatga ctccaccttc acaggctttc ttctctacca tgacaccaac     780
tgatcaccac taactcagag cctcctccag gccaaacagc cccaaagtca attaaaggct     840
ttcagtacgg ttaggaagtt gattattatt tagttggagg cctttagata ttattcattc     900
atttactcat tcatttattc attcattcat cgagtaactt taaaaaaatc atatgctatg     960
ttcccagtcc tggggagctt cacaaacatg accagataac tgactagaaa gaagtagttg    1020
acagtgctat tttgtgccca ctgtctctcc tgatgctcat atcaatccta taaggcacag    1080
ggaacaagca ttctcctgtt tttacagatt gtatcctgag gctgagagag ttaagtgaat    1140
gtctaaggtc acacagtatt aagtgacagt gctagaaatc aaacccagag ctgtggactt    1200
tgttcactag actgtgccct tttatagagg tacatgttct cttggagtg ttggtaggtg     1260 tctgtttccc acctcacctg agagccattg aatttgcctt cctcatgaat taaaacctcc    1320
cccaagcaga gcttcctcag agaaagtggt tctatgatga cgtcctgtct tggaaggact    1380
actactcaat ggcccctgca ctactctact tcctcttacc tatgtccctt ctcatgcctt    1440
tccctccaac ggggaaagcc aactccatct ctaagtgccg aactcatccc tgttcctcaa    1500
ggccacctgg ccaggagctt ctctgatgtg atatccactt tttttttttt tgagatggag    1560
tctcactctg tcacccaggc tggagtacag tgacacgacc tcggctcact gcagcctcct    1620
tctcctgggt ccaagcaatt attgtgcctc agcctcccga gtagctgaga cttcaggtgc    1680
attccaccac acatggctaa ttttgtatt tttagtagaa atggggtttc gtcatgttgg     1740
ccaggctggt ctcgaactcc tggcctaggt gatccacccg cctcgacctc ccaaagtgct    1800
gggattacag gcatgagcca ccatgcccag tcgatatctc acttttatt ttgccatgga     1860 tgagagtcct gggtgtgagg aacacctccc accaggctag aggcaactgc ccaggaagga    1920
ctgtgcttcc gtcacctcta aatcccttgc agatccttga taaatgcctc atgaagacca    1980
atctcttgaa tcccatatct acccagaatt aactccattc cagtctctgc atgtaatcag    2040
ttttatccac agaaacattt tcattttagg aaatccctgg ttttaagtat caatccttgt    2100
tcagctggac aatatgaatc ttttccactg aagttaggga tgactgtgat tttcagaaca    2160
```

```
cgtccagaat ttttcatcaa gaaggtagct tgagcctgaa atgcaaaacc catggaggaa    2220
ttctgaagcc attgtctcct tgagtaccaa cagggtcagg gaagactggg cctcctgaat    2280
ttattattgt tctttaagaa ttacaggttg aggtagttga tggtggtaaa cattctctca    2340
ggagacaata actccagtga tgttcttcaa agattttagc aaaaacagag taaatagcat    2400
tctctatcaa tatataaatt taaaaaacta tcttttttgct tacagtttta aattctgaac    2460
aattctctct tatatgtgta ttgctaatca ttaaggtatt attttttcca catataaagc    2520
tttgtctttt tgttgttgtt gttgtttta agatggagtt tccctctgtt gccaggctag    2580
agtgcagtgg catgatctcg gcttactgca acctttgcct cccaggttca agcgattctt    2640
ctgcctcagc ctcccgagta gctgggacca caggtgccta ccaccatgcc aggctaattt    2700
ttgtattttt agtaaagaca gggtttcacc atattggcca ggctggtctc gaactcctga    2760
ccttgtgatc tgcccgcctc cattttgtt gttattttt gagaaagata gatatgaggt    2820
ttagagaggg atgaagaggt gagagtaagc cttgtgttag tcagaactct gtgttgtgaa    2880
tgtcattcac aacagaaaac ccaaaatatt atgcaaacta ctgtaagcaa gaaaaataaa    2940
ggaaaaatgg aaacatttat tcctttgcat aatagaaatt accagagttg ttctgtcttt    3000
agataaggtt tgaaccaaag ctcaaaacaa tcaagaccct tttctgtatg tccttctgtt    3060
ctgccttccg cagtgtaggc tttaccctca ggtgctacac agtatagttc tagggtttcc    3120
ctcccgatat caaaaagact gtggcctgcc cagctctcgt atccccaagc cacaccatct    3180
ggctaaatgg acatcatgtt ttctggtgat gcccaaagag gagagaggaa gctctctttc    3240
ccagatgccc cagcaagtgt aaccttgcat ctcattgctc tggctgagtt gtgtgcctgt    3300
ttctgaccaa tcactgagtc aggaggatga aatattcata ttgacttaat tgcagcttaa    3360 gttagggta tgtagaggta ttttccctaa agcaaaattg ggacactgtt atcagaaata    3420
ggagagtgga tgatagatgc aaaataatac ctgtccacaa caaactctta atgctgtgtt    3480
tgagctttca tgagtttccc agagagacat agctggaaaa ttcctattga ttttctctaa    3540
aatttcaaca gtagctaaa gtctggctat gctcacagtc tcacatctgg ttggggtggg    3600
ctccttacag aacacgcttt cacagttacc ctaaactctc tggggcaggg ttattccttt    3660
gtggaaccag aggcacagag agagtcaact gaggccaaaa gaggcctgag agaaactgag    3720
gtcaagattt caggattaat ggtcctgtga tgctttgaag tacaattgtg gatttgtcca    3780
attctcttta gttctgtcag cttttgcttc atatatttta gcgctctatt attagatata    3840
tacatgttta gtattatgtc ttattggtgc atttactctc ttatcattat gtaatgtcct    3900
tctttatctg tgataatttt ctgtgttctg aagtctactt tgtctaaaaa taacatacgc    3960
actcaacttc ttttcttc ttccttcctt tcttttcttcc ttcctttctt tctctctctc    4020
tctctttcct tccttccttc ctccttttct ttctctctct ctctctctct cttttttga    4080 cagactctcg ttctgtggcc ctggctgag ttcagtggtg tgatcttggc tcactgctac    4140
ctctaccatg agcaattctc ctgcctcagc ctcccaagta gctggaacta caggctcatg    4200
ccactgcgcc cagctaattt ttgtattttt cgtagagacg gggtttcacc acattcgtca    4260 ggttggttc aaactcctga ctttgtgatc caccgcctc ggcctcccaa agtgctggga    4320
ttacaggcat gagccatcac acctggtcaa ctttcttttg attagtgttt tgtggtata    4380 tcttttcca tcatgttact ttaaatatat ctatattatt gtatttaaaa tgtgtttctt    4440
acagactgca tgtagttggg tataattttt atccagtcta aaaatatctg tcttttaatt    4500
```
ggtgtttaga caatttatat ttaataaaat tgttgaattt aa        4542

<210> SEQ ID NO 13
<211> LENGTH: 469
<212> TYPE: DNA
<213> ORGANISM: homo sapiens

<400> SEQUENCE: 13
agccctccag acaggctgc atcagaagag gccatcaagc agatcactgt ccttctgcca     60
tggccctgtg gatgcgcctc ctgcccctgc tggcgctgct ggccctctgg ggacctgacc    120
cagccgcagc ctttgtgaac caacacctgt gcggctcaca cctggtggaa gctctctacc    180
tagtgtgcgg ggaacgaggc ttcttctaca cacccaagac ccgccgggag cagaggacc     240
tgcaggtggg gcaggtggag ctgggcgggg gccctggtgc aggcagcctg cagcccttgg    300
ccctggaggg gtccctgcag aagcgtggca ttgtggaaca atgctgtacc agcatctgct    360
ccctctacca gctggagaac tactgcaact agacgcagcc cgcaggcagc ccacacccg     420
ccgcctcctg caccgagaga gatggaataa agcccttgaa ccagcaaaa               469

<210> SEQ ID NO 14
<211> LENGTH: 495
<212> TYPE: DNA
<213> ORGANISM: homo sapiens

<400> SEQUENCE: 14
agccctccag acaggctgc atcagaagag gccatcaagc aggtctgttc caagggcctt     60
tgcgtcagat cactgtcctt ctgccatggc cctgtgatg cgcctcctgc ccctgctggc    120
gctgctggcc ctctggggac tgacccagc cgcagccttt gtgaaccaac ctgtgcgg     180
ctcacacctg gtgaagctc tctacctagt gtgcggggaa cgaggcttct tctacacacc    240
caagacccgc cgggaggcag aggacctgca ggtggggcag gtggagctgg cggggggccc    300
tggtgcaggc agcctgcagc ccttggcct ggaggggtcc ctgcagaagc gtggcattgt    360
ggacaatgc tgtaccagca tctgctccct ctaccagctg agaactact gcaactagac    420
gcagccccgca ggcagccca cccgccgc ctcctgcacc gagagagatg gaataaagcc    480
cttgaaccag caaaa                                                    495

<210> SEQ ID NO 15
<211> LENGTH: 648
<212> TYPE: DNA
<213> ORGANISM: homo sapiens

<400> SEQUENCE: 15
agccctccag acaggctgc atcagaagag gccatcaagc aggtctgttc caagggcctt     60
tgcgtcaggt gggctcagga ttccagggtg gctggacccc aggccccagc tctgcagcag    120
ggaggacgtg gctgggctcg tgaagcatgt gggggtgagc ccaggggccc aaggcaggg    180
cacctggcct tcagcctgcc tcagccctgc ctgtctccca gatcactgtc cttctgccat    240
ggccctgtgg atgcgcctcc tgccctgct ggcgctgctg gccctctggg gacctgaccc    300
agccgcagcc tttgtgaacc aacacctgtg cggctcacac ctggtggaag ctctctacct    360
agtgtgcggg gaacgaggct tcttctacac acccaagacc cgccgggagg cagaggacct    420
gcaggtgggg caggtggagc tgggcggggg ccctggtgca ggcagcctgc agcccttggc    480
cctggagggg tccctgcaga agcgtggcat tgtggaacaa tgctgtacca gcatctgctc    540
cctctaccag ctggagaact actgcaacta gacgcagccc gcaggcagcc ccacacccgc    600
cgcctcctgc accgagagag atggaataaa gcccttgaac cagcaaaa 648

<210> SEQ ID NO 16
<211> LENGTH: 529
<212> TYPE: DNA
<213> ORGANISM: homo sapiens

<400> SEQUENCE: 16
agccctccag gacaggctgc atcagaagag gccatcaagc aggtctgttc caagggcctt 60
tgcgtcaggt gggctcagga ttccaggggtg gctggacccc agatcactgt ccttctgcca 120
tggccctgtg gatgcgcctc ctgccccctgc tggcgctgct ggccctctgg ggacctgacc 180
cagccgcagc ctttgtgaac caacacctgt gcggctcaca cctggtggaa gctctctacc 240
tagtgtgcgg ggaacgaggc ttcttctaca cacccaagac ccgccgggag cagaggacc 300 tgcaggtggg gcaggtggag ctgggcgggg ccctggtgc aggcagcctg cagcccttgg 360
ccctggaggg gtccctgcag aagcgtggca ttgtggaaca atgctgtacc agcatctgct 420
ccctctacca gctggagaac tactgcaact agacgcagcc cgcaggcagc cccacacccg 480
ccgcctcctg caccgagaga gatggaataa agcccttgaa ccagcaaaa 529

<210> SEQ ID NO 17
<211> LENGTH: 1333
<212> TYPE: DNA
<213> ORGANISM: homo sapiens

<400> SEQUENCE: 17
gaggcttcca aggcaggata cttgtgtctc agatgcggtc gcttctttca tacagcaatt 60
gccgccttgc tgaggatcaa ggaacctcag tgtcagatca cgccctcccc ccaaacttag 120
aaattcagat ggggcgcaga aatttctctt gttctgcgtg atctgcatag atggtccaag 180
aggtggtttt tccaggagcc cagcacccct cctccctccg actcagaccc aggagtctgg 240
ccctccattg aaaggacccc aggttacatc atccattcag gctgcccttg ccacgatgga 300
attctgtagc tcctgccaaa tgggtcaaat atcatggttc aggcgcaggg aggtgattg 360 ggcgggcctg tctgggtata aattctggag cttctgcatc tatcccaaaa aacaagggtg 420
ttctgtcagc tgaggatcca gccgaaagag gagccaggca ctcaggccac ctgagtctac 480
tcacctggac aactggaatc tggcaccaat tctaaaccac tcagcttctc cgagctcaca 540
ccccggagat cacctgagga cccgagccat tgatggactc ggacgagacc gggttcgagc 600
actcaggact gtgggtttct gtgctggctg gtcttctgct gggagcctgc caggcacacc 660
ccatccctga ctccagtcct ctcctgcaat tcggggggcca agtccggcag cggtacctct 720
acacagatga tgcccagcag acagaagccc acctggagat caggggaggat gggacggtgg 780 ggggcgctgc tgaccagagc cccgaaagtc tcctgcagct gaaagccttg aagccgggag 840
ttattcaaat cttgggagtc aagacatcca ggttcctgtg ccagcggcca gatgggccc 900 tgtatggatc gctccacttt gaccctgagg cctgcagctt ccgggagctg cttcttgagg 960
acggatacaa tgtttaccag tccgaagccc acggcctccc gctgcacctg ccagggaaca 1020
agtccccaca ccgggaccct gcaccccgag accagctcg cttcctgcca ctaccaggcc 1080
tgccccccgc actcccggag ccacccggaa tcctggcccc ccagcccccc gatgtgggct 1140
cctcggaccc tctgagcatg gtgggaccctt cccaggccg aagccccagc tacgcttcct 1200
gaagccagag gctgttact atgacatctc ctctttattt attaggttat ttatcttatt 1260

```
tattttttta tttttcttac ttgagataat aaagagttcc agaggaggat aaaaaaaaaa    1320
aaaaaaaaaa aaa                                                        1333

<210> SEQ ID NO 18
<211> LENGTH: 823
<212> TYPE: DNA
<213> ORGANISM: homo sapiens

<400> SEQUENCE: 18
aaggatccca aggcccaact ccccgaacca ctcagggtcc tgtggacagc tcacctagct      60
gcaatggcta caggctcccg gacgtccctg ctcctggctt ttggcctgct ctgcctgccc     120
tggcttcaag agggcagtgc cttcccaacc attcccttat ccaggctttt tgacaacgct     180
atgctccgcg cccatcgtct gcaccagctg gcctttgaca cctaccagga gtttgaagaa     240
gcctatatcc caaggaaca gaagtattca ttcctgcaga accccagac ctccctctgt      300 ttctcagagt ctattccgac accctccaac agggaggaaa cacaacagaa atccaaccta     360
gagctgctcc gcatctccct gctgctcatc agtcgtggc tggagcccgt gcagttcctc     420
aggagtgtct tcgccaacag cctggtgtac ggcgcctctg acagcaacgt ctatgacctc     480
ctaaaggacc tagaggaagg catccaaacg ctgatgggga ggctggaaga tggcagcccc     540
cggactgggc agatcttcaa gcagacctac agcaagttcg acacaaactc acacaacgat     600
gacgcactac tcaagaacta cgggctgctc tactgcttca ggaaggacat ggacaaggtc     660
gagacattcc tgcgcatcgt gcagtgccgc tctgtggagg gcagctgtgg cttctagctg     720
cccgggtggc atccctgtga cccctcccca gtgcctctcc tggccctgga agttgccact     780
ccagtgccca ccagccttgt cctaataaaa ttaagttgca tca                      823

<210> SEQ ID NO 19
<211> LENGTH: 815
<212> TYPE: DNA
<213> ORGANISM: homo sapiens

<400> SEQUENCE: 19
aagagaccag ctcaaggatc ccaaggccca actccccgaa ccactcaggg tcctgtggac      60
agctcaccta gctgcaatgg ctacaggctc ccggacgtcc ctgctcctgg cttttggcct     120
gctctgcctg ccctggcttc aagagggcag tgccttccca accattccct tatccaggct     180
ttttgacaac gctatgctcc gcgcccatcg tctgcaccag ctggcctttg acacctacca     240
ggagtttaac ccccagacct ccctctgttt ctcagagtct attccgacac cctccaacag     300
ggaggaaaca caacagaaat ccaacctaga gctgctccgc atctccctgc tgctcatcca     360
gtcgtggctg agcccgtgc agttcctcag gagtgtcttc gccaacagcc tggtgtacgg     420
cgcctctgac agcaacgtct atgacctcct aaaggaccta gaggaaggca tccaaacgct     480
gatggggagg ctggaagatg gcagcccccg gactgggcag atcttcaagc agacctacag     540
caagttcgac acaaactcac acaacgatga cgcactactc aagaactacg ggctgctcta     600
ctgcttcagg aaggacatgg acaaggtcga gacattcctg cgcatcgtgc agtgccgctc     660
tgtggagggc agctgtggct ctagctgccg ggtggcatcc ctgtgaccc ctccccagt     720 gcctctcctg gccctggaag ttgccactcc agtgcccacc agccttgtcc taataaaatt     780
aagttgcatc attttgtctg aaaaaaaaaa aaaaa                               815

<210> SEQ ID NO 20
<211> LENGTH: 740
```

<212> TYPE: DNA
<213> ORGANISM: homo sapiens

<400> SEQUENCE: 20

```
aagagaccag ctcaaggatc ccaaggccca actccccgaa ccactcaggg tcctgtggac    60
agctcaccta gctgcaatgg ctacaggctc ccggacgtcc ctgctcctgg cttttggcct   120
gctctgcctg ccctggcttc aagagggcag tgccttccca accattccct tatccaggct   180
ttttgacaac gctatgctcc gcgcccatcg tctgcaccag ctggcctttg acacctacca   240
ggagtttaac ctagagctgc tccgcatctc cctgctgctc atccagtcgt ggctggagcc   300
cgtgcagttc tcaggagtg tcttcgccaa cagcctggtg tacggcgcct ctgacagcaa   360
cgtctatgac ctcctaaagg acctagagga aggcatccaa acgctgatgg ggaggctgga   420
agatggcagc ccccggactg gcagatcttc aagcagacc tacagcaagt cgacacaaa   480
ctcacacaac gatgacgcac tactcaagaa ctacggctg ctctactgct tcaggaagga   540
catggacaag gtcgagacat cctgcgcat cgtgcagtgc cgctctgtgg agggcagctg   600
tggcttctag ctgcccgggt ggcatccctg tgacccctcc ccagtgcctc tcctggccct   660
ggaagttgcc actccagtgc ccaccagcct tgtcctaata aaattaagtt gcatcatttt   720
gtctgaaaaa aaaaaaaaaa                                              740
```

<210> SEQ ID NO 21
<211> LENGTH: 894
<212> TYPE: DNA
<213> ORGANISM: homo sapiens

<400> SEQUENCE: 21

```
gtgagacttc cagatcttct ctggtgaagt gtgtttcctg caacgatcac gaacatgaac    60
atcaaaggat cgccatggaa agggtccctc ctgctgctgc tggtgtcaaa cctgctcctg   120
tgccagagcg tggccccctt gcccatctgt cccggcgggg ctgcccgatg ccaggtgacc   180
cttcgagacc tgtttgaccg cgccgtcgtc ctgtcccact acatccataa cctctcctca   240
gaaatgttca gcgaattcga taaacggtat acccatggcc ggggttcat taccaaggcc   300
atcaacagct gccacacttc ttcccttgcc accccgaag acaaggagca agcccaacag   360
atgaatcaaa aagactttct gagcctgata gtcagcatat tgcgatcctg gaatgagcct   420
ctgtatcatc tggtcacgga agtacgtggt atgcaagaag ccccggaggc tatcctatcc   480
aaagctgtag agattgagga gcaaaccaaa cggcttctag agggcatgga gctgatagtc   540
agccaggttc atcctgaaac caagaaaat gagatctacc ctgtctggtc gggacttcca   600
tccctgcaga tggctgatga agagtctcgc ctttctgctt attataacct gctccactgc   660
ctacgcaggg attcacataa aatcgacaat tatctcaagc cctgaagtg ccgaatcatc   720
cacaacaaca actgctaagc ccacatccat ttcatctatt tctgagaagg tccttaatga   780
tccgttccat tgcaagcttc ttttagttgt atctcttttg aatccatgct tgggtgtaac   840
aggtctcctc ttaaaaaata aaaactgact ccttagagac atcaaaatct aaaa          894
```

<210> SEQ ID NO 22
<211> LENGTH: 1043
<212> TYPE: DNA
<213> ORGANISM: homo sapiens

<400> SEQUENCE: 22

```
ctgacgtttc tataaagtag gtcataagaa ccttcattcc agaagtaccc tcaaagacag    60
```

| | |
|---|---|
| agacaccaag aagaatcgga acatacaggc tttgatatca aaggtttata aagccaatat | 120 |
| ctgggaaaga gaaaaccgtg agacttccag atcttctctg gtgaagtgtg tttcctgcaa | 180 |
| cgatcacgaa catgaacatc aaaggatcgc catggaaagg gtccctcctg ctgctgctgg | 240 |
| tgtcaaacct gctcctgtgc cagagcgtgg ccccccttgcc catctgtccc ggcggggctg | 300 |
| cccgatgcca ggtgacccctt cgagacctgt ttgaccgcgc cgtcgtcctg tcccactaca | 360 |
| tccataacct ctcctcagaa atgttcagcg aattcgataa acggtatacc catgccggg | 420 |
| ggttcattac caaggccatc aacagctgcc acacttcttc ccttgccacc cccgaagaca | 480 |
| aggagcaagc ccaacagatg aatcaaaaag actttctgag cctgatagtc agcatattgc | 540 |
| gatcctggaa tgagcctctg tatcatctgg tcacggaagt acgtggtatg caagaagccc | 600 |
| cggaggctat cctatccaaa gctgtagaga ttgaggagca aaccaaacgg cttctagagg | 660 |
| gcatggagct gatagtcagc caggttcatc ctgaaaccaa agaaaatgag atctaccctg | 720 |
| tctggtcggg acttccatcc ctgcagatgg ctgatgaaga gtctcgcctt tctgcttatt | 780 |
| ataacctgct ccactgccta cgcagggatt cacataaaat cgacaattat ctcaagctcc | 840 |
| tgaagtgccg aatcatccac aacaacaact gctaagccca catccatttc atctatttct | 900 |
| gagaaggtcc ttaatgatcc gttccattgc aagcttcttt tagttgtatc tcttttgaat | 960 |
| ccatgcttgg gtgtaacagg tctcctctta aaaataaaaa actgactcct tagagacatc | 1020 |
| aaaatctaaa atgaaaaaaa aaa | 1043 |

<210> SEQ ID NO 23
<211> LENGTH: 537
<212> TYPE: DNA
<213> ORGANISM: homo sapiens

<400> SEQUENCE: 23

| | |
|---|---|
| gggtcaccac agcatctgct caccaatgca aagtaagcat gactgctctc tttctgatgt | 60 |
| ccatgctttt tggccttaca tgtgggcaag cgatgtcttt ttgtattcca actgagtata | 120 |
| caatgcacat cgaaaggaga gagtgtgctt attgcctaac catcaacacc accatctgtg | 180 |
| ctggatattg tatgacacgg gatatcaatg gcaaactgtt tcttcccaaa tatgctctgt | 240 |
| cccaggatgt ttgcacatat agagacttca tctacaggac tgtagaaata ccaggatgcc | 300 |
| cactccatgt tgctccctat ttttcctatc ctgttgcttt aagctgtaag tgtggcaagt | 360 |
| gcaatactga ctatagtgac tgcatacatg aagccatcaa gacaaactac tgtaccaaac | 420 |
| ctcagaagtc ttatctggta ggattttctg tctaatagtg atataatttg caatttggtt | 480 |
| aaatgtgctt gcctgaaata aagctaataa aaatattatg tttcacatta tcttctg | 537 |

<210> SEQ ID NO 24
<211> LENGTH: 364
<212> TYPE: DNA
<213> ORGANISM: homo sapiens

<400> SEQUENCE: 24

| | |
|---|---|
| atgctctctt ttctgttctt tccccaggat atcaatggca aactgtttct tcccaaatat | 60 |
| gctctgtccc aggatgtttg cacatataga gacttcatct acaggactgt agaaatacca | 120 |
| ggatgcccac tccatgttgc tccctatttt tcctatcctg ttgctttaag ctgtaagtgt | 180 |
| ggcaagtgca atactgacta tagtgactgc atacatgaag ccatcaagac aaactactgt | 240 |
| accaaacctc agaagtctta tctggtagga ttttctgtct aatagtgata taatttgcaa | 300 |
| tttggttaaa tgtgcttgcc tgaaataaag ctaataaaaa tattatgttt cacattatct | 360 |

```
tctg                                                                    364

<210> SEQ ID NO 25
<211> LENGTH: 621
<212> TYPE: DNA
<213> ORGANISM: homo sapiens

<400> SEQUENCE: 25
acagagccac caagcagtgc tgcatacggg gtccacctgt gtgcaccagg atgcctgaca      60
ccatgctgcc cgcctgcttc ctcggcctac tggccttctc ctccgcgtgc tacttccaga     120
actgcccgag gggcggcaag agggccatgt ccgacctgga gctgagacag tgcctccccct   180 gcggccccgg gggcaaaggc cgctgcttcg ggcccagcat ctgctgcgcg gacgagctgg     240
gctgcttcgt gggcacggct gaggcgctgc gctgccagga ggagaactac ctgccgtcgc     300
cctgccagtc cggccagaag gcgtgcggga gcggggccg ctgcgccgcc ttcggcgttt      360
gctgcaacga cgagagctgc gtgaccgagc ccgagtgccg cgagggcttt caccgccgcg     420
cccgcgccag cgaccggagc aacgccacgc agctggacgg gccggccggg gccttgctgc     480
tgcggctggt gcagctggcc ggggcgcccg agcccttcga gcccgcccag cccgacgcct     540
actgagcccc gcgctcgccc caccggcgcg ctcttcgcgc ccgcccctgc agcacggaca     600
ataaacctcc gccaatgcaa a                                                621

<210> SEQ ID NO 26
<211> LENGTH: 117
<212> TYPE: PRT
<213> ORGANISM: homo sapiens

<400> SEQUENCE: 26

Met Pro Ser Pro Gly Thr Val Cys Ser Leu Leu Leu Leu Gly Met Leu
 1               5                  10                  15

Trp Leu Asp Leu Ala Met Ala Gly Ser Ser Phe Leu Ser Pro Glu His
             20                  25                  30

Gln Arg Val Gln Gln Arg Lys Glu Ser Lys Lys Pro Pro Ala Lys Leu
         35                  40                  45

Gln Pro Arg Ala Leu Ala Gly Trp Leu Arg Pro Glu Asp Gly Gly Gln
     50                  55                  60

Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
                 85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 27
<211> LENGTH: 1374
<212> TYPE: DNA
<213> ORGANISM: homo sapiens

<400> SEQUENCE: 27
agttccccaa agataacaca gctttgcaca gtggatgttt acttgctggt ggtcttatct      60
aagatcaaca ttggcagctg tgcccggaga ggcctccagg gtccaggtcc aatgcacttc     120
cctctcagaa gaggcatccg ctaaaatagg gaccaaagct gctggaggga ggcaaggcaa     180
```

```
gctgctatgt gaaaaaacgc caggccaggc agtcatgtca cacctggcag aaatgactga    240
agcatagcca ctggctgaag ttatccccac acccactctc tggagaggat gatcaggagc    300
agtctgctca accgggaggt gggactcctc ctcgggaagg tgtagaatca ccagcctggc    360
tccctgcgga ctcccggggc tcacagaggc cagagcagca acagcacatg ggaaacaacg    420
gggcgctgga ctggggaggt ctcagagctc tcctagtgat gacagcctca ttttacccag    480
ggagaaaggg cgagtaagct aaggtcacac agcaacaaag ctgcacccag acccagagc    540 cactctcctc cctccctcct ccaccagggc catgcccact tggggcaccc cgccaccgtg    600
ttccagggac agctggagca catgcttctt ccctcgccaa cccagcaatt ccgcagggca    660
tctgacctcc actgttgact tctacccaga ggacaagaac atttttagtt cccaaggaat    720
gtacatcagc cccacggaag ctaggccacc tctgggatgg ggttgctggt ttagaacaaa    780
cgccagtcat cctatataag gacctgacag ccaccaggca ccacctccgc caggaactgc    840
aggcccacct gtctgcaacc cagctgaggc catgccctcc ccagggaccg tctgcagcct    900
cctgctcctc ggcatgctct ggctggactt ggccatggca ggctccagct tcctgagccc    960
tgaacaccag agagtccagc agagaaagga gtcgaagaag ccaccagcca agctgcagcc   1020
ccgagctcta gcaggctggc tccgcccgga agatggaggt caagcagaag ggcagagga   1080 tgaactggaa gtccggttca acgccccctt tgatgttgga atcaagctgt caggggttca   1140
gtaccagcag cacagccagg ccctggggaa gtttcttcag gacatcctct gggaagaggc   1200
caaagaggcc ccagccgaca gtgatcgcc cacaagcctt actcacctct ctctaagttt   1260
agaagcgctc atctggcttt tcgcttgctt ctgcagcaac tcccacgact gttgtacaag   1320
ctcaggaggc gaataaatgt tcaaactgta aaaaaaaaa aaaaaaaaa aaaa           1374
```

<210> SEQ ID NO 28
<211> LENGTH: 28
<212> TYPE: PRT
<213> ORGANISM: homo sapiens

<400> SEQUENCE: 28

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 167
<212> TYPE: PRT
<213> ORGANISM: homo sapiens

<400> SEQUENCE: 29

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

```
Ile Ser Asn Asp Leu Glu Asn Leu Arg Asp Leu Leu His Val Leu Ala
            100                 105                 110
Phe Ser Lys Ser Cys His Leu Pro Trp Ala Ser Gly Leu Glu Thr Leu
        115                 120                 125
Asp Ser Leu Gly Gly Val Leu Glu Ala Ser Gly Tyr Ser Thr Glu Val
    130                 135                 140
Val Ala Leu Ser Arg Leu Gln Gly Ser Leu Gln Asp Met Leu Trp Gln
145                 150                 155                 160
Leu Asp Leu Ser Pro Gly Cys
                165

<210> SEQ ID NO 30
<211> LENGTH: 3427
<212> TYPE: DNA
<213> ORGANISM: homo sapiens

<400> SEQUENCE: 30
```

| | | | | | |
|---|---|---|---|---|---|
| gtaggaatcg | cagcgccagc | ggttgcaagg | cccaagaagc | ccatcctggg | aaggaaaatg  60 |
| cattggggaa | ccctgtgcgg | attcttgtgg | ctttggccct | atcttttcta | tgtccaagct 120 |
| gtgcccatcc | aaaaagtcca | agatgacacc | aaaaccctca | tcaagacaat | tgtcaccagg 180 |
| atcaatgaca | tttcacacac | gcagtcagtc | tcctccaaac | agaaagtcac | cggtttggac 240 |
| ttcattcctg | gctccaccc | catcctgacc | ttatccaaga | tggaccagac | actggcagtc 300 |
| taccaacaga | tcctcaccag | tatgccttcc | agaaacgtga | tccaaatatc | caacgacctg 360 |
| gagaacctcc | gggatcttct | tcacgtgctg | gccttctcta | agagctgcca | cttgccctgg 420 |
| gccagtggcc | tggagacctt | ggacagcctg | ggggtgtcc | tggaagcttc | aggctactcc 480 |
| acagaggtgg | tggccctgag | caggctgcag | ggtctctgc | aggacatgct | gtggcagctg 540 |
| gacctcagcc | ctgggtgctg | aggccttgaa | ggtcactctt | cctgcaagga | ctacgttaag 600 |
| ggaaggaact | ctggcttcca | ggtatctcca | ggattgaaga | gcattgcatg | acaccccctt 660 |
| atccaggact | ctgtcaattt | ccctgactcc | tctaagccac | tcttccaaag | gcataagacc 720 |
| ctaagcctcc | ttttgcttga | aaccaaagat | atatacacag | gatcctattc | tcaccaggaa 780 |
| gggggtccac | ccagcaaaga | gtgggctgca | tctgggattc | ccaccaaggt | cttcagccat 840 |
| caacaagagt | tgtcttgtcc | cctcttgacc | catctccccc | tcactgaatg | cctcaatgtg 900 |
| accaggggtg | atttcagaga | gggcagaggg | gtaggcagag | cctttggatg | accagaacaa 960 |
| ggttccctct | gagaattcca | aggagttcca | tgaagaccac | atccacacac | gcaggaactc 1020 |
| ccagcaacac | aagctggaag | cacatgttta | tttattctgc | attttattct | ggatggattt 1080 |
| gaagcaaagc | accagcttct | ccaggctctt | tggggtcagc | cagggccagg | ggtctccctg 1140 |
| gagtgcagtt | tccaatccca | tagatgggtc | tggctgagct | gaacccattt | tgagtgactc 1200 |
| gagggttggg | ttcatctgag | caagagctgg | caaaggtggc | tctccagtta | gttctctcgt 1260 |
| aactggtttc | atttctactg | tgactgatgt | tacatcacag | tgtttgcaat | ggtgttgccc 1320 |
| tgagtggatc | tccaaggacc | aggttatttt | aaaaagattt | gttttgtcaa | gtgtcatatg 1380 |
| taggtgtctg | cacccagggg | tggggaatgt | ttgggcagaa | gggagaagga | tctagaatgt 1440 |
| gttttctgaa | taacatttgt | gtggtgggtt | ctttggaagg | agtgagatca | ttttcttatc 1500 |
| ttctgcaatt | gcttaggatg | ttttttcatga | aaatagctct | ttcagggggg | ttgtgaggcc 1560 |
| tggccaggca | cccctggag | agaagtttct | ggccctggct | gaccccaaag | agcctggaga 1620 |
| agctgatgct | ttgcttcaaa | tccatccaga | ataaaacgca | aagggctgaa | agccatttgt 1680 |

```
tggggcagtg gtaagctctg gctttctccg actgctaggg agtggtcttt cctatcatgg    1740
agtgacggtc ccacactggt gactgcgatc ttcagagcag gggtccttgg tgtgaccctc    1800
tgaatggtcc agggttgatc acactctggg tttattacat ggcagtgttc ctatttgggg    1860
cttgcatgcc aaattgtagt tcttgtctga ttggctcacc caagcaaggc caaaattacc    1920
aaaaatcttg gggggttttt actccagtgg tgaagaaaac tcctttagca ggtggtcctg    1980
agacctgaca agcactgcta ggcgagtgcc aggactcccc aggccaggcc accaggatgg    2040
cccttcccac tggaggtcac attcaggaag atgaagagg aggtttgggg tctgccacca    2100
tcctgctgct gtgttttttgc tatcacacag tgggtggtgg atctgtccaa ggaaacttga    2160
atcaaagcag ttaactttaa gactgagcac ctgcttcatg ctcagccctg actggtgcta    2220
taggctggag aagctcaccc aataaacatt aagattgagg cctgccctca gggatcttgc    2280
attcccagtg gtcaaaccgc actcacccat gtgccaaggt ggggtattta ccacagcagc    2340
tgaacagcca aatgcatggt gcagttgaca gcaggtggga aatggtatga gctgaggggg    2400
gccgtgccca ggggcccaca gggaaccctg cttgcacttt gtaacatgtt tacttttcag    2460
ggcatcttag cttctattat agccacatcc ctttgaaaca agataactga gaatttaaaa    2520
ataagaaaat acataagacc ataacagcca acaggtggca ggaccaggac tatagcccag    2580
gtcctctgat acccagagca ttacgtgagc caggtaatga gggactggaa ccagggagac    2640
cgagcgcttt ctggaaaaga ggagtttcga ggtagagttt gaaggaggtg agggatgtga    2700
attgcctgca gagagaagcc tgttttgttg gaaggtttgg tgtgtggaga tgcagaggta    2760
aaagtgtgag cagtgagtta cagcgagagg cagagaaaga agagacagga gggcaagggc    2820
catgctgaag ggaccttgaa gggtaaagaa gtttgatatt aaaggagtta agagtagcaa    2880
gttctagaga agaggctggt gctgtggcca gggtgagagc tgctctggaa aatgtgaccc    2940
agatcctcac aaccacctaa tcaggctgag gtgtcttaag ccttttgctc acaaaacctg    3000
gcacaatggc taattcccag agtgtgaaac ttcctaagta taaatggttg tctgtttttg    3060
taacttaaaa aaaaaaaaaa aagtttggcc gggtgcggtg gctcacgcct gtaatcccag    3120
cactttggga ggccaaggtg gggggatcac aaggtcacta gatggcgagc atcctggcca    3180
acatggtgaa accccgtctc tactaaaaac acaaaagtta gctgagcgtg gtggcgggcg    3240
cctgtagtcc cagccactcg ggaggctgag acaggagaat cgcttaaacc tgggaggcgg    3300
agagtacagt gagccaagat cgcgccactg cactccggcc tgatgacaga gcgagattcc    3360
gtcttaaaaa aaaaaaaaaa aagtttgtt tttaaaaaaa tctaaataaa ataactttgc    3420
cccctgc                                                              3427
```

METHOD TO REPRODUCE CIRCADIAN RHYTHMS ON A MICROFLUIDIC CHIP

RELATED APPLICATIONS

This application is a Continuation of PCT Patent Application No. PCT/IL2018/051404 filed on Dec. 27, 2018 which claims the benefit of priority 35 USC § 119(e) of U.S. Provisional Patent Application No. 62/611,034 filed Dec. 28, 2017. The contents of the above applications are all incorporated by reference as if fully set forth herein in their entirety.

The project leading to this application has received funding from the European Research Council (ERC) under the European Union's Horizon 2020 research and innovation programme (grant agreement No. [681870]).

SEQUENCE LISTING STATEMENT

The ASCII file, entitled 82867SequenceListing.txt, created on Jun. 19, 2020, comprising 51,198 bytes, submitted concurrently with the filing of this application is incorporated herein by reference.

FIELD AND BACKGROUND OF THE INVENTION

The present invention, in some embodiments thereof, relates to an in-vitro method of maintaining a sustainable circadian rhythm in cells of a cell culture and, more particularly, but not exclusively, to a system for inducing and maintaining a sustainable circadian rhythm in cells of a cell culture.

The liver is the largest internal organ in the human body, serving as the main site of carbohydrate, lipid and amino acid metabolism. Due to this metabolic activity, the liver is also the body's first line of defence, inactivating toxins and xenobiotics while clearing foreign particles from the blood. As the main organ responsible for metabolic homeostasis, the liver must respond quickly to changes in nutrition and hormonal signalling events, while at the same time anticipate changes in the energy requirements of the organism. This complex physiological response is controlled by fast processes, such as enzymatic cascades resolving in minutes, and slow processes such as transcriptional regulation and circadian rhythms occurring in hours.

Together these regulatory processes produce a dynamic shifting pattern of metabolic and transcriptional regulation that has thus far limited the ability to create efficient pharmaceutical interventions for a variety of metabolic diseases. This complexity is most distinct in the evaluation of drug metabolism and toxicity as physiological rhythms dramatically affect the expression of CYP450 enzymes, transporters, and metabolic pathways, affecting the ability to optimize pharmaceutical interventions or properly assess the chronic effects of drugs or toxins.

The earth's rotation causes a day and night cycle of about 24 hours. This introduces cyclic differences in illumination, temperature, and subsequent availability of metabolites. To adapt and anticipate these changes, organisms from all kingdoms have developed internal circadian clocks, operating on the cellular and whole organism levels, synchronized by external triggers including light, temperature, oxygen concentration and food intake. These rhythms enable organisms to anticipate the environmental changes around them and to prepare for them, increasing the efficacy of energy exploitation. Interestingly, a significant part of the cellular machine is invested in circadian rhythms: about 3-20% of the mammalian transcriptome oscillates in a 24 hours-cycle, with a large proportion of genes involved in metabolism, 6%-20% of the proteome in the liver exhibits circadian cycle, predominantly clustering into metabolic pathways and roughly 60% of the metabolome is subjected to circadian-related accumulation patterns. Disruption of the circadian rhythm, in cases of night shift-work, frequent time-zone change or by insufficient sleep, extensive nocturnal feeding, high-fat diet and long-term alcohol intake is strongly associated with obesity and type 2 diabetes increasing the symptoms occurrence by 20% to 50%. In humans, polymorphism in core clock components is linked to 40-80% higher risk for metabolic disorders. Altogether, these metabolic disorders cluster under the definition of metabolic syndrome, an emerging pandemic with estimated prevalence of 15 to 30% among non-diabetic populations around the world. With annual costs reaching up to $100-200 billion in the US alone, there is great need to establish reliable human circadian models to enable study of these metabolic diseases. Such platforms would enable screening for novel therapeutics for metabolic disorders.

Circadian rhythms affect liver metabolism and are primarily studied in animal models using end-point assays providing little dynamic information. While real-time luciferase recording offers exciting new insights into transcriptional dynamics, it provides little metabolic information and is difficult to manipulate. In contrast, primary cells can be readily manipulated but rhythms rapidly decay post-synchronization.

With the growing evidence for reciprocal interaction between metabolism and the circadian clock, the circadian-metabolic axis shape most, if not all, of the liver's functions. For instance, during the waking period of the cycle, the liver upregulates pathways of glucose utilizations in order to produce energy, while increasing amino acid processing and ammonia production. During the fasting-sleep period, gluconeogenesis is upregulated. Importantly, drug metabolism also exhibits day-night oscillation, suggesting time-dependent toxicity termed chronotoxicity as seen for instance when administering the anti-asthmatic drug Theophylline, that is metabolized by CYP1A2 enzyme in the liver, at different times of the day. It is worth noting that 20%-50% of circadian-cycling gene expression is regulated post transcriptionally or post translationally rather than on the mRNA level while about 80% of mRNA transcript oscillation is not dependent on transcription. In order to have a basic understanding of this circadian-metabolic axis, a reliable human liver model, subjected to circadian oscillation, is surly needed.

A major part of the understanding of the circadian rhythms, on all levels, transcription, translation and metabolism, is based on rodents and other model organisms. While laboratory rodent models are very informative, extrapolation of metabolic data to humans is somewhat challenging, due to differences in physiology, including different microbiome populations, signal transduction cascades, transport and circulation, different gene repertoire and often inverted circadian rhythm. Human in vitro models on the other hand, have similar limitations, although cell lines share human genetics, cell cultures are usually static, thus lacking critical physiological features such as the routine fluctuations of metabolite levels due to meals, and the circadian changes in hormonal cues and temperature. Moreover, cell lines exhibit Warburg-effect metabolism, they are highly glycolytic—consuming more glucose and producing more lactate with lower oxygen consumption, while not performing hepatocellular core functions, including oxidative-phosphorylation (less than 10% compared to primary human hepatocytes (PHH)), ureagenesis (about 7% compared to PHH) and drug metabolism (less than 2% compared to PHH). Thus, the demand for a metabolically accurate human liver model yet stands.

The problem stems from an incomplete understanding of metabolic regulation and the lack of efficient engineering and computational tools with which to unravel its complexity. In fact, current reliance on end-point assays and animal studies limit the ability to manipulate conditions or gain pertinent information on fast events, while in vitro models of hepatocytes show little metabolic function and lack physiological complexity. This problem is compounded by failure of murine models to predict human response due to differences in physiology, metabolic regulation, and inverted day/night cycles. Therefore, there is a pressing need to develop metabolically functional models that mimic human physiological complexity and are capable of tracking transcriptional and metabolic dynamics, creating human-relevant models that go far beyond animal studies[4].

Recently, the present inventor's research group developed microfluidic Liver-on-Chip platforms that support the long-term culture of primary human hepatocytes in self-assembled liver organoids (Prill S, et al., et al., 2016. Arch Toxicol. 90(5):1181-91). Stable gradients mimic the development of liver zonation, while embedded nanosensors permit precise measurement of oxygen uptake rates in real-time. Using off-chip electrochemical monitoring of glucose and lactate the present inventor was recently able to show real-time shifts from mitochondrial respiration to glycolysis (Bavli D, et al., Proc Natl Acad Sci USA. 2016, 113(16):E2231-40).

Recent work showed a rhythmic accumulation of lipids in the mouse liver (Adamovich Y et al., Cell Metab. 2014, 19(2):319-30). Intracellular lipid accumulation, called Steatosis, together with bile accumulation, called cholestasis, apoptosis, necrosis and fibrosis are toxicological end-points currently evaluated post-hoc using fluorescent or histological staining.

Gagliano Onelia (2015) *Development of a "lab on a chip" platform for studying the control of the circadian clock by metabolic cycles*. [Ph.D. thesis not accessible until 1 Jan. 2018] developed an in vitro model that resembles the cyclic dynamic fluctuations that can be correlated to the pertinent biological networks for dissecting the effects the metabolism on circadian clock.

Yamada R. G., 2011 (Proceedings of 2011 International Conference on Microtechnologies in Medicine and Biology Lucerne, Switzerland, 4-6 May, 2011) discloses a process to fabricate a microfluidic perfusion cell-culture chamber for adherent mammalian cells and live imaging.

Kanada G. N., et al., 2013 (The 17th International Conference on Miniaturized Systems for Chemistry and Life Sciences 27-31 Oct. 2013) disclose a perfusion platform for the long-term culture of tissue explants, such as brain slices, by incorporating a commonly-used porous membrane a "culture insert" (hydrophilic PTFE) into polydimethylsiloxane (PDMS). The activity of the brain slices of suprachiasmatic nucleus (SCN) from newborn mice in which a clock gene (Period2) was fused with a luciferase gene was monitored by bioluminescence under supplementation of luciferin in the culture media.

SUMMARY OF THE INVENTION

According to an aspect of some embodiments of the present invention there is provided an in-vitro method of sustaining a synchronized circadian rhythm in cells of a cell culture, the method comprising: exposing the cells to a continuous flow of medium and to at least two stimuli provided in an oscillating manner with a periodicity of 24±4 hours, wherein a first stimulus and a second stimulus of the at least two stimuli are distinct, wherein the first stimulus is provided in a first time period and reaches a first peak in a first peak time period, and wherein a second stimulus is provided in a second time period and reaches a second peak in a second peak time period, and wherein an interval between end of time period of the first peak and beginning of the time period of the second peak is at least about 2 hours, thereby sustaining the synchronized circadian rhythm in the cells of the cell culture.

According to an aspect of some embodiments of the present invention there is provided a system for sustaining a synchronized circadian rhythm in cells of a cell culture, the system comprising: a fluidic device having culture wells for holding the cells, a plurality of inlets for receiving the first hormone, the second hormone, and a base culture medium, and a plurality of fluidic channels for establishing fluid communication between the inlets and the wells; a controller having a circuit configured for executing the method according to some embodiments of the invention.

According to some embodiments of the invention, the continuous flow of medium is provided at a constant rate.

According to some embodiments of the invention, the first stimulus is selected from the group consisting of: a first hormone or an analogue thereof, a first temperature, and a first gas.

According to some embodiments of the invention, the second stimulus is selected from the group consisting of: a second hormone or an analogue thereof, a second temperature and a second gas.

According to some embodiments of the invention, the duration of the time period of the first peak is at least about 1 minute and no more than about 6 hours.

According to some embodiments of the invention, the duration of the time period of the second peak is at least about 1 second and no more than about 4 hours.

According to some embodiments of the invention, the interval between end of the time period of the first peak and beginning of the time period of the second peak is no more than about 6 hours.

According to some embodiments of the invention, the duration of the first time period is at least about 30 minutes and no more than about 24 hours.

According to some embodiments of the invention, the in duration of the second time period is at least about 10 seconds and no more than about 6 hours.

According to some embodiments of the invention, the second stimulus is absent or present below the predetermined level in the time period of the first peak.

According to some embodiments of the invention, the at least first stimulus is absent or present below the predetermined level in the time period of the second peak.

According to some embodiments of the invention, the first hormone is selected from the group consisting of: cortisol, testosterone, adiponectin, insulin, thyroxine (T4), and fibroblast growth factor 21 (FGF21).

According to some embodiments of the invention, the analogue of the first hormone is a small molecule.

According to some embodiments of the invention, the second hormone is selected from the group consisting of: melatonin, growth hormone, Triiodothyronine (T3), ghrelin, prolactin, TSH, vasopressin, and leptin.

According to some embodiments of the invention, the analogue of the second hormone is a small molecule.

According to some embodiments of the invention, the first temperature is lower in about 1 Celsius degree as compared to the second temperature.

According to some embodiments of the invention, the cortisol is hydrocortisone.

According to some embodiments of the invention, the hydrocortisone is provided at a concentration range of about 0.2-15 μg/mL.

According to some embodiments of the invention, the cortisol is provided at a concentration of about 7.5 μg/mL.

According to some embodiments of the invention, the cortisol is dexamethasone.

According to some embodiments of the invention, the dexamethasone is provided at a concentration of about 0.01 to 200 μM.

According to some embodiments of the invention, the dexamethasone is provided at a concentration of about 100 μM.

According to some embodiments of the invention, the melatonin is provided at a concentration range of 0.001-2 mM.

According to some embodiments of the invention, the melatonin is provided at a concentration of about 200 μM.

According to some embodiments of the invention, the growth hormone is provided at a concentration range of 0.001-100 ng/ml.

According to some embodiments of the invention, the growth hormone is provided at a concentration of about 30 ng/ml.

According to some embodiments of the invention, the Triiodothyronine (T3) is provided at a concentration range of 0.01 nM-10 nM.

According to some embodiments of the invention, the Triiodothyronine (T3) is provided at a concentration range of about 10 nM.

According to some embodiments of the invention, the first temperature is about 36.5° C.

According to some embodiments of the invention, the cells are characterized by a synchronized metabolic activity no later than within 72 hours after being exposed to the at least two stimuli.

According to some embodiments of the invention, the cells are comprised in an organoid.

According to some embodiments of the invention, the organoid comprises hepatic cells and endothelial cells.

According to some embodiments of the invention, the organoid further comprises fibroblasts.

According to some embodiments of the invention, the organoid comprises enterocytes.

According to some embodiments of the invention, the organoid further comprises endothelial cells.

According to some embodiments of the invention, the organoid comprises cardiomyocytes and endothelial cells.

According to some embodiments of the invention, the cardiomyocytes are obtainable by differentiation of induced pluripotent stem cells.

According to some embodiments of the invention, the organoid comprises neural progenitor cells and endothelial cells.

According to some embodiments of the invention, the neural progenitor cells are obtainable by differentiation of induced pluripotent stem cells.

According to some embodiments of the invention, the organoid comprises renal cells.

According to some embodiments of the invention, the renal cells comprise primary human proximal tubular cells.

According to some embodiments of the invention, the renal cells comprise HK2 proximal tubular cells.

According to some embodiments of the invention, the cells form part of an isolated tissue in a cell culture.

According to some embodiments of the invention, the cells are human cells.

According to some embodiments of the invention, the hormones and the base culture medium are delivered directly to the culture wells to be mixed therein.

According to some embodiments of the invention, the system further comprising a mixing chamber for receiving and mixing the hormones and the base culture medium to provide the medium, wherein a portion of the fluidic channels is constituted for delivering the medium to the culture wells.

According to some embodiments of the invention, the flow of the medium is provided in a single path.

According to some embodiments of the invention, the flow of the medium is provided in a closed circuit.

According to some embodiments of the invention, each well in the fluidic device is characterized by a width of from about 1 mm to about 1.8 mm, and a height of from about 0.4 mm to about 0.8 mm.

According to some embodiments of the invention, each of the wells comprises a matrix for culturing the cells thereon.

According to some embodiments of the invention, the matrix is in a form of gel.

According to some embodiments of the invention, the matrix comprises collagen.

According to some embodiments of the invention, the matrix comprises of basement membrane gel.

According to some embodiments of the invention, the basement membrane gel is Matrigel® (e.g., from Becton Dickinson, USA).

According to some embodiments of the invention, the system further comprising a positive displacement pump or pressure, wherein the controller is configured to control the flow rate of the medium by controlling the fluid displacement or fluid pressure.

According to some embodiments of the invention, the system further comprising a temperature control system configured for receiving control signals from the controller and for oscillating a temperature of the medium responsively to the control signals.

According to some embodiments of the invention, the controller is configured for signalizing the temperature control system to oscillate a first temperature and a second temperature of the medium during said first and said second time periods, respectively.

According to some embodiments of the invention, the first temperature is lower by about 1 degree centigrade than the second temperature.

According to some embodiments of the invention, the controller is configured to vary relative amounts of said hormones and said base culture medium within said medium, while maintaining said constant flow of said medium.

According to some embodiments of the invention, each of the first stimulus or the second stimulus occurs once during said 24±4 hours.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
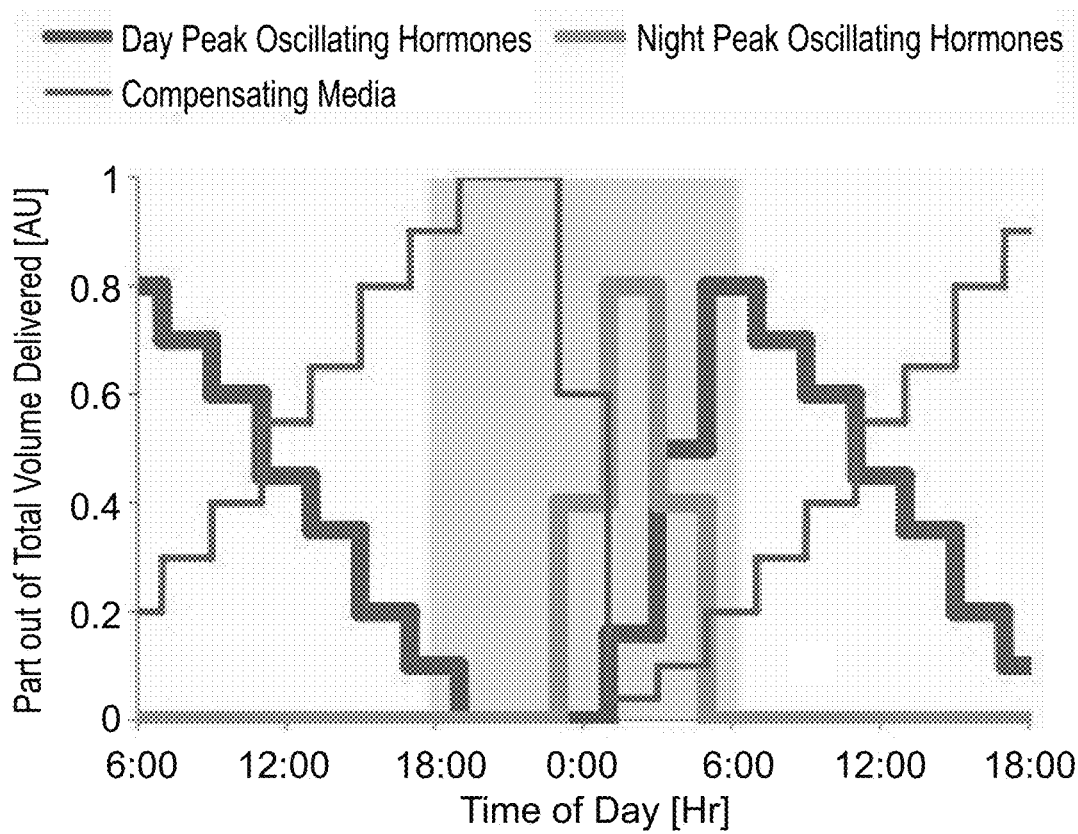
Figure 1B:
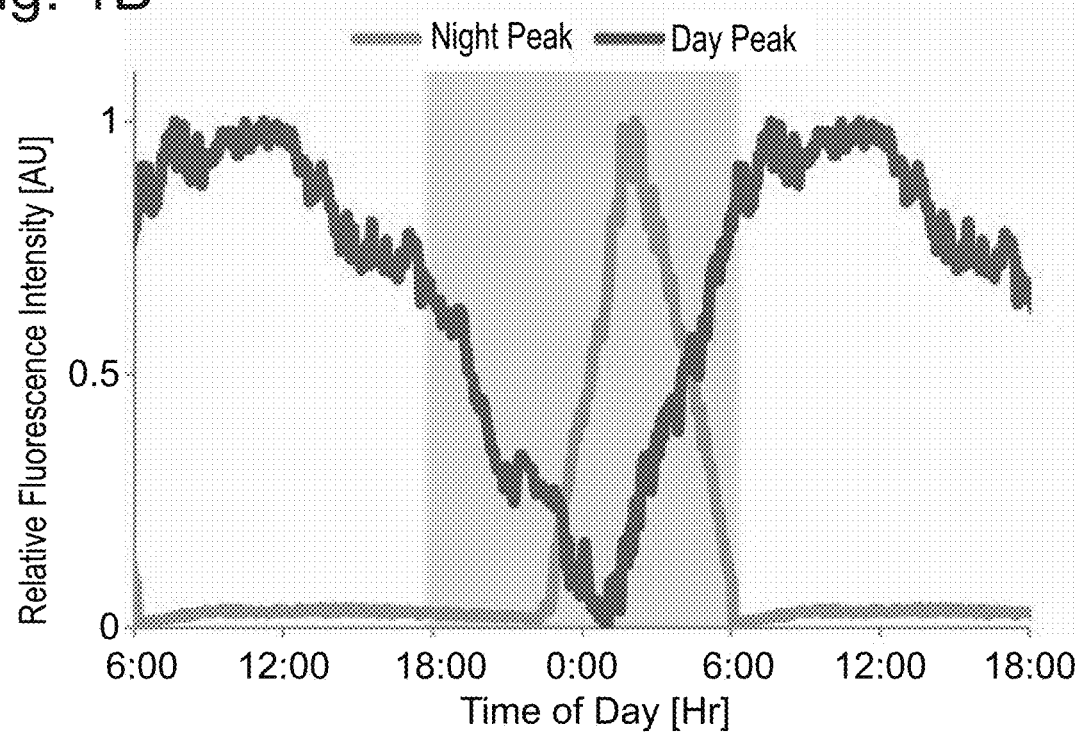

FIGS. 1A-B—Establishment of a robust circadian-like flow pattern. FIG. 1A—Flow routine design recapitulating circadian oscillation in concentration of "day" (red) and "night" (green) entraining factors. FIG. 1B—Fluorescence of Rhodamine B and FITC solutions, delivered according to the designed flow routine, resembling "day" (red) and "night" (green) entraining factors, respectively. Gray areas represent dark half of the day, i.e. night-time.

FIGS. 2A-D—Organoid-on-a-chip microfluidic platform. FIG. 2A—Explosive view of a single bioreactor component. From bottom to top: ULTEM™ housing, laser-cut PDMS microwells with cover glass bottom, an O-ring for sealing, and ULTEM™ top cover with a glass window (left). Phase micrograph of an organoid, consisting of a co-culture of Upcyte® Hepatocytes with RCEC, inside a microwell (right). Scale bar 200 μm. FIG. 2B—Photo of a single assembled bioreactor. FIG. 2C—Photo of an assembled multi-bioreactor platform for higher throughput. FIG. 2D—Photo of a three-input bioreactor connected to the FLUIGENT flow control system and the IST AG LV5 sampling sensor. From top to bottom: Air flow control system, liquid reservoirs on the right, flowmeter control unit on the left, flowmeters, each per reservoir, three-input mixer connected to input the bioreactor on the left and the IST AG LV5 sensor on the right, connected to the bioreactor outflow.

Figure 3C:
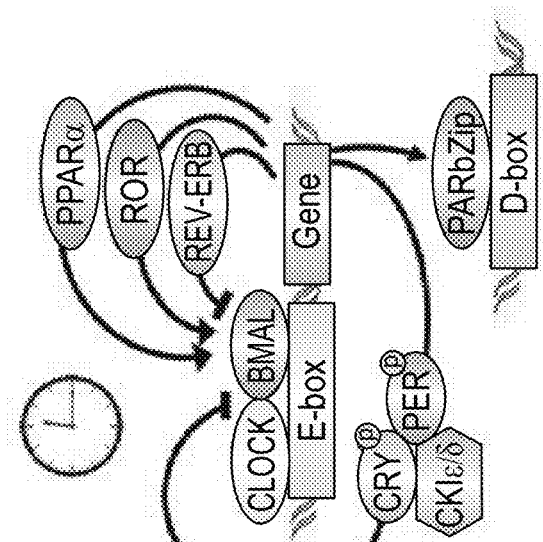
Figure 3B:
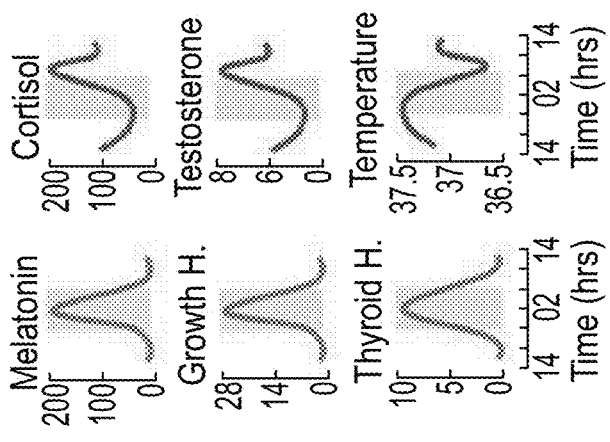
Figure 3E:
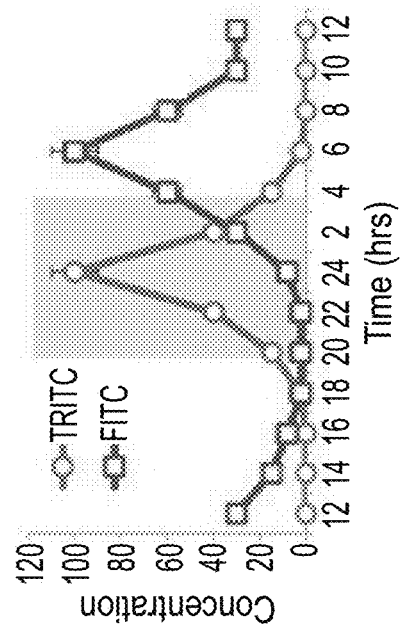
Figure 3A:
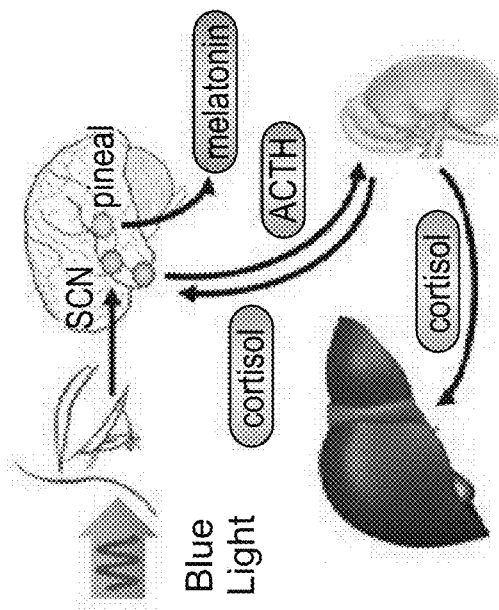
Figure 3D:
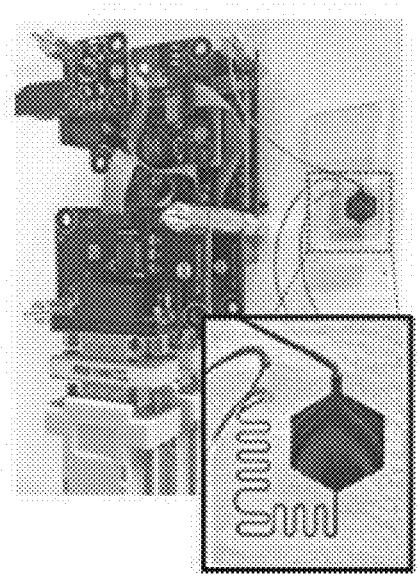

FIGS. 3A-E—FIG. 3A—Schematic suprachiasmatic nucleus (SCN) control of hormone oscillation. Blue light is detected by the retina which signals the SCN of the beginning of the day. In response the SCN signals other brain regions including the pituitary that responds by releasing adrenocorticotropic hormone (ACTH). ACTH stimulates the adrenal gland to secret cortisol. Cortisol in turn entrains all the other peripheral clocks, including the liver, synchronizing them to the day phase of the cycle. In the absence of blue light SCN interaction with the pineal gland triggers the release of melatonin, synchronizing the peripheral clocks to the night phase. FIG. 3B—Representative physiological and endocrine cycles in human plasma. FIG. 3C—Schematic of the canonical transcriptional feedback loop controlling the cell-autonomous clock. FIG. 3D—Computer controlled microfluidics can mimic the complex dynamics of hormonal and temperature oscillation. FIG. 3E—Oscillation of markers mimicking the two types of in vivo kinetics seen in FIG. 3B.

FIGS. 4A-E—FIG. 4A—Micro-well bioreactor permits cell seeding in an open configuration. FIG. 4B—Microwells cause rapid overnight assembly of liver organoids. FIG. 4C—Fluorescence image liver organoid on Day 22 of culture composed of hepatocytes (Green, Albumin), endothelial cells (Red, CD31), basement membrane laminin (Blue) and fibroblasts (unmarked). FIG. 4D—Continuous real-time measurement of oxygen uptake using embedded nanosensors show 20 days stability. FIG. 4E—qRT-PCR (quantitative reverse-transcription polymerase chain reaction) expression analysis shows that primary hepatocytes co-cultured in 3D for 22 days in bioreactor show similar expression pattern to freshly isolated hepatocytes.

Figure 5:
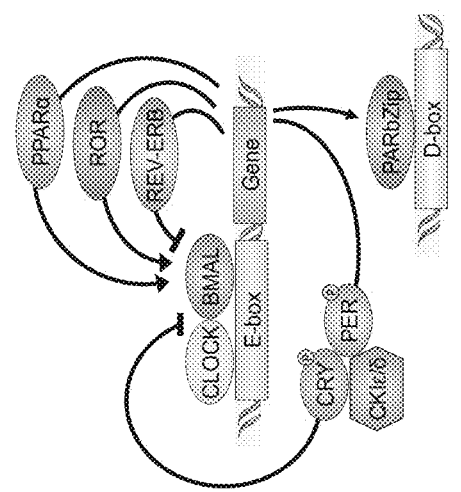

FIG. 5—Schematic of the canonical transcriptional feedback loop controlling the cell-autonomous clock.

Figure 6:
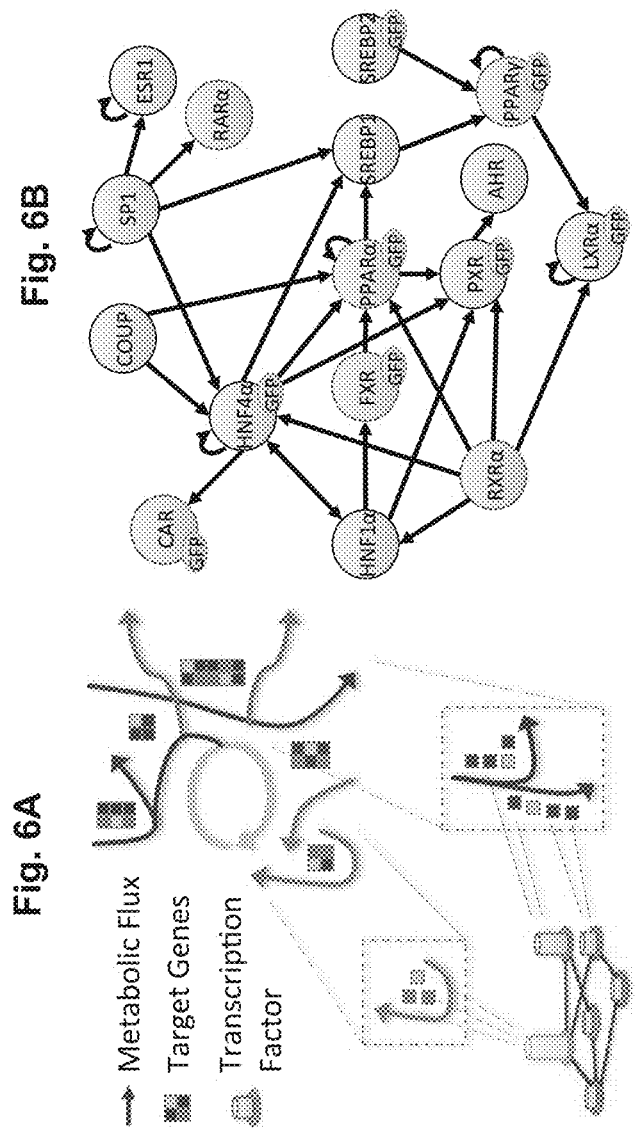

FIGS. 6A-B—FIG. 6A is a schematic depicting transcriptional regulatory control of the metabolic network. FIG. 6B—Transcriptional regulatory network derived from computational analysis of primary human hepatocytes. Transcription factors highlighted in red show rhythmic expression pattern in mice. Green tags mark factors for which the present inventor has developed GFP activity reporters. Surprisingly, expression of HNF4α and LXRα does not appear to oscillate, although their activity might.

Figure 7:
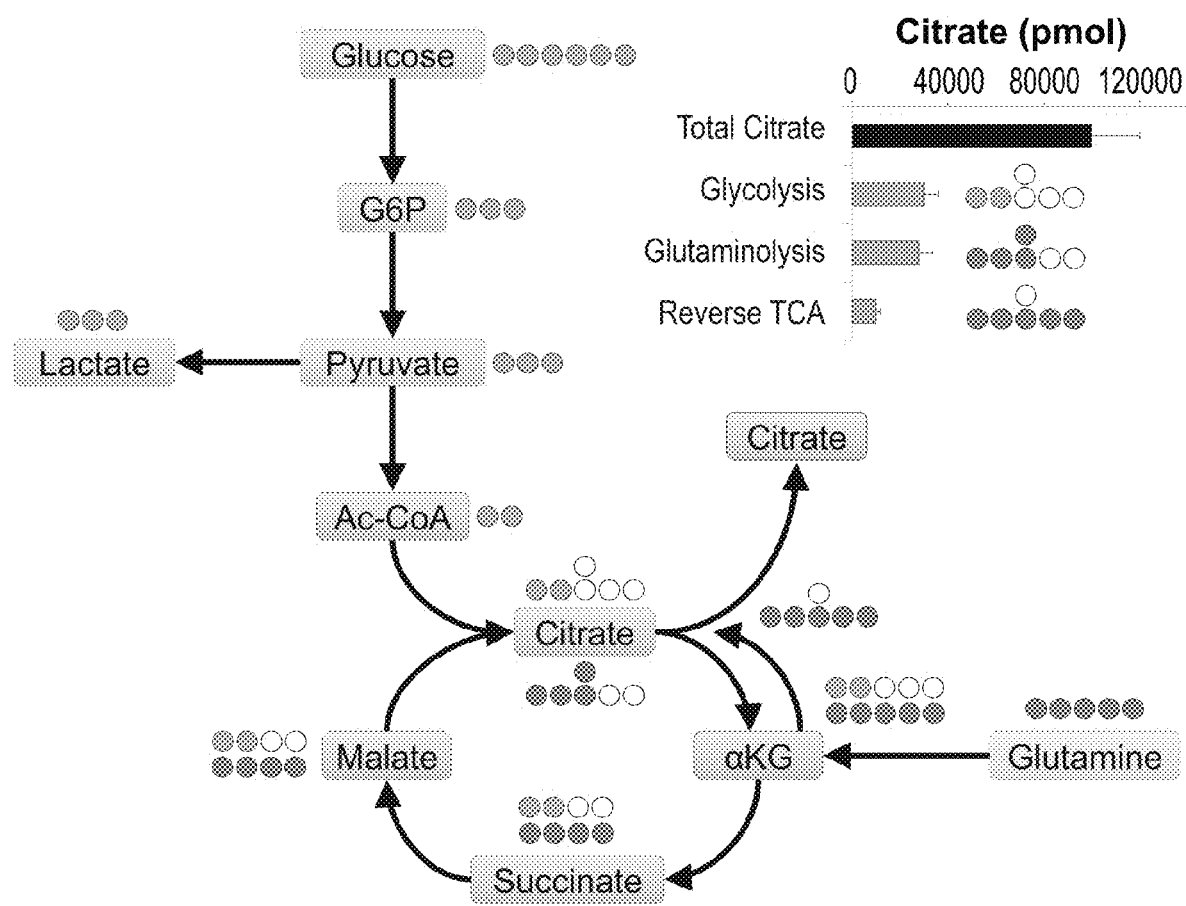

FIG. 7—Schematic of central carbon metabolism, glycolysis and glutaminolysis. Full circles mark $^{13}C$-labeled carbons. Green circles note glutamine source, while orange circles note glucose source. Citrate is rhythmically secreted from hepatocytes, providing non-invasive signature of metabolism.

FIGS. 8A-C—FIG. 8A—Phase and immunofluorescence image of organoids composed of human hepatocytes (albumin, green), endothelial cells (CD31, red), and pericytes (not coloured). FIG. 8B—Albumin production dynamic of human hepatocytes cultured alone (black), 3D hepatocyte spheroids on Matrigel® (red, circles), and 3D organoids (green, squares). Human organoids maintain function for over 45 days in vitro. The dotted blue line marks in vivo levels of secretion (positive control). FIG. 8C—qRT-PCR analysis of albumin (ALB), CYP3A4, and HNF4A on Day 40 of culture. Organoids maintain expression of all three genes.

FIGS. 9A-C—FIG. 9A—Schematics of non-specific absorption and clearance unintentionally created in standard tissue culture. FIG. 9B—Constant perfusion saturates absorption sites permitting precise concentration control. FIG. 9C—Polydimethylsiloxane (PDMS) microfluidic chip containing a two-inlet mixer and a central chamber. Oscillating the input between red and blue food colours creates stimulation waves seen in the main chamber moving from left to right without changing the flow rate.

FIGS. 10A-E—FIG. 10A—Polymethylmethacrylate (PMMA) bioreactor on Ziess LSM700 confocal microscope. FIG. 10B—Diameter of the micro-wells leads to rapid assembly of organoids composed of hepatocytes, endothelial cells and pericytes. Organoid shows complex structures after 22 days in vitro. FIG. 10C—Albumin and ApoB100 secretion measured by ELISA in outflow show stabilization and maintained of function for 26 days. FIG. 10D—Finite element model using COMSOL shows low shear distribution and equal oxygen supply per well. FIG. 10E—Oxygen gradient forms due to consumption mimicking the in vivo sinusoid microenvironment.

FIGS. 11A-E—FIG. 11A—System schematic. FIG. 11B—Oxygen-quenched decay causes phase shift between the intensity-modulated excitation and emission light. Two-superimposed frequencies were used to screen out background interference. FIG. 11C—Fluorescence image of HepG2/C3A cells and sensor particles after immobilization in a collagen matrix. FIG. 11D—Fluorescence intensity is rapidly lost away from the plane of focus, while phase shift measurements are unaffected. FIG. 11E—Oxygen uptake over time response of HepG2/C3A cells exposed to acetaminophen. Left graph: An immediate dose-dependent loss of oxygen uptake concludes in 60 min, while a slow dose-independent loss of oxygen uptake terminates with total cell death within 3 to 5 days. Top right graph: Dose dependence of acetaminophen after 12 hours. $TC_{50}$ was calculated to be 12.3 mM. No effect is observed at 4 mM acetaminophen at 12 hours (blue arrow). Bottom right graph: Temporal close up shows a transient loss of mitochondrial respiration at 1 and 4 mM acetaminophen, below threshold at which cell death could be detected.

FIGS. 12A-J—FIG. 12A—Schematic of genetic mechanism; FIG. 12B—qRT-PCR analysis shows 300-fold induction of IL6ST. FIG. 12C—Oncostatin m (OSM) stimulation is required to expand cells through Jak-STAT3. FIG. 12D—Epithelial-to-mesenchymal transition (EMT) is blocked using U0126 a MEK1/2 inhibitor. FIGS. 12E-F—Phase (FIG. 12E) and fluorescence (FIG. 12F) images show polarization of E6/E7 hepatocytes in culture. FIG. 12G—Functional assays and testosterone clearance show that CYP450 activity in E6/E7 hepatocytes is not different from primary human hepatocytes (PHH). FIG. 12H—CYP3A4 activity, and induction by 20 μM of the PXR agonist rifampicin (RIF), is stable up to population doubling 42. FIG. 12I—qRT-PCR analysis shows strong expression of metabolically important nuclear receptors, enzymes and transporters on population doubling 25. FIG. 12J—Rhythmic expression of PER2 and CRY in response to serum-shock is shown.

FIGS. 13A-C—FIG. 13A—$TC_{50}$ values for 12 compounds known to cause hepatic damage through apoptosis, cholestasis (bile accumulation) or steatosis (lipid accumulation). FIGS. 13B and 13C—Fluorescence staining (FIG. 13B) and quantification (FIG. 13C) of toxicological endpoints in differentiated hepatocytes. Loss of bile acid production (cholestasis) was evaluated by 5(6)-carboxy-2',7'-dichlorofluorescein diacetate (CDFDA) staining, lipid accumulation (steatosis) by Nile red staining, and apoptosis by TUNEL labelling.

Figure 14:
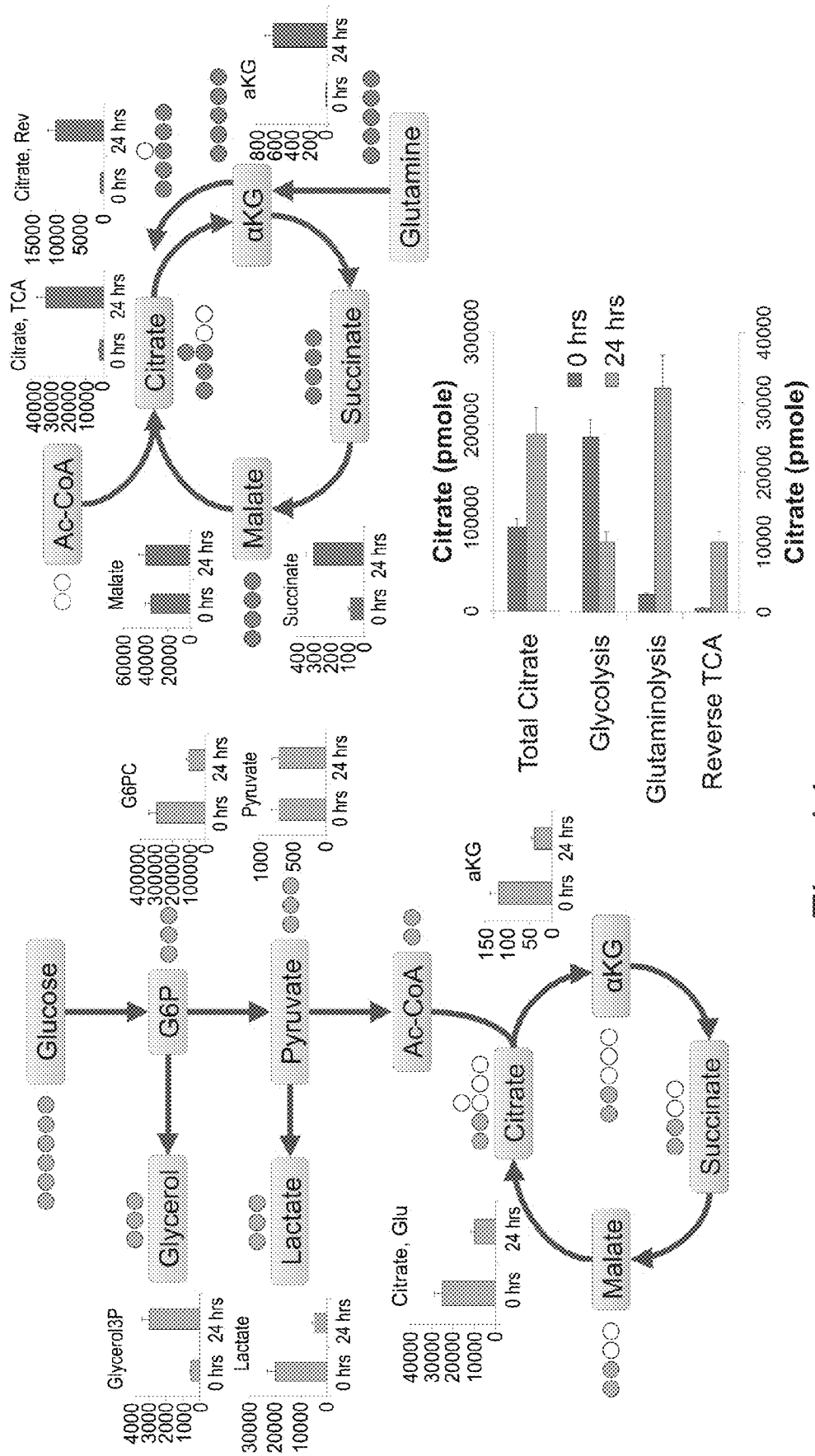

FIG. 14—Schematic representation of metabolic fluxes and incorporation of $^{13}C$ to each metabolite following 15 minutes pulse of 25 mM glucose or 4 mM glutamine $^{13}C$. Red and green arrows marks down- and up-regulated fluxes after 24 hours of differentiation, respectively. Changes in metabolic fluxes reflected in citrate $^{13}C$ incorporation pattern.

Figure 15:
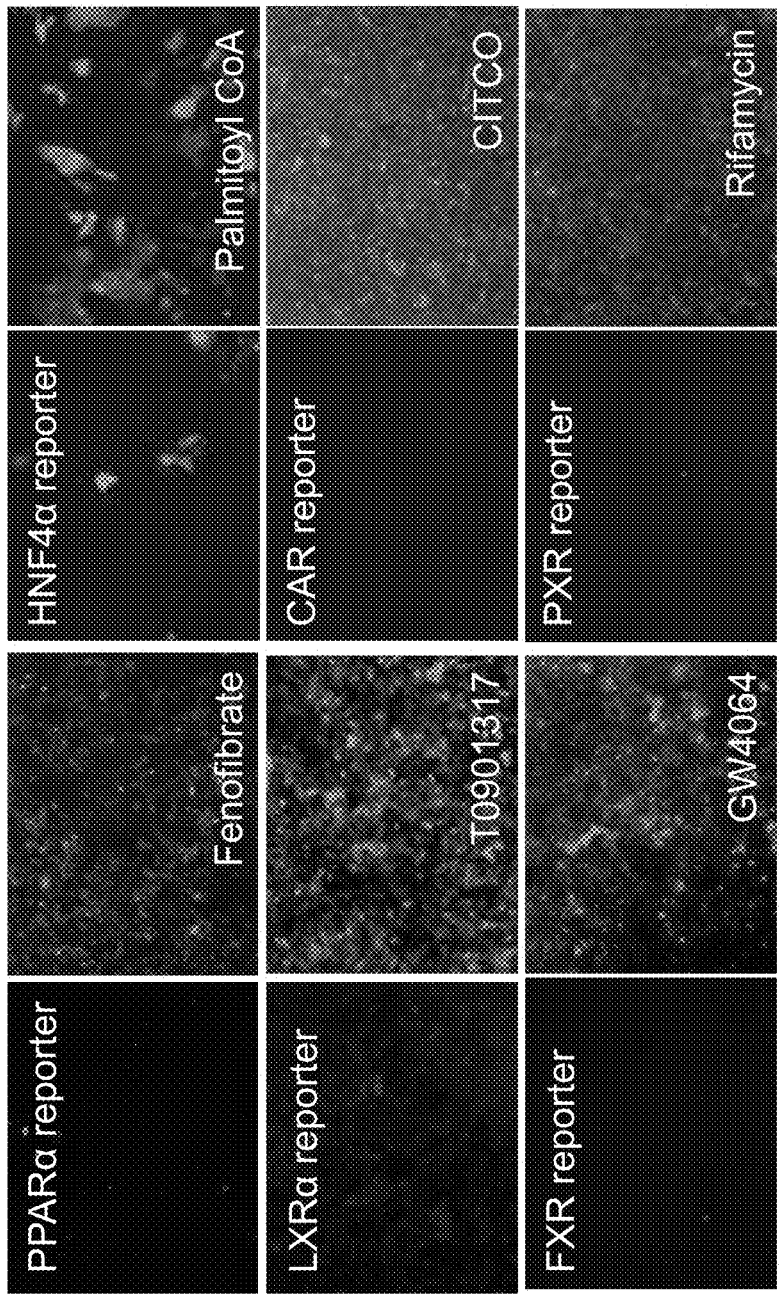

FIG. 15—GFP reporters for nuclear receptors stably expressed in Huh7 cells using lentivirus transfection. Cells were exposed to classical agonists 72 hours post transfection.

Figure 16A:
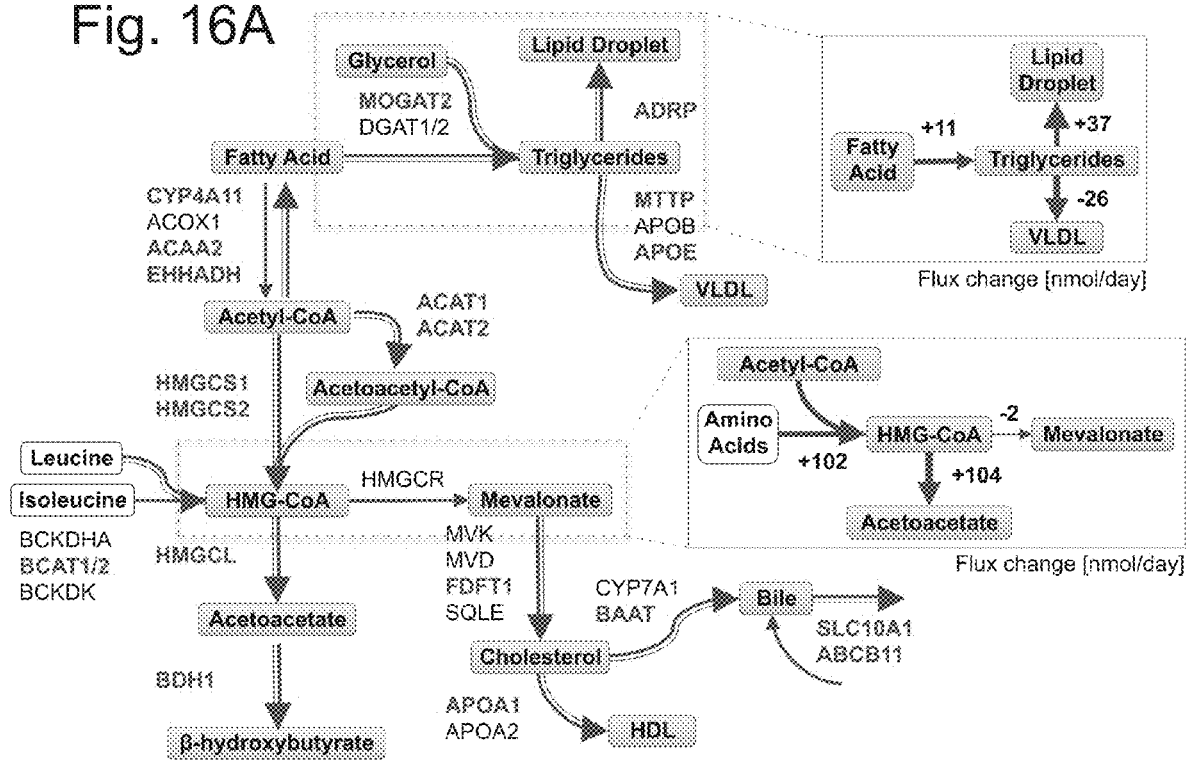
Figure 16B:
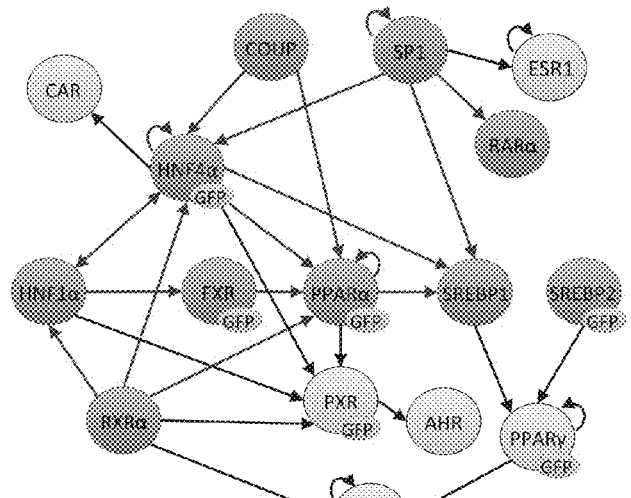
Figure 16C:
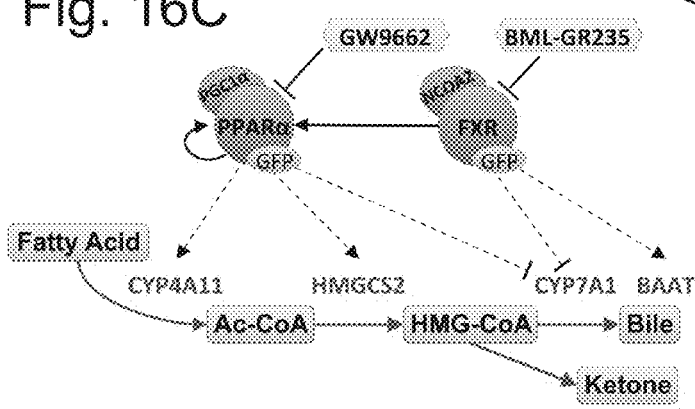
Figure 16D:
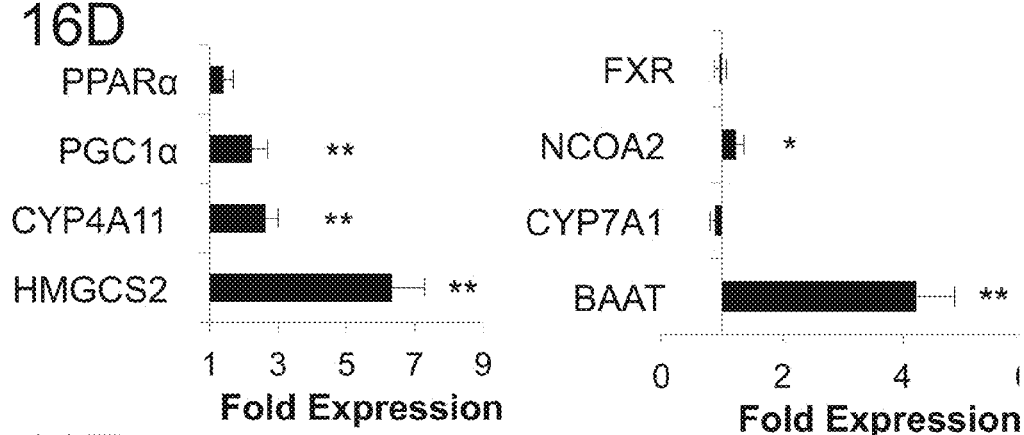
Figure 16E:
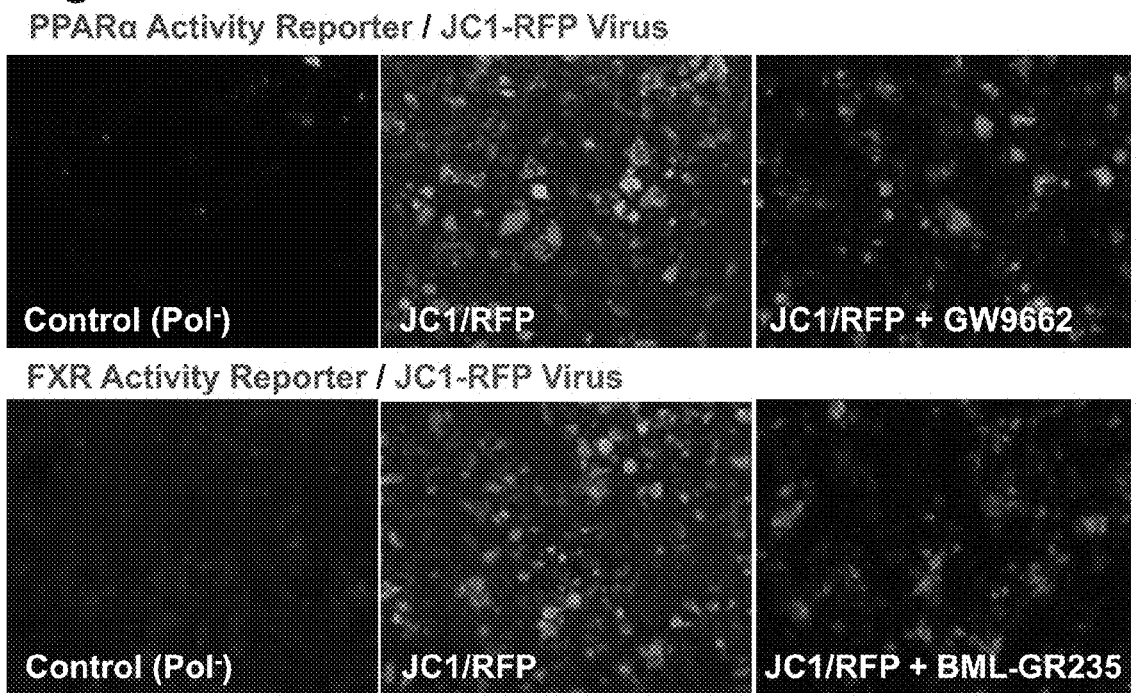
Figure 16F:
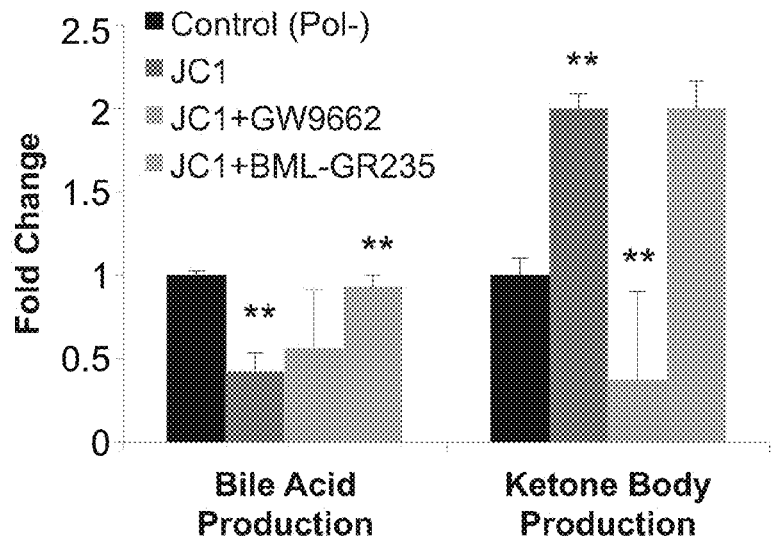

FIGS. 16A-F—FIG. 16A—Metabolic fluxes superimposed with gene expression patterns of lipid metabolism induced by HCV-infection of primary human hepatocytes. Fluxes were measured by direct metabolomics; gene expression was measured by Affymetrix array. FIG. 16B—Transcriptional regulatory analysis highlights nuclear receptors whose target genes were differentially regulated in lipid metabolism. FIGS. 16C-D—Computational analysis and qRT-PCR confirm the connectivity between the regulators and the affected metabolic genes. FIG. 16E—GFP reporters (as in FIG. 15) used to validate the activation of PPAR and FXR. FIG. 16F—Pharmaceutical inhibition of regulators reverses the affected metabolic flux.

Figures 17A, 17B:
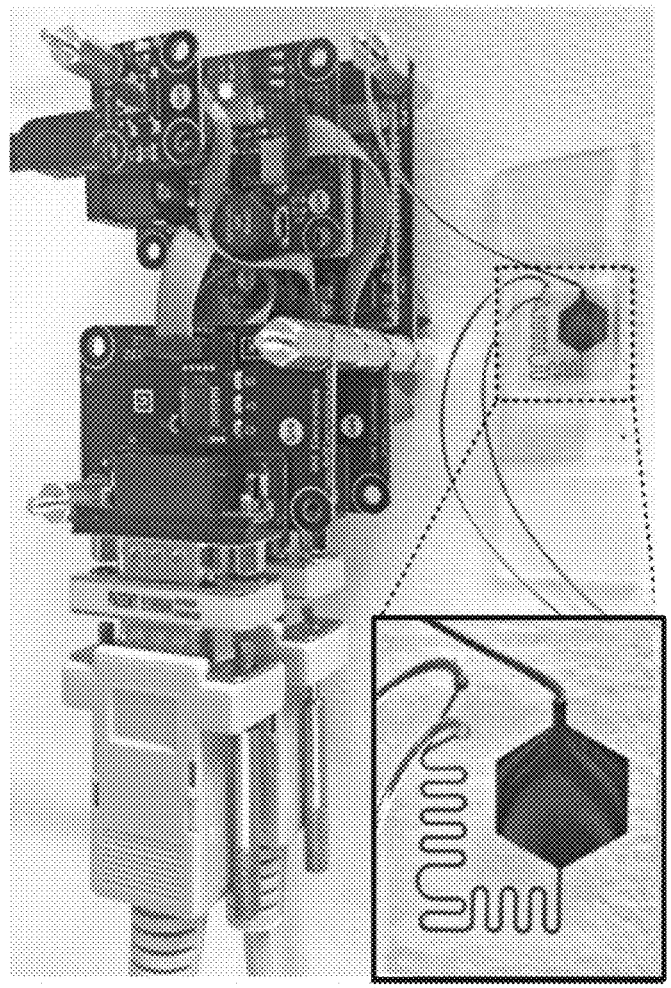

FIGS. 17A-B depict use of high fluid resistance microfluidic chip for mixing one and two phase signal. FIG. 17A—Microcontroller connected to syringe pumps pushing blue and red fluids in oscillatory pattern in microfluidic device. FIG. 17B—Microchip connected to Fluigent, pressure driven controller pushing green, blue and red fluids in oscillatory pattern in microfluidic device. Food color dyes used here for visualization.

FIGS. 18A-C depict open configuration microwell bioreactor used for long-term culture of human organoids for liver, heart, and brain microtissues. FIG. 18A—Explosive view schematic of the plastic manifold (brown) and the disposable microwell array it holds (grey). Tissue self assemble inside each well (dashed insert). FIG. 18B—Photograph of closed bioreactor. FIG. 18C—Multi-bioreactor system configured as a standard 6-well plate.

Figure 19A:
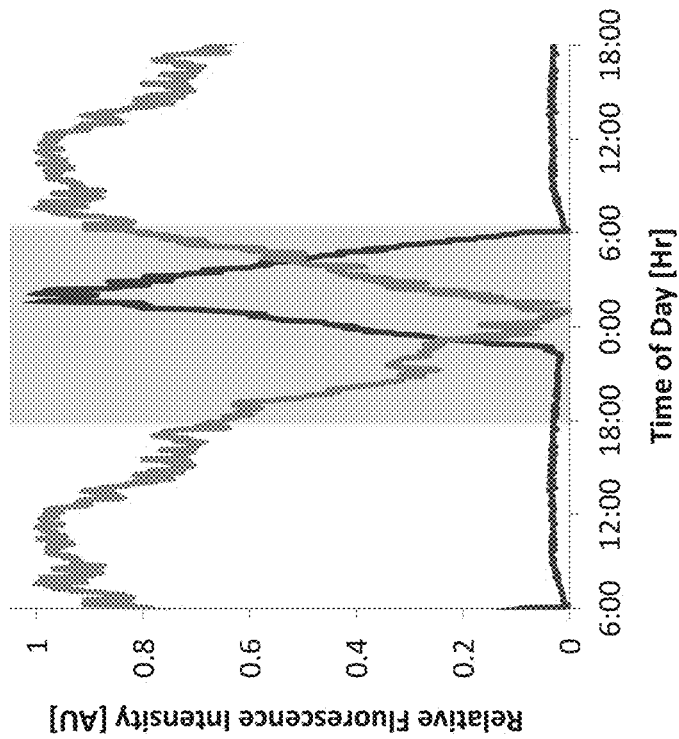
Figure 19B:
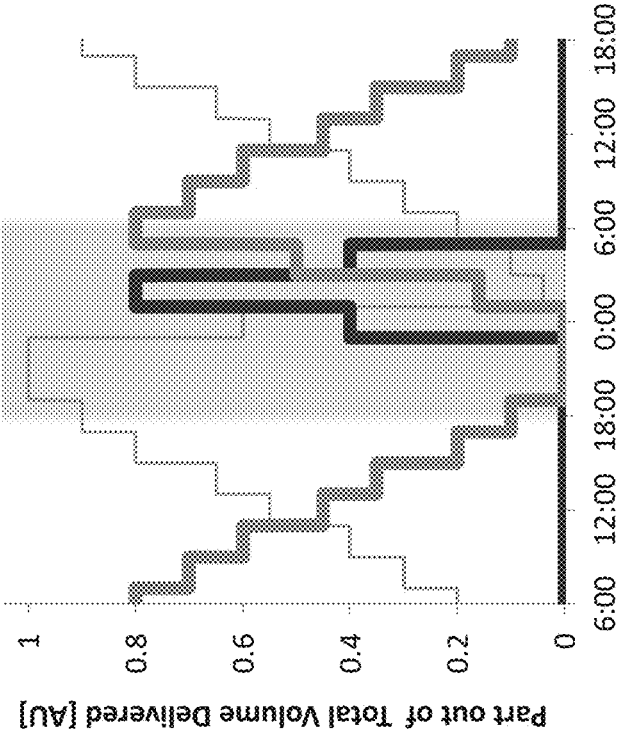

FIGS. 19A-B depict design and implementation of the physiological two-phase hormonal patterns observed in plasma of human patients. FIG. 19A—Computer code design for three oscillating fluids. Time dependent flow rate of the medium with day hormones shown in red. Time dependent flow rate of the medium with night hormones shown in blue. Time dependent flow rate of buffer lacking both hormones shown in green. On each time point the combination of all three flow rates should reach 100% to maintain constant shear forces on the cells. FIG. 19B—Microscopic validation using red fluorescent dye to mark the day hormones, and blue fluorescent dye to mark the night hormones. The results show the present inventor can match both day and night phases with high accuracy.

FIGS. 20A-D depicts real time measurement of glutamate, glutamine, glucose and lactate uptake in 3D organoids composed of endothelial cells and $E6/E7^{LOW}$ Hepatocytes. FIG. 20A schematic cross-section of electrochemical flow sensor. FIG. 20B photograph of Jobst Technologies microsensor. FIG. 20C image of microfluidic set up composed of a microfluidic junction (black) with three inputs connecting into a bioreactor unit (brown-yellow) containing the organoids (not seen). The bioreactor outflow is connected to the Jobst Technologies microsensor which is read by a potentiostat (both blue and white). FIG. 20D Metabolite consumption tracked for 40 hours in the bioreactor unit according to some embodiments of the invention. Organs stabilize their metabolic function within 8 hours of perfusion.

Figure 21:
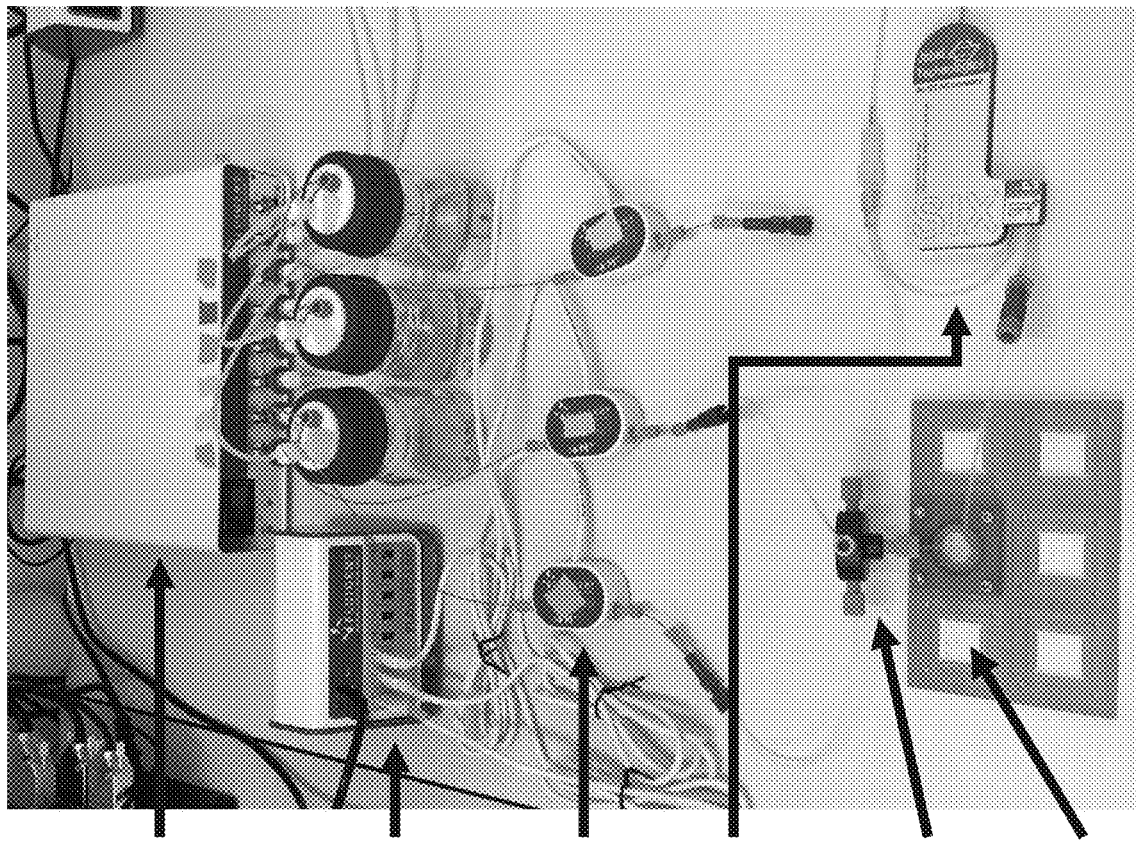

FIG. 21 depicts a display of a microfluidic setup according to some embodiments of the invention used to sustain circadian rhythms in 3D tissues cultured in the microwell bioreactor according to some embodiments of the invention. The setup includes a pressure controller, three culture medium containers and their associated flow meters labeled red, yellow, and green. A microscale 3-inlet mixer connected to the bioreactor, with the outflow connected to electrochemical microsensors.

FIGS. 22A-C—FIG. 22A—Microscopic validation using red fluorescent dye to mark the day hormones, and blue fluorescent dye to mark the night hormones. The results demonstrate that it is possible to match both day and night phases with high accuracy. FIG. 22B—Microscale 3-inlet mixer used to produce the two-phase oscillation. FIG. 22C—A table describing the composition of basal medium (compensation, buffer), with the additives for day medium (red, first stimulus), and the additives for night medium (blue, second stimulus) according to some embodiments of the invention.

FIGS. 23A-H show gene expression levels, as counts, for several circadian and metabolic regulators. The shaded blue bars represent the night phase. Error bars represent the SEM. FIG. 23A shows expression of the following genes: CLOCK, BMAL1, BMAL2, CRY1, CRY2, PER1, PER2, PER3. FIG. 23B shows expression of the following genes: CYP3A4, CYP2C9, CYP2E1; FIG. 23C shows expression of the following genes: CYP2D6, CYP1A2; FIG. 23D shows expression of the following genes: PPARA, PPARD, PPARG, PPARGC1A; FIG. 23E shows expression of the following genes: HSP90AA1, HSPD1 (HSP60); FIG. 23F shows expression of the following genes: P53, INSR, Cyclin E1; FIG. 23G shows expression of the following genes: NCOA1, NCOA2, NCOA3; FIG. 23H shows expression of the following genes: GAPDH, Actin b, UBC, TUBb1, RPL32.

Figure 24:
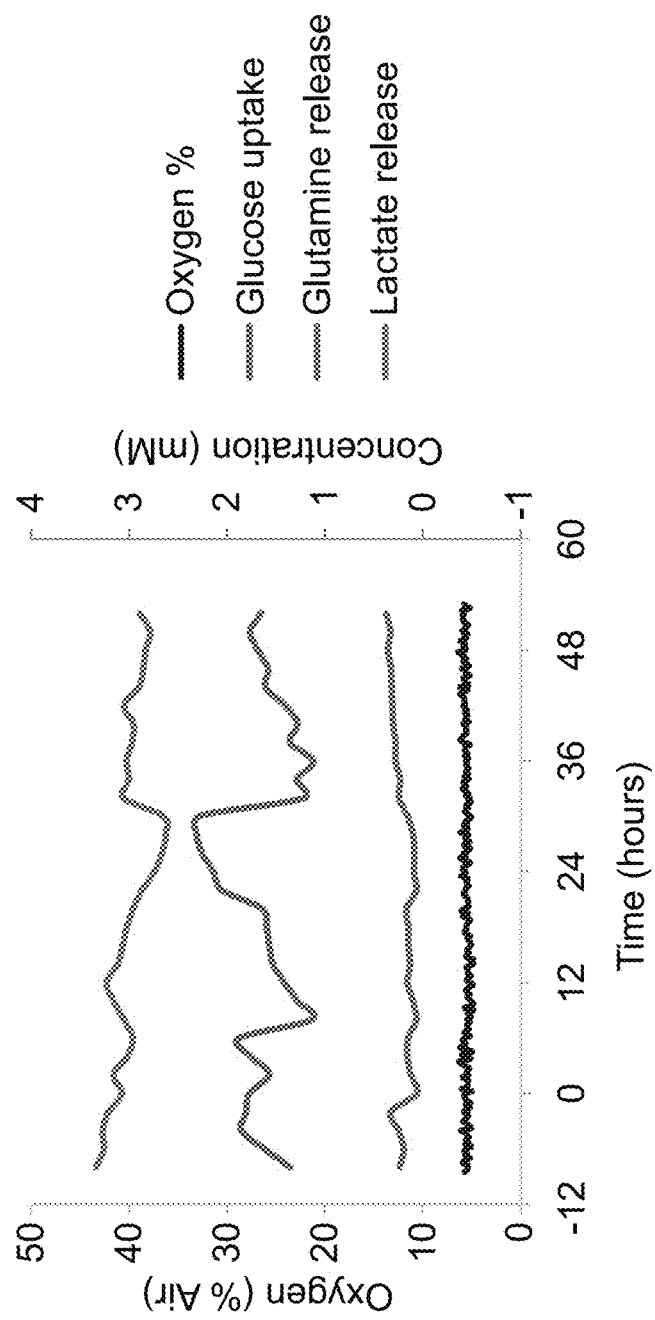

FIG. 24 shows the circadian metabolic rhythms produces by exposing the HepG2/C3A cells to day medium and temperature oscillation.

Figure 25:
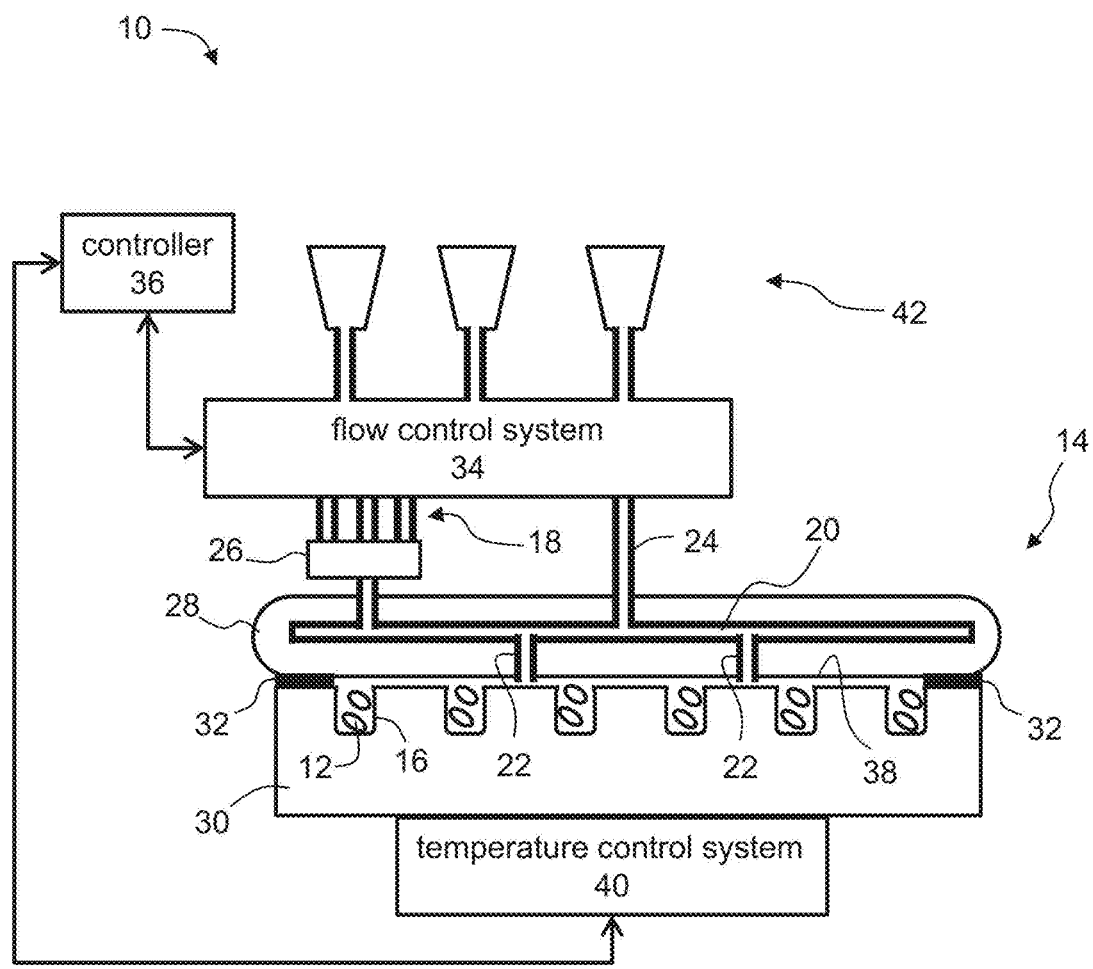

FIG. 25 is a schematic illustration of a system suitable for sustaining a synchronized circadian rhythm in cells of a cell culture, according to some embodiments of the present invention.

DESCRIPTION OF SPECIFIC EMBODIMENTS OF THE INVENTION

The present invention, in some embodiments thereof, relates to an in-vitro method of maintaining a sustainable circadian rhythm in cells of a cell culture and, more particularly, but not exclusively, to a system for inducing and maintaining a sustainable circadian rhythm in cells of a cell culture.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventor has uncovered an in-vitro method and a system for sustaining a synchronized circadian rhythm in cells of a cell culture.

The Examples section which follows shows the system and conditions needed for inducing a sustained circadian rhythm in a cell culture in vitro for at least 2-3 days by subjecting cells to a first stimulus (which is also referred to as a "day" stimulus) and a second stimulus (which is also referred to as a "night" stimulus).

According to an aspect of some embodiments of the invention, there is provided an in-vitro method of sustaining a synchronized circadian rhythm in cells of a cell culture. The method comprising: exposing the cells to a continuous flow of medium and to at least two stimuli provided in an oscillating manner with a periodicity of 24±4 hours, wherein a first stimulus and a second stimulus of said at least two stimuli are distinct, wherein said first stimulus is provided in a first time period and reaches a first peak in a first peak time period, and wherein a second stimulus is provided in a second time period and reaches a second peak in a second peak time period, and wherein an interval between end of time period of said first peak and beginning of said time period of said second peak is at least about 2 hours, thereby sustaining the synchronized circadian rhythm in the cells of the cell culture.

As used herein the phrase "sustaining a synchronized circadian rhythm" refers to maintaining a synchronized circadian rhythm of the cells while being cultured in a cell culture for at least 48 hours.

According to some embodiments of the invention, the synchronized circadian rhythm is sustained for at least 2 days, for at least 3 days, e.g., at least 4 days, at least 5 days, at least 6 days, at least one week, at least two weeks, at least 3 weeks, at least 1 month, at least 2 months and more.

As used herein the phrase "circadian rhythm" refers to a biological process that displays an entrainable rhythm of about 24 hours.

According to some embodiments of the invention, the synchronized circadian rhythm is such that at least 20% of the cells have the same circadian rhythm, e.g., at least 25%, e.g., at least 30%, e.g., at least 35%, e.g., at least 40%, e.g., at least 50%, e.g., at least 60%, at least 65%, at least 70%, at least 75%, at least 80%, at least 85%, at least 90%, at least 95%, at least 99%, or 100% of the cells have the same circadian rhythm.

According to some embodiments of the invention, the synchronized circadian rhythm is such that at least 50% of the cells have the same circadian rhythm.

According to some embodiments of the invention, the cells are characterized by a synchronized metabolic activity within about 1 minute after being exposed to the at least two stimuli, e.g., within about 10 minutes, about 20 minutes, about 30 minutes, about 40 minutes, about 50 minutes, 60 minutes or within about 2 hours after being exposed to the at least two stimuli.

According to some embodiments of the invention, the cells are characterized by a synchronized metabolic activity no later than within 72 hours after being exposed to the at least two stimuli.

According to some embodiments of the invention, the cells are characterized by a synchronized metabolic activity no later than within 72 hours after being exposed to the at least two stimuli, and are maintained in a synchronized metabolic activity for at least 4 days, at least 5 days, at least 6 days, at least one week, at least two weeks, at least 3 weeks, at least 1 month, at least 2 months and more.

As used herein the term "continuous flow" refers to a flow of (e.g., fresh) medium which continues as long as the sustainment of a synchronized circadian rhythm is desired.

It should be noted that the continuous flow of medium can be constant, i.e., having a constant flow rate, or can be a variable flow rate.

According to some embodiments of the invention, the cells are exposed to a constant flow rate.

According to some embodiments of the invention, the continuous flow of medium is provided at a constant rate.

As described, the first stimulus is provided in a first time period and reaches a first peak in a first peak time period, and a second stimulus is provided in a second time period and reaches a second peak in a second peak time period.

As used herein the phrase "stimulus" refers to a generated condition, which is capable of inducing and sustaining a synchronized circadian rhythm in a cell culture.

The generated condition can include one or more agents, at a concentration above a predetermined threshold, and/or a temperature at a level above a predetermined threshold. The agent(s) can include a hormone or an analogue thereof, a gas, or the like.

As used herein the phrase "first time period" refers to a duration of time in which the first stimulus is provided above the predetermined threshold.

Time periods during which the concentration of the agent(s) is below the predetermined threshold is typically not considered part of the time period of the stimulus.

According to some embodiments of the invention, the duration of the first time period is at least about 30 minutes and no more than about 24 hours.

As used herein the phrase "second time period" refers to a duration of time in which the second stimulus is provided above the predetermined threshold.

According to some embodiments of the invention, the duration of said second time period is at least about 10 seconds and no more than about 6 hours.

As used herein the term "peak" refers to a value which is at least 90% of the maximal value of the stimulus within a period of 24±4 hours.

According to some embodiments of the invention, the value of the peak is at least 91%, at least 92%, at least 93%, at least 94%, at least 95%, at least 96%, at least 97%, at least 98%, at least 99%, at least 99.5%, e.g., 100% of the maximal value of the stimulus within a period of 24±4 hours.

Thus, the time period of each peak (first or second peak) can extend from the time point at which the value of the stimulus is equal or higher than 90% of its maximal value until the time point at which the value of the stimulus is less than 90% of its maximal value.

According to some embodiments of the invention, the duration of the time period of the first peak is at least about 1 minute and no more than about 6 hours, e.g., the duration of the time period of the first peak is at least about 2 minutes, 3 minutes, 4 minutes, 5 minutes, 10 minutes, 15 minutes, 20 minutes, 25 minutes, 50 minutes, 60 minutes, 2, hours 3 hours, 4 hours, or 5 hours, and no more than about 6 hours.

According to some embodiments of the invention, the duration of the time period of the second peak is at least about 1 second and no more than about 4 hours, e.g., the duration of the time period of the second peak is at least about 2 seconds, 3 seconds, 4 seconds, 5 seconds, 6 seconds, 7 seconds, 8 seconds, 9 seconds, 10 seconds, 15 seconds, 20 seconds, 25 seconds, 50 seconds, 60 seconds, 2 minutes, 3 minutes, 4 minutes, 5 minutes, 6 minutes, 7 minutes, 8 minutes, 9 minutes, 10 minutes, 15 minutes, 20 minutes, 25 minutes, 50 minutes, 60 minutes, 2 hours, or 3 hours, and no more than about 4 hours.

According to some embodiments of the invention, the interval between end of the time period of the first peak and beginning of the time period of the second peak is no more than about 6 hours.

According to some embodiments of the invention, the interval between end of the time period of the first peak and beginning of the time period of the second peak is at least about 2 hours, e.g., about 2.5 hours, about 3 hours, about 3.5 hours, about 4 hours, about 4.5 hours, about 5 hours.

According to some embodiments of the invention, the second stimulus is absent or present below a predetermined level in the time period of the first peak.

According to some embodiments of the invention, the first stimulus is absent or present below a predetermined level in the time period of the second peak.

According to some embodiments of the invention, the first stimulus is selected from the group consisting of: a first hormone or an analogue thereof, a first temperature, and a first gas.

According to some embodiments of the invention, the first stimulus comprises a first hormone or an analogue thereof.

According to some embodiments of the invention, the first hormone which is used for the first stimulus is selected from the group consisting of: cortisol, testosterone, adiponectin, insulin, thyroxine (T4), and fibroblast growth factor 21 (FGF21).

According to some embodiments of the invention, the analogue of the first hormone is a small molecule.

Methods of identifying such small molecules analogues are known in the art.

According to some embodiments of the invention, the first stimulus comprises at least cortisol or an analogue thereof.

According to some embodiments of the invention, the first stimulus which comprises cortisol or an analogue thereof further comprises at least one hormone or an analogue thereof selected from the group consisting of testosterone, adiponectin, insulin, thyroxine (T4), and fibroblast growth factor 21 (FGF21).

According to some embodiments of the invention, the first stimulus comprises at least insulin or an analogue thereof.

According to some embodiments of the invention, the first stimulus which comprises insulin or an analogue thereof further comprises at least one hormone or an analogue thereof selected from the group consisting of cortisol, testosterone, adiponectin, thyroxine (T4), and fibroblast growth factor 21 (FGF21).

According to some embodiments of the invention, the first stimulus comprises at least cortisol and insulin or analogue(s) thereof.

According to some embodiments of the invention, the first stimulus which comprises cortisol (or an analogue thereof) and insulin (or an analogue thereof) further comprises at least one hormone or an analogue thereof selected from the group consisting of testosterone, adiponectin, thyroxine (T4), and fibroblast growth factor 21 (FGF21).

According to some embodiments of the invention, the first stimulus comprises at least two, at least three, at least four, at least five or all six of the cortisol, testosterone, adiponectin, insulin, thyroxine (T4), and fibroblast growth factor 21 (FGF21) hormones (or analogues thereof).

Cortisol is a steroid hormone, having a CAS Registry Number: 50-23-7. Cortisol is commercially available from various suppliers and manufacturers such as Sigma-Aldrich® (Merck).

According to some embodiments of the invention, the cortisol in the first stimulus is provided at a concentration of at least about 7.5 µg/mL (e.g., 7.5 µg/mL), at least about 8

μg/mL (e.g., 8 μg/mL), at least about 9 μg/mL (e.g., 9 μg/mL), at least about 10 μg/mL (e.g., 10 μg/mL), at least about 11 μg/mL (e.g., 11 μg/mL), at least about 12 μg/mL (e.g., 12 μg/mL), at least about 13 μg/mL (e.g., 13 μg/mL), or at least about 14 μg/mL (e.g., 14 μg/mL).

According to some embodiments of the invention, a cortisol analogue is a Glucocorticoid receptor (GR) agonist.

According to some embodiments of the invention, the cortisol is hydrocortisone or an analogue thereof.

Examples of hydrocortisone analogues include, but are not limited to Chloroprednisone (6α-chloro-17α,21-dihydroxypregna-1,4-diene-3,11,20-trione); Cloprednol (6-chloro-11β,17α,21-trihydroxypregna-1,4,6-triene-3,20-dione); Difluprednate (6α,9α-difluoro-11β,17α,21-trihydroxypregna-1,4-diene-3,20-dione 17α-butyrate 21-acetate); Fludrocortisone (9α-fluoro-11β,17α,21-trihydroxypregn-4-ene-3,20-dione); Fluocinolone (6α,9α-difluoro-11β,16α,17α,21-tetrahydroxypregna-1,4-diene-3,20-dione); Fluperolone (9α-fluoro-11β,17α,21-trihydroxy-21-methylpregna-1,4-diene-3,20-dione); Fluprednisolone (6α-fluoro-11β,17α,21-trihydroxypregna-1,4-diene-3,20-dione); Loteprednol (11β,17α,dihydroxy-21-oxa-21-chloromethylpregna-1,4-diene-3,20-dione); Methylprednisolone (6α-methyl-11β,17α,21-trihydroxypregna-1,4-diene-3,20-dione); Prednicarbate (11β,17α,21-trihydroxypregna-1,4-diene-3,20-dione 17α-ethylcarbonate 21-propionate); Prednisolone (11β,17α,21-trihydroxypregna-1,4-diene-3,20-dione); Prednisone (17α,21-dihydroxypregna-1,4-diene-3,11,20-trione); Tixocortol (11β,17α-dihydroxy-21-sulfanylpregn-4-ene-3,20-dione); and Triamcinolone (9α-fluoro-11β,16α,17α,21-tetrahydroxypregna-1,4-diene-3,20-dione).

Hydrocortisone or analogue thereof can be obtained from various manufacturers and suppliers such as Sigma-Aldrich® (Merck), British Pharmacopoeia, PHARMACY-DIRECT®, and STEMCELL™ TECHNOLOGIES.

According to some embodiments of the invention, the hydrocortisone is provided at a concentration range of about 0.2 μg/mL (e.g., 0.2 μg/mL±10%) to about 15 μg/mL (e.g., 15 μg/mL±10%).

According to some embodiments of the invention, the hydrocortisone in the first stimulus is provided at a concentration range of at least 0.2 μg/mL (microgram per milliliter), at least 0.5 μg/mL, at least 0.7 μg/mL, at least 0.8 μg/mL, at least 0.9 μg/mL, at least 1 μg/mL, at least 2 μg/mL, at least 3 μg/mL, at least 4 μg/mL, at least 5 μg/mL, at least 6 μg/mL, at least 7 μg/mL, at least 7.5 μg/mL, at least 8 μg/mL, at least 9 μg/mL, at least 10 μg/mL, at least 11 μg/mL, at least 12 μg/mL, at least 13 μg/mL, at least 14 μg/mL, e.g., at least about 15 μg/mL and no more than about 500 μg/mL.

According to some embodiments of the invention, the concentration of hydrocortisone does not exceed 500 μg/mL.

According to some embodiments of the invention, the maximal value of the first stimulus comprises hydrocortisone at a concentration of about 7.5 μg/mL.

According to some embodiments of the invention, the cortisol is dexamethasone or analogue thereof.

Examples of dexamethasone analogues include, but are not limited to Alclometasone (7α-chloro-11β,17α,21-trihydroxy-16α-methylpregna-1,4-diene-3,20-dione); Beclometasone (9α-chloro-11β,17α,21-trihydroxy-16β-methylpregna-1,4-diene-3,20-dione); Betamethasone (9α-fluoro-11β,17α,21-trihydroxy-16β-methylpregna-1,4-diene-3,20-dione); Clobetasol (9α-fluoro-11β,17α-dihydroxy-16β-methyl-21-chloropregna-1,4-diene-3,20-dione); Clobetasone (9α-fluoro-16β-methyl-17α-hydroxy-21-chloropregna-1,4-diene-3,11,20-trione); Clocortolone (6α-fluoro-9α-chloro-11β,21-dihydroxy-16α-methylpregna-1,4-diene-3,20-dione); Desoximetasone (9α-fluoro-11β,21-dihydroxy-16α-methylpregna-1,4-diene-3,20-dione); Dexamethasone (9α-fluoro-11β,17α,21-trihydroxy-16α-methylpregna-1,4-diene-3,20-dione); Diflorasone (6α,9α-difluoro-11β,17α,21-trihydroxy-16β-methylpregna-1,4-diene-3,20-dione); Difluocortolone (6α,9α-difluoro-11β,21-dihydroxy-16α-methylpregna-1,4-diene-3,20-dione); Fluclorolone (6α-fluoro-9α,11β-dichloro-16α,17α,21-trihydroxypregna-1,4-dien-3,20-dione); Flumetasone (6α,9α-difluoro-11β,17α,21-trihydroxy-16α-methylpregna-1,4-diene-3,20-dione); Fluocortin (6α-fluoro-11β,21-dihydroxy-16α-methylpregna-1,4-diene-3,20,21-trione); Fluocortolone (6α-fluoro-11β,21-dihydroxy-16α-methylpregna-1,4-diene-3,20-dione); Fluprednidene (9α-fluoro-11β,17α,21-trihydroxy-16-methylenepregna-1,4-diene-3,20-dione); Fluticasone (6α,9α-difluoro-11β,17α-dihydroxy-16α-methyl-21-thia-21-fluoromethylpregna-1,4-dien-3,20-dione); Fluticasone furoate (6α,9α-difluoro-11β,17α-dihydroxy-16α-methyl-21-thia-21-fluoromethylpregna-1,4-dien-3,20-dione 17α-(2-furoate)); Halometasone (2-chloro-6α,9α-difluoro-11β,17α,21-trihydroxy-16α-methylpregna-1,4-diene-3,20-dione); Meprednisone (16β-methyl-17α,21-dihydroxypregna-1,4-diene-3,11,20-trione); Mometasone (9α,21-dichloro-11β,17α-dihydroxy-16α-methylpregna-1,4-diene-3,20-dione); Mometasone furoate (9α,21-dichloro-11β,17α-dihydroxy-16α-methylpregna-1,4-diene-3,20-dione 17α-(2-furoate)); Paramethasone (6α-fluoro-11β,17α,21-trihydroxy-16α-methylpregna-1,4-diene-3,20-dione); Prednylidene (11β,17α,21-trihydroxy-16-methylenepregna-1,4-diene-3,20-dione); Rimexolone (11β-hydroxy-16α,17α,21-trimethylpregna-1,4-dien-3,20-dione) and Ulobetasol (halobetasol) (6α,9α-difluoro-11β,17α-dihydroxy-16β-methyl-21-chloropregna-1,4-diene-3,20-dione).

According to some embodiments of the invention, the small molecule which is an analogue of cortisol is dexamethasone.

According to some embodiments of the invention, the dexamethasone is provided at a concentration of about 0.01 μM (e.g., 0.01 μM±10%) to about 200 μM (e.g., 200 μM±10%).

According to some embodiments of the invention, the dexamethasone in the medium of the first stimulus is provided at a concentration range of at least 0.01 μM, at least 0.02 μM, at least 0.03 μM, at least 0.04 μM, at least 0.05 μM, at least 0.1 μM, at least 0.2 μM, at least 0.3 μM, at least 0.4 μM, at least 0.5 μM, at least 0.6 μM, at least 0.7 μM, at least 0.8 μM, at least 0.9 μM, at least 0.1 μM, at least 0.2 μM, at least 0.5 μM, at least 1 μM, at least 5 μM, at least 10 μM, at least 20 μM, at least 30 μM, at least 40 μM, at least 50 μM, at least 60 μM, at least 70 μM, at least 80 μM, at least 90 μM, at least 100 μM (e.g., about 100 μM), at least 110 μM, at least 120 μM, at least 130 μM, at least 140 μM, at least 150 μM, at least 160 μM, at least 170 μM, at least 180 μM, at least 190 μM, e.g., at least about 200 μM and no more than about 500 μM.

According to some embodiments of the invention, the concentration of dexamethasone does not exceed 500 μM.

According to some embodiments of the invention, the maximal value of the first stimulus comprises dexamethasone at a concentration of about 100 μM.

Testosterone (CAS Registry Number: 58-22-0; chemical formula C19H28O2) is the primary male sex hormone and an anabolic steroid. Testosterone is commercially available from various suppliers and manufacturers such as Sigma-Aldrich® (Merck).

According to some embodiments of the invention, a testosterone analogue is an Androgen receptor (AR) agonist.

According to some embodiments of the invention, the testosterone analogue is Dihydrotestosterone (DHT), androstenedione, androstenediol, dehydroepiandrosterone, methyltestosterone, metandienone, nandrolone, trenbolone, oxandrolone, and/or stanozolol.

According to some embodiments of the invention, the small molecule which is an analogue of testosterone is dihydrotestosterone (DHT).

According to some embodiments of the invention, the concentration of the testosterone (a steroid hormone) in the medium of the first stimulus is at least 4 pM (picomolar), e.g., at least about 40 pM, e.g., at least about 100 pM, e.g., at least about 200 pM, e.g., at least about 500 pM, e.g., at least about 1000 pM, e.g., at least about 2 nM (nanomolar), e.g., at least about 3 nM, e.g., at least about 4 nM, e.g., at least about 5 nM, e.g., at least about 6 nM, e.g., at least about 7 nM, e.g., at least about 8 nM, e.g., at least about 9 nM, e.g., at least about 10 nM (e.g., 10 nM), e.g., at least about 20 nM, e.g., at least about 30 nM, e.g., at least about 40 nM, e.g., at least about 50 nM, e.g., at least about 60 nM, e.g., at least about 70 nM, e.g., at least about 80 nM, e.g., at least about 90 nM, e.g., at least about 100 nM (e.g., 100 nM), e.g., at least about 110 nM, e.g., at least about 120 nM, e.g., at least about 130 nM, e.g., at least about 140 nM, e.g., at least about 150 nM, e.g., at least about 160 nM, e.g., at least about 170 nM, e.g., at least about 180 nM, e.g., at least about 190 nM, e.g., at least about 200 nM (e.g., 200 nM) and no more than about 500 nM.

According to some embodiments of the invention, the concentration of testosterone does not exceed 500 nM.

According to some embodiments of the invention, the maximal value of the first stimulus comprises testosterone at a concentration of about 10 nM.

According to some embodiments of the invention, the maximal value of the first stimulus comprises testosterone at a concentration of about 100 nM.

According to some embodiments of the invention, the testosterone analogue is Dihydrotestosterone (DHT, 5α-androstan-17β-ol-3-one).

According to some embodiments of the invention, when Dihydrotestosterone (DHT, 5α-androstan-17β-ol-3-one) is used instead of testosterone, the maximal level of DHT in the first stimulus is at least about 200 pM.

As used herein the term "adiponectin" refers to a protein hormone involved in regulating glucose levels as well as fatty acid breakdown. The adiponectin precursor (GenBank Accession No. NP_001171271.1; SEQ ID NO: 1) is encoded by either mRNA variant 1 (GenBank Accession No. NM_001177800.1; SEQ ID NO: 11) or variant 2 (GenBank Accession No. NM_004797.4; SEQ ID NO: 12).

According to some embodiments of the invention, an adiponectin analogue is an AdipoR1 (Adiponectin Receptor 1) and/or AdipoR2 (Adiponectin receptor 2) agonist.

Example of adiponectin analogues, include, but are not limited to Tiliroside, ADP355, and AdipoRon.

According to some embodiments of the invention, the small molecule which is an analogue of adiponectin is Tiliroside or AdipoRon (an adiponectin receptor agonist) like molecule.

Adiponectin or an analogue thereof is commercially available from various suppliers and manufacturers such as Sigma-Aldrich® (e.g., catalogue number SRP4901).

According to some embodiments of the invention, the concentration of the adiponectin (a protein hormone) in the medium in the first stimulus is at least 100 ng/mL, e.g., at least 200 ng/mL, e.g., at least 300 ng/mL, e.g., at least 400 ng/mL, e.g., at least 500 ng/mL, e.g., at least 600 ng/mL, e.g., at least 700 ng/mL, e.g., at least 800 ng/mL, e.g., at least 800 ng/mL, e.g., at least 1000 ng/mL, e.g., at least 2 µg/mL, e.g., at least 3 µg/mL, e.g., at least 4 µg/mL, e.g., at least 5 µg/mL, e.g., at least 6 µg/mL, e.g., at least 7 µg/mL, e.g., at least 8 µg/mL, e.g., at least 9 µg/mL, e.g., at least 10 µg/mL (e.g., about 10 µg/mL) and no more than about 100 µg/mL.

According to some embodiments of the invention, the concentration of adiponectin does not exceed 100 µg/ml.

According to some embodiments of the invention, the maximal value of the first stimulus comprises adiponectin at a concentration of about 10 µg/mL.

Insulin is a peptide hormone which regulates the metabolism of carbohydrates, fats and protein by promoting the absorption of carbohydrates, especially glucose from the blood into liver, fat and skeletal muscle cells. The insulin precursor (GenBank Accession NO. NP_000198.1; SEQ ID NO: 2) can be encoded by 4 mRNA variants: Variant 1 (GenBank Accession No. NM_000207.2; SEQ ID NO: 13), Variant 2 (GenBank Accession No. NM_001185097.1; SEQ ID NO: 14), Variant 3 (GenBank Accession No. NM_001185098.1; SEQ ID NO: 15) and/or Variant 4 (GenBank Accession No. NM_001291897.1; SEQ ID NO: 16). After removal of the precursor signal peptide, proinsulin is post-translationally cleaved into three peptides: the B chain and A chain peptides, which are covalently linked via two disulfide bonds to form insulin, and C-peptide.

According to some embodiments of the invention, an insulin analogue is an insulin receptor agonist.

Examples of insulin analogues include, but are not limited to 4548-G05, DMAQ-B1, TLK19780, and peptides such as lispro, aspart, glulisine, detemir, degludec, and glargine.

According to some embodiments of the invention, the small molecule which is an analogue of insulin is chaetochromin derivative (4548-G05). Insulin or analogues thereof are commercially available from various suppliers and manufacturers such as Sigma-Aldrich® (Merck), ThermoFisher SCIENTIFIC and PEPROTECH®.

According to some embodiments of the invention, the concentration of the insulin in the medium which is comprised in the first stimulus is at least 10 pmol/L (picomole per liter, picomolar) and does not exceed 1 mg/mL (milligram per milliliter). According to some embodiments of the invention, the concentration of the insulin in the medium in the first stimulus is at least 10 pmol/L, e.g., at least 100 pmol/L, e.g., at least 200 pmol/L, e.g., at least 500 pmol/L, e.g., at least 800 pmol/L, e.g., at least 1000 pmol/L, e.g., at least 2 nM (nanomolar), e.g., at least 10 nM (nanomolar), e.g., at least 20 nM (nanomolar), e.g., at least 40 nM (nanomolar), e.g., at least 50 nM (nanomolar), e.g., at least 60 nM (nanomolar), e.g., at least 70 nM (nanomolar), e.g., at least 80 nM (nanomolar), e.g., at least 90 nM (nanomolar), e.g., at least 100 nM (nanomolar), e.g., at least 120 nM (nanomolar), e.g., at least 140 nM (nanomolar), e.g., at least 150 nM (nanomolar), e.g., at least 160 nM (nanomolar), e.g., at least 170 nM (nanomolar), e.g., about 174 nM (about 1 µg/ml), e.g., at least 200 nM, e.g., at least 300 nM, e.g., at least 400 nM, e.g., at least 500 nM, e.g., at least 700 nM, e.g., at least 900 nM, e.g., at least 1000 nM, e.g., at least 1200 nM, e.g., at least 1500 nM, e.g., at least 1700 nM, e.g., about 1740 nM (about 10 µg/ml) and no more than 1 mg/mL.

According to some embodiments of the invention, the concentration of insulin does not exceed 1 mg/mL (about 174 µM).

According to some embodiments of the invention, the maximal value of the first stimulus comprises insulin at a concentration of about 1 to 10 µg/mL.

According to some embodiments of the invention, the maximal value of the first stimulus comprises insulin at a concentration of about 1 µg/mL.

According to some embodiments of the invention, the maximal value of the first stimulus comprises insulin at a concentration of about 10 µg/mL. Thyroxine (T4) (CAS Number: 51-48-9. Molecular Formula: C15H11I4NO4) is non-protein hormone produced and released by the thyroid gland. Thyroxine (T4) is commercially available from various suppliers and manufacturers such as Sigma-Aldrich® (Merck).

According to some embodiments of the invention, a T4 analogue is a thyroid hormone receptor agonist.

Non-limiting examples of T4 analogues include Eprotirome, Triac, DITPA, KB141, Sobetriome, MB07344, and GC-24.

According to some embodiments of the invention, the small molecule which is an analogue of thyroxine (T4) is Eprotirome.

According to some embodiments of the invention, the concentration of the thyroxine (T4) in the medium which is comprised in the first stimulus is at least 0.01 nM, e.g., at least 0.05 nM, e.g., at least 0.08 nM, e.g., at least 0.1 nM, e.g., at least 0.15 nM, e.g., at least 0.2 nM, e.g., at least 0.4 nM, e.g., at least 0.5 nM, e.g., at least 0.8 nM, e.g., at least 1 nM, e.g., at least 2 nM, e.g., at least 3 nM, e.g., at least 4 nM, e.g., at least 5 nM, e.g., at least 6 nM, e.g., at least 7 nM, e.g., at least 8 nM, e.g., at least 9 nM, e.g., at least 10 nM (e.g., 10 nM), e.g., at least 20 nM, e.g., at least 30 nM, e.g., at least 50 nM, e.g., at least 100 nM and no more than about 50 µM.

According to some embodiments of the invention, the concentration of thyroxine does not exceed 50 µM.

According to some embodiments of the invention, the maximal value of the first stimulus comprises thyroxine at a concentration of about 10 nM.

Fibroblast growth factor 21 (FGF21) is a member of the fibroblast growth factor (FGF) family. FGF family members possess broad mitogenic and cell survival activities and are involved in a variety of biological processes. Fibroblast growth factor 21 is a secreted endocrine factor that functions as a major metabolic regulator. Fibroblast growth factor 21 stimulates the uptake of glucose in adipose tissue.

Fibroblast growth factor 21 protein (GenBank Accession No. NP_061986.1; SEQ ID NO: 3) is encoded by mRNA as set forth in GenBank Accession No. NM_019113.3 (SEQ ID NO: 17).

According to some embodiments of the invention, an FGF21 analogue is an FGF21 receptor agonist.

According to some embodiments of the invention, the small molecule which is an analogue of fibroblast growth factor 21 (FGF21) is LY2405319.

Fibroblast growth factor 21 or analogues thereof are commercially available from various suppliers and manufacturers such as PEPROTECH®, and Sigma-Aldrich® (Merck).

According to some embodiments of the invention, the concentration of the fibroblast growth factor 21 (FGF21) in the medium in the first stimulus is at least 1 pM (picomolar), e.g., at least 10 pM, e.g., at least 50 pM, e.g., at least 100 pM, e.g., at least 500 pM, e.g., at least 1000 pM, e.g., at least 2 nM (nanomolar), e.g., at least 5 nM, e.g., at least 10 nM, e.g., at least 15 nM, e.g., at least 20 nM, e.g., at least 25 nM, e.g., at least 30 nM, e.g., at least 35 nM, e.g., at least 40 nM, e.g., at least 45 nM, e.g., at least 50 nM, e.g., at least 60 nM, e.g., at least 70 nM, e.g., at least 100 nM and no more than 1000 nM.

According to some embodiments of the invention, the concentration of FGF21 does not exceed 1000 nM.

According to some embodiments of the invention, the maximal value of the first stimulus comprises FGF21 at a concentration of about 50 nM.

As described, the stimulus can be a specific temperature to which the cells are exposed. It should be noted that the first stimulus can be the temperature alone or a combined stimulus of a specific temperature and hormone, a specific temperature and a specific gas and/or a specific temperature, a specific hormone (or a combination or hormones from the list of "first hormone" or analogue thereof) and/or a specific gas.

According to some embodiments of the invention, the first stimulus comprises a first temperature.

According to some embodiments of the invention, the first stimulus comprises a first hormone (or an analogue thereof) and a first temperature.

According to some embodiments of the invention the first temperature of the first stimulus is between about 35.5° C. to about 36.7° C.

According to some embodiments of the invention, the first temperature of the first stimulus is between about 35.7 and about 36.3° C., e.g., between 35.8-36.2° C., e.g., about 35.9° C., about 36.0° C., about 36.1° C., e.g., 36° C.

According to some embodiments of the invention, the first temperature and/or the second temperature does not exceed above 40° C.

According to some embodiments of the invention, the first temperature and/or the second temperature does not decrease below 30° C.

According to an embodiment of the invention, the temperature of the second stimulus is a baseline temperature of about 36.7° C., or higher, e.g., 37° C.

According to some embodiments of the invention the first temperature of the first stimulus is lower in about 1 Celsius degree as compared to the second temperature of the second stimulus.

According to some embodiments of the invention, the second temperature in the second stimulus is between about 36.3° C. to about 38.0° C., 36.5° C. to about 37.9° C., e.g., between 36.7-37.7° C., e.g., between 36.9-37.6° C., e.g., 37.2° C., e.g., 37.3° C., e.g., 37.4° C. e.g., 37.5° C.

According to some embodiments of the invention the first or second gas is oxygen.

According to some embodiments of the invention the oxygen is provided at a concentration between 0-100%, e.g., 1-100%.

According to some embodiments of the invention the first gas of the first stimulus is oxygen provided at a concentration of about 21-24%.

According to some embodiments of the invention the first gas of the first stimulus is oxygen provided at a concentration of about 21%.

According to some embodiments of the invention the first gas of the first stimulus is provided at a higher concentration of at least about 3% of oxygen as compared to the second gas in the second stimulus.

It should be noted that the oxygen can be carried on a carrier present in the medium.

According to some embodiments of the invention the culture medium comprises an oxygen carrier.

Hemoglobin(s) or perfluorocarbon based oxygen carrier(s) can increase the oxygen carrying capacity of the medium, requiring less partial pressure of oxygen to solubilize similar concentrations of the gas.

Hemoglobin can be a recombinant human hemoglobin, a cross linked hemoglobin, or an animal derived hemoglobin.

Hemoglobin can be obtained from various manufacturers such as from Biopure corporation, e.g., HEMOCURE.

According to some embodiments of the invention the hemoglobin is HBOC-201, bovine purified hemoglobin crosslinked and polymerized with glutaraldehyde.

Typical concentrations of hemoglobin in the culture medium are about 6 to 17.5 g/dL (Gram/deciliter).

Perfluorocarbon-based oxygen carriers (PFCOCs) are chemically inert synthetic molecules that consist primarily of carbon and fluorine atoms, and they are capable of physically dissolving significant quantities of many gases including oxygen and carbon dioxide. Perfluorochemicals are hydrophobic, and are therefore not miscible with water. Typically perfluorochemicals are emulsified prior to use in a liquid medium.

Perfluorocarbon (also known as "Perflubron") can be obtained from various manufacturers and suppliers such as Sigma-Aldrich (MERCK), e.g., catalogue number 343862.

Typically the perfluorocarbon-based oxygen carriers are used in emulsions of about 60% wt/wt (weight per weight), and the concentrations of such Perfluorocarbon-based oxygen carriers emulsions in the culture medium are about 10% to about 25%.

According to some embodiments of the invention, the second stimulus is selected from the group consisting of: a second hormone or an analogue thereof, a second temperature and a second gas.

According to some embodiments of the invention, the analogue of the second hormone is a small molecule.

According to some embodiments of the invention, the second hormone is selected from the group consisting of: melatonin, growth hormone, Triiodothyronine (T3), ghrelin, prolactin, TSH, vasopressin, and leptin.

According to some embodiments of the invention, the second stimulus comprises at least melatonin or an analogue thereof.

According to some embodiments of the invention, the second stimulus which comprises melatonin or an analogue thereof further comprises at least one hormone or an analogue thereof selected from the group consisting of growth hormone, Triiodothyronine (T3), ghrelin, prolactin, TSH, vasopressin, and leptin.

According to some embodiments of the invention, the second stimulus comprises at least growth hormone or an analogue thereof.

According to some embodiments of the invention, the second stimulus which comprises growth hormone or an analogue thereof further comprises at least one hormone or an analogue thereof selected from the group consisting of melatonin, Triiodothyronine (T3), ghrelin, prolactin, TSH, vasopressin, and leptin.

According to some embodiments of the invention, the second stimulus comprises at least melatonin (or an analogue thereof) and growth hormone (or an analogue thereof).

According to some embodiments of the invention, the second stimulus which comprises melatonin (or an analogue thereof) and growth hormone (or an analogue thereof) further comprises at least one hormone or an analogue thereof selected from the group consisting of Triiodothyronine (T3), ghrelin, prolactin, TSH, vasopressin, and leptin.

According to some embodiments of the invention, the second stimulus comprises at least two, at least three, at least four, at least five, at least six, at least seven or all eight hormones (or analogues thereof) of the following hormones: melatonin, growth hormone, Triiodothyronine (T3), ghrelin, prolactin, TSH, vasopressin, and leptin.

Melatonin (CAS Registry Number: 73-31-4; Chemical Formula C13H16N2O2) is a non-protein hormone produced by the pineal gland among other locations, and regulates wakefulness.

According to some embodiments of the invention, the melatonin analogue is melatonin receptor ($MT_1$, $MT_2$) agonist.

According to some embodiments of the invention, the small molecule which is an analogue of melatonin is UCM 1037, 6-Hydroxymelatonin, Agomelatine, GR-196429, N-Acetylserotonin, Piromelatine, Ramelteon, Tasimelteon, TIK-301 (LY-156735).

Melatonin or an analogue thereof is commercially available from various suppliers and manufacturers such as Sigma-Aldrich® (Merck), Calbiochem, R&D Systems, and British Pharmacopoeia.

According to some embodiments of the invention, the melatonin is provided at a concentration range of at least about 0.001 mM (±10%) and to about 5 mM (±10%).

According to some embodiments of the invention, the melatonin is provided at a concentration range of at least about 0.001 mM (±10%) and to about 200 μM (±10%).

According to some embodiments of the invention, the melatonin is provided in the second stimulus at a concentration range of at least 0.001 mM, at least 0.002 mM, e.g., at least 0.005 mM, e.g., at least 0.01 mM, e.g., at least 0.012 mM, e.g., at least 0.015 mM, e.g., at least 0.018 mM, e.g., at least 0.02 mM, e.g., at least 0.03 mM, e.g., at least 0.04 mM, e.g., at least 0.05 mM, e.g., at least 0.06 mM, e.g., at least 0.08 mM, e.g., at least 0.1 mM, e.g., at least 0.11 mM, e.g., at least 0.15 mM, e.g., at least about 0.2 mM (±10%), e.g., at least 0.3 mM, e.g., at least 0.4 mM, e.g., at least 0.5 mM, e.g., at least 0.6 mM and no more than about 5 mM.

According to some embodiments of the invention, the maximal value of the second stimulus comprises melatonin at a concentration of about 200 μM.

According to some embodiments of the invention, the concentration of melatonin in the second stimulus does not exceed 5 mM.

Growth hormone (GH) is a protein hormone, also known as somatotropin, that stimulates growth, cell reproduction, and cell regeneration in humans and other animals. Growth hormone is encoded by a gene having the GH1 symbol, and has several isoforms, encoded by three variants, as follows: somatotropin isoform 1 precursor (Variant 1) set forth by GenBank Accession No. NP_000506.2 (protein; SEQ ID NO: 4) encoded by NM_000515.5 (mRNA; SEQ ID NO:18); somatotropin isoform 2 precursor (Variant 2) set forth by GenBank Accession NO. NP_072053.1 (SEQ ID NO: 5), encoded by NM_022559.3 (SEQ ID NO: 19); and somatotropin isoform 3 precursor (Variant 3) set forth by GenBank Accession No. NP_072054.1 (SEQ ID NO:6), encoded by NM_022560.3 (SEQ ID NO: 20).

According to some embodiments of the invention, an analogue of growth hormone is a growth hormone receptor (GHR) agonist.

According to some embodiments of the invention, the small molecule which is an analogue of growth hormone is Pegvisomant or helix-enhanced [Ala15]GRH-(1-29)NH2.

Growth hormone or an analogue thereof can be provided from several manufacturers and suppliers such as Scien- Cell™ (Research Laboratories), Lee Biosolutions, Inc., ProSpec-Tany TechnoGene Ltd., R&D SYSTEMS®, and SignalChem.

According to some embodiments of the invention, the growth hormone in the second stimulus is provided at a concentration range of at least about 0.001 ng/ml to about 200 ng/ml.

According to some embodiments of the invention, the growth hormone is provided at a concentration range of 0-100 ng/ml.

According to some embodiments of the invention, the growth hormone in the second stimulus is provided at a concentration range of at least 0.001 ng/ml, at least 0.002 ng/ml, at least 0.005 ng/ml, at least 0.01 ng/ml, at least 0.02 ng/ml, at least 0.05 ng/ml, at least 0.1 ng/ml, at least 0.12 ng/ml, at least 0.15 ng/ml, at least 0.2 ng/ml, at least 0.3 ng/ml, at least 0.5 ng/ml, at least 0.6 ng/ml, at least 0.7 ng/ml, at least 0.8 ng/ml, at least 0.9 ng/ml, at least 1 ng/ml, at least 2 ng/ml, at least 3 ng/ml, at least 5 ng/ml, at least 10 ng/ml, at least 15 ng/ml, at least 20 ng/ml, at least 25 ng/ml, at least 30 ng/ml (e.g., about 30 ng/ml, e.g., 30 ng/ml), at least 35 ng/ml, at least 40 ng/ml, at least 45 ng/ml, at least 50 ng/ml, at least 55 ng/ml, at least 60 ng/ml, at least 65 ng/ml, at least 70 ng/ml, at least 75 ng/ml, at least 80 ng/ml, at least 85 ng/ml, at least 90 ng/ml, at least 95 ng/ml, at least 99 ng/ml, e.g., 100 ng/ml and no more than about 200 ng/ml.

According to some embodiments of the invention, the maximal value of the second stimulus comprises growth hormone at a concentration of about 30 ng/ml.

According to some embodiments of the invention, the concentration of growth hormone in the second stimulus does not exceed 200 ng/ml.

Triiodothyronine (T3) is a thyroid hormone having a CAS number 6893-02-3, which is mainly formed by the peripheral enzymatic monodeiodination of T4 at the 5 position of the inner ring of the iodothyronine nucleus.

According to some embodiments of the invention, an analogue of T3 is a weak thyroid hormone receptor agonist.

Known analogues of Triiodothyronine (T3) include, but are not limited to 3,3',5'-Triiodo-L-thyronine.

Triiodothyronine (T3) or analogue(s) thereof can be obtained from several manufacturers and suppliers such as SIGMA-ALDRICH® (MERCK).

According to some embodiments of the invention, the Triiodothyronine (T3) in the second stimulus is provided at a concentration range of at least 0.01 nM, e.g., at least 0.05 nM, e.g., at least 0.1 nM, e.g., at least 0.2 nM, e.g., at least 0.5 nM, e.g., at least 1 nM, e.g., at least 2 nM, e.g., at least 3 nM, e.g., at least 4 nM, e.g., at least 5 nM, e.g., at least 6 nM, e.g., at least 7 nM, e.g., at least 8 nM, e.g., at least 9 nM, e.g., at least 10 nM (e.g., about 10 nM, e.g., 10 nM), e.g., at least 20 nM, e.g., at least 30 nM, e.g., at least 40 nM, e.g., at least 50 nM, e.g., at least 100 nM and no more than about 50 µM.

According to some embodiments of the invention, the maximal value of the second stimulus comprises T3 at a concentration of about 10 nM.

According to some embodiments of the invention, the concentration of Triiodothyronine (T3) in the second stimulus does not exceed 50 µM.

Ghrelin is a peptide hormone, encoded by the GHRL gene (ghrelin and obestatin prepropeptide). The ghrelin-obestatin preproprotein [e.g., as depicted by GenBank Accession No. NP_057446.1 (SEQ ID NO:26), encoded by mRNA GenBank Accession No. NM_016362.4 (SEQ ID NO: 27)] is cleaved to yield two peptides, ghrelin and obestatin. Ghrelin is a powerful appetite stimulant and plays an important role in energy homeostasis. Its secretion is initiated when the stomach is empty, whereupon it binds to the growth hormone secretagogue receptor in the hypothalamus which results in the secretion of growth hormone (somatotropin). The mature Ghrelin polypeptide is depicted by SEQ ID NO: 28 (GSSFLSP EHQRVQQRKESKKPPAKLQPR).

According to some embodiments of the invention the Ghrelin polypeptide comprises an in n-octanoylated serine on the third amino acid residue, which is necessary for biological activity.

According to some embodiments of the invention a ghrelin analogue is an agent having an anti-cachexia activity. For example, upon subcutaneous administration, a ghrelin peptide analogue binds to and stimulates the G protein-coupled growth hormone secretagogue receptor (GHSR) in the central nervous system (CNS), thereby mimicking the appetite-stimulating and growth hormone-releasing effects of endogenous ghrelin.

According to some embodiments of the invention a ghrelin analogue is a ghrelin/growth hormone secretagogue receptor (GHS-R) agonist.

Known analogues of Ghrelin include, but are not limited to Dpr3(octanoyl), Lys19(68Ga-DOTA)]ghrelin(1-19); AZP-531 (an unacylated ghrelin analog); BIM-28131; BIM-28125; BIM-28163; and the like.

Ghrelin or analogue(s) thereof can be obtained from several manufacturers and suppliers such as Sigma-Aldrich® (Merck), Cayman CHEMICAL, MCE® MedChemExpress, and MedKoo Biosciences, Inc.

According to some embodiments of the invention, the Ghrelin in the second stimulus is provided at a concentration range of at least 0.01 nM, e.g., at least 0.05 nM, e.g., at least 0.1 nM, e.g., at least 0.5 nM, e.g., at least 1 nM, e.g., at least 5 nM, e.g., at least 10 nM, e.g., at least 20 nM, e.g., at least 30 nM, e.g., at least 40 nM, e.g., at least 50 nM, e.g., at least 60 nM, e.g., at least 70 nM, e.g., at least 80 nM, e.g., at least 90 nM, e.g., at least 100 nM, e.g., about 100 nM (e.g., 100 nM), e.g., at least 120 nM, e.g., at least 150 nM, e.g., at least 200 nM, e.g., at least 300 nM, e.g., at least 400 nM and no more than about 50 µM.

According to some embodiments of the invention, the maximal value of the second stimulus comprises Ghrelin at a concentration of about 100 nM.

According to some embodiments of the invention, the concentration of Ghrelin in the second stimulus does not exceed 50 µM.

Prolactin, also known as luteotropic hormone or luteotropin, is the anterior pituitary hormone which functions as a growth regulator for many tissues, including cells of the immune system. It may also play a role in cell survival by suppressing apoptosis, and it is essential for lactation. Prolactin having the amino acid sequence set forth by GenBank Accession No. NP_000939.1 (SEQ ID NO: 7), encoded by either one of the two variant mRNA sequences having GenBank Accession Nos. NM_000948.6 (SEQ ID NO: 21) and NM_001163558.2 (SEQ ID NO: 22).

According to some embodiments of the invention, a prolactin analogue is a Prolactin receptor (PRLR) agonist.

A known analogue of prolactin include, but is not limited to Terlipressin.

Prolactin and analogues thereof can be obtained from various manufacturers and suppliers such as SIGMA-ALDRICH® (MERCK), and PeproTech.

According to some embodiments of the invention, the Prolactin in the second stimulus is provided at a concentration range of at least 0.01 µg/L (micrograms per liter), e.g., at least 0.05 µg/L, e.g., at least 0.1 µg/L, e.g., at least 0.2

μg/L, e.g., at least 0.5 μg/L, e.g., at least 1 μg/L, e.g., at least 2 μg/L, e.g., at least 3 μg/L, e.g., at least 4 μg/L, e.g., at least 5 μg/L, e.g., at least 6 μg/L, e.g., at least 7 μg/L, e.g., at least 8 μg/L, e.g., at least 9 μg/L, e.g., at least 10 μg/L (e.g., about 10 μg/L), e.g., at least 20 μg/L, e.g., at least 100 μg/L, and no more than about 500 μg/L.

According to some embodiments of the invention, the maximal value of the second stimulus comprises prolactin at a concentration of about 10 μg/L (e.g., 10 μg/L).

According to some embodiments of the invention, the concentration of Prolactin in the second stimulus does not exceed 500 μg/L.

Thyroid Stimulating Hormone (TSH) functions in the control of thyroid structure and metabolism. TSH consists of a dimer composed of two subunits, alpha and beta, which are non-covalently associated. The alpha subunit of TSH is identical to the alpha subunit of the four human glycoprotein hormones: chorionic gonadotropin (CG), luteinizing hormone (LH), follicle stimulating hormone (FSH), and thyroid stimulating hormone (TSH), however, their beta chains are unique and confer biological specificity. The beta chain of TSH is encoded by the TSHB gene. There are two protein variants of TSH-beta, isoform 1 having GenBank Accession NO. NP_000540.2 (SEQ ID NO:8), encoded by NM_000549.4 (SEQ ID NO: 23) and isoform 2 having GenBank Accession No. NP_001264920.1 (SEQ ID NO:9), encoded by NM_001277991.1 (SEQ ID NO: 24).

According to some embodiment of the invention a TSH analogue is a Thyrotropin receptor agonist.

A non-limiting example of a TSH analogue is TR1401.

TSH or an analogue thereof can be obtained from various manufacturers or suppliers such as MyBioSource, LifeSpan BioSciences Inc. and Trophogen, Inc.

According to some embodiments of the invention, the TSH in the second stimulus is provided at a concentration range of at least 0.1 ng/ml (nanograms per milliliter), e.g., at least 0.5 ng/ml, e.g., at least 1 ng/ml, e.g., at least 5 ng/ml, e.g., at least 10 ng/ml, e.g., at least 20 ng/ml, e.g., at least 50 ng/ml, e.g., at least 60 ng/ml, e.g., at least 70 ng/ml, e.g., at least 80 ng/ml, e.g., at least 90 ng/ml, e.g., at least 100 ng/ml, e.g., at least 110 ng/ml, e.g., at least 120 ng/ml, e.g., at least 125 ng/ml (e.g., about 125 ng/ml), e.g., at least 130 ng/ml, e.g., at least 150 ng/ml, e.g., at least 200 ng/ml and no more than about 750 ng/ml.

According to some embodiments of the invention, the maximal value of the second stimulus comprises TSH at a concentration of about 125 ng/ml (e.g., 125 ng/ml).

According to some embodiments of the invention, the concentration of TSH in the second stimulus does not exceed 750 ng/ml.

Vasopressin, also called antidiuretic hormone (ADH), arginine vasopressin (AVP) or argipressin, is a hormone synthesized as a peptide prohormone in neurons in the hypothalamus, and is converted to AVP. Arginine vasopressin is a posterior pituitary hormone that is synthesized in the supraoptic nucleus and paraventricular nucleus of the hypothalamus. Along with its carrier protein, neurophysin 2, it is packaged into neurosecretory vesicles and transported axonally to the nerve endings in the neurohypophysis where it is either stored or secreted into the bloodstream. The AVP protein is depicted by GenBank Accession No. NP_000481.2 (SEQ ID NO:10), encoded by NM_000490.4 (SEQ ID NO: 25).

According to some embodiments of the invention, a vasopressin analogue is an AVPR1A (Arginine Vasopresin Receptor 1A) agonist.

Known analogues of Vasopressin include, but are not limited to 1-Desamino-8-D-AVP (DDAVP), Relcovaptan (SR-49059), and Oxytocin.

Vasopressin and analogues thereof can be obtained from various manufacturers or suppliers such as SIGMA-ALDRICH® (MERCK), ProSpec-Tany TechnoGene Ltd., Toronto Research Chemicals and Santa Cruz Biotechnology, Inc.

According to some embodiments of the invention, the Vasopressin in the second stimulus is provided at a concentration range of at least 1 pM (picomolar), e.g., at least 10 pM, e.g., at least 100 pM, e.g., at least 200 pM, e.g., at least 300 pM, e.g., at least 400 pM, e.g., at least 500 pM, e.g., at least 600 pM, e.g., at least 700 pM, e.g., at least 800 pM, e.g., at least 900 pM, e.g., at least 1000 pM, e.g., about 1 nM, e.g., at least 2 nM, e.g., at least 5 nM, e.g., at least 10 nM, e.g., at least 20 nM, e.g., at least 100 nM and no more than about 1000 nM.

According to some embodiments of the invention, the maximal value of the second stimulus comprises vasopressin at a concentration of about 1 nM (e.g., 1 nM).

According to some embodiments of the invention, the concentration of Vasopressin in the second stimulus does not exceed 1000 nM.

Leptin is a protein hormone that is secreted by white adipocytes into the circulation and plays a major role in the regulation of energy homeostasis. Circulating leptin binds to the leptin receptor in the brain, which activates downstream signaling pathways that inhibit feeding and promote energy expenditure. The leptin protein has the amino acid sequence as depicted by GenBank Accession No. NP_000221.1 (SEQ ID NO: 29), encoded by GenBank Accession No. NM_000230.3 (SEQ ID NO: 30).

According to some embodiments of the invention, a leptin analogue is a leptin Receptor (LEP-R) agonist.

A non-limiting example of a leptin analog is metreleptin (Rx).

Leptin or an analogue thereof can be obtained from various manufacturers and suppliers such as SIGMA-ALDRICH® (MERCK), R&D SYSTEMS, ThermoFisher SCIENTIFIC and PEPROTECH®.

According to some embodiments of the invention, the leptin in the second stimulus is provided at a concentration range of at least 1 ng/ml, e.g., at least 2 ng/ml, e.g., at least 5 ng/ml, e.g., at least 10 ng/ml, e.g., at least 20 ng/ml, e.g., at least 50 ng/ml, e.g., at least 100 ng/ml, e.g., at least 120 ng/ml, e.g., at least 130 ng/ml, e.g., at least 140 ng/ml, e.g., at least 150 ng/ml, e.g., at least 160 ng/ml, e.g., at least 170 ng/ml, e.g., at least 180 ng/ml, e.g., at least 190 ng/ml, e.g., at least 200 ng/ml (e.g., about 200 ng/ml, e.g., 200 ng/ml), e.g., at least 250 ng/ml, e.g., at least 300 ng/ml, and no more than about 1000 ng/ml.

According to some embodiments of the invention, the maximal value of the second stimulus comprises leptin at a concentration of about 200 ng/ml.

According to some embodiments of the invention, the concentration of leptin in the second stimulus does not exceed 1000 ng/ml.

Any of the proteinaceous factors used by the method of some embodiments of the invention (e.g., the insulin, Fibroblast growth factor 21, adiponectin, growth hormone, ghrelin, prolactin, TSH, and vasopressin) can be recombinantly expressed or biochemically synthesized. In addition, naturally occurring proteinaceous factors such as insulin, Fibroblast growth factor 21, adiponectin, growth hormone, ghrelin, prolactin, TSH, and vasopressin can be purified from biological samples (e.g., from human serum, cell cultures, hormonal glands, brain tissue) using methods well known in the art. It should be noted that for the preparation of an animal contaminant-free culture medium the proteinaceous factor is preferably purified from a human source or is recombinantly expressed.

Biochemical synthesis of the proteinaceous factors of the present invention (e.g., the insulin, Fibroblast growth factor 21, adiponectin, growth hormone, ghrelin, prolactin, TSH, and vasopressin) can be performed using standard solid phase techniques. These methods include exclusive solid phase synthesis, partial solid phase synthesis methods, fragment condensation and classical solution synthesis.

Recombinant expression of the proteinaceous factors of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Methods of synthesizing the steroid hormones such as cortisol, testosterone, Thyroxine (T4) are known in the art.

As described, the cells are exposed to a continuous flow of medium (also referred to as a "culture medium").

As used herein the phrase "culture medium" refers to a liquid substance used to support the growth of cells. The culture medium can be a water-based medium which includes a combination of substances such as salts, nutrients, minerals, vitamins, amino acids, nucleic acids, proteins such as cytokines, growth factors and hormones, all of which are needed for cell metabolism and optionally for proliferation and/or differentiation of the cells while in culture.

According to some embodiments of the invention, the culture medium is serum free, i.e., devoid of any serum.

According to some embodiments of the invention, the culture medium is xeno-free.

The term "xeno" is a prefix based on the Greek word "Xenos", i.e., a stranger. As used herein the phrase "xeno-free" refers to being devoid of any components/contaminants which are derived from a xenos (i.e., not the same, a foreigner) species.

According to some embodiments of the invention, the culture medium is a low serum culture medium. The serum can be of the same species as the species of the cells, or can be of a different species.

According to some embodiments of the invention, the serum is human serum.

According to some embodiments of the invention, the culture medium comprises less than 10% serum, e.g., less than 9%, less than 8%, less than 7%, less than 6%, less than 5%, less than 4%, less than 3%, less than 2%, less than 1%, less than 0.5%, 0.1% serum.

According to some embodiments of the invention, the culture medium comprises serum replacement.

As used herein the phrase "serum replacement" refers to a defined formulation, which substitutes the function of serum by providing cells with components needed for growth and viability.

Various serum replacement formulations are known in the art and are commercially available.

For example, GIBCO™ Knockout™ Serum Replacement (Gibco-Invitrogen Corporation, Grand Island, N.Y. USA, e.g., Catalogue No. 10828028) is a defined serum-free formulation optimized to grow and maintain undifferentiated ES cells in culture. Another commercially available serum replacement is the B27 supplement without vitamin A which is available from Gibco-Invitrogen, Corporation, Grand Island, N.Y. USA, e.g., Catalogue No. 12587-010. The B27 supplement is a serum-free formulation which includes d-biotin, fatty acid free fraction V bovine serum albumin (BSA), catalase, L-carnitine HCl, corticosterone, ethanolamine HCl, D-galactose (Anhyd.), glutathione (reduced), recombinant human insulin, linoleic acid, linolenic acid, progesterone, putrescine-2-HCl, sodium selenite, superoxide dismutase, T-3/albumin complex, DL alpha-tocopherol and DL alpha tocopherol acetate.

According to some embodiments of the invention, the serum replacement is devoid of (completely free of) animal contaminants. Such contaminants can be pathogens which can infect human cells, cellular components or a-cellular components (e.g., fluid) of animals.

For example, a xeno-free serum replacement for use with human cells (i.e., an animal contaminant-free serum replacement) can include a combination of insulin, transferrin and selenium. Additionally or alternatively, a xeno-free serum replacement can include human or recombinantly produced albumin, transferrin and insulin.

Non-limiting examples of commercially available xeno-free serum replacement compositions include the premix of ITS (Insulin, Transferrin and Selenium) available from Invitrogen corporation (ITS, Invitrogen, e.g., Catalogue No. 51500-056); Serum replacement 3 (SR3; Sigma, e.g., Catalogue No. 52640) which includes human serum albumin, human transferring and human recombinant insulin and does not contain growth factors, steroid hormones, glucocorticoids, cell adhesion factors, detectable Ig and mitogens; KnockOut™ SR XenoFree [e.g., Catalogue numbers A10992-01, A10992-02, part Nos. 12618-012 or 12618-013, Invitrogen GIBCO] which contains only human-derived or human recombinant proteins.

According to some embodiments of the invention, the ITS (Invitrogen corporation) or SR3 (Sigma) xeno-free serum replacement formulations are diluted in a 1 to 100 ratio in order to reach a ×1 working concentration.

Non-limiting examples of a culture medium which can be used include William's E basal media, DMEM, RPMI, and the like.

According to some embodiments of the invention, the culture medium is a defined culture medium.

As used herein the term "defined culture medium" refers to a culture medium which is man-made and all its components are known.

According to some embodiments of the invention, the culture medium includes a basal medium to which the first stimulus and the second stimulus are added in an oscillating manner.

It should be noted that the basal medium may include a hormone or an analogue thereof at a concentration which is below the predetermined threshold of the hormone or the analogue thereof in the first or second stimuli.

According to some embodiments of the invention the basal medium is composed of William's E basal media supplemented with bovine serum albumin (BSA), Insulin, Transferrin and Selenium (ITS) and glutamine.

An exemplary non-limiting basal medium includes: ALBUMIN BOVINE, FRACTION V [e.g., available from MP BIOMEDICALS, LLC., CA] at a concentration of about 3.75 mg/ml, 1× of ITS (e.g., available from Gibco™, MD), L-Glutamine [e.g., available from Biological Industries Israel Beit Haemek LTD., Israel] at a concentration of about 2 mM.

According to some embodiments of the invention, the cells are comprised in an organoid.

As used herein the term "organoid" refers to an artificial organ model (generated in vitro) comprising an aggregate of live cells in a three-dimensional or multi layered configuration manufactured by culturing cells in a three-dimensional form.

The organoid may have a suffix of "organ" and the meaning of 'similar to organ'. Organoids may comprise one differentiated cell type, or two or more differentiated cell types, depending upon the particular tissue or organ being modeled or emulated.

According to some embodiments of the invention, the organoid can carry out at least one function of the organ. According to some embodiments of the invention, the organoid is an organ model of a tissue such as liver, heart, brain, gut, kidney, bone or a cancer tumor, such as glioblastoma, hepatocellular carcinoma.

According to some embodiments of the invention, the organoid comprises hepatic cells.

According to some embodiments of the invention, the organoid comprises hepatic cells and endothelial cells.

According to some embodiments of the invention, the hepatic cells are of a hepatic cell line.

According to some embodiments of the invention, the hepatic cells are primary human hepatocytes (freshly isolated human hepatocytes).

According to some embodiments of the invention, the hepatic cells are E6/E7$^{low}$ human hepatocytes, e.g., as described in Levy G., et al., Nat Biotechnol. 2015 December; 33(12):1264-1271, which is fully incorporated herein by reference.

According to some embodiments of the invention, the hepatic cells are the Upcyte® Hepatocytes, which are expanded primary cells, derived from single donor primary cells available from Upcyte® Technology.

According to some embodiments of the invention, the endothelial cells are microvascular endothelial cells (e.g., human or rodent).

According to some embodiments of the invention, the organoid further comprises fibroblasts.

According to some embodiments of the invention, the organoid comprises enterocytes.

According to some embodiments of the invention, the organoid comprises LGR5+ (Leucine-rich repeat-containing G-protein coupled receptor 5 positive) gut stem cells.

According to some embodiments of the invention, the organoid comprises enterocytes and LGR5+ gut stem cells.

According to some embodiments of the invention, the organoid further comprises endothelial cells.

According to some embodiments of the invention, the organoid comprises enterocytes and endothelial cells.

According to some embodiments of the invention, the organoid comprises cardiomyocytes and endothelial cells (e.g., capable of beating).

According to some embodiments of the invention, the cardiomyocytes are obtainable by differentiation of pluripotent stem cells (such as embryonic stem cells or induced pluripotent stem cells (iPS).

According to some embodiments of the invention, the organoid comprises pancreatic (beta cells) (e.g. can secrete insulin).

According to some embodiments of the invention, the organoid comprises pancreatic (beta cells), and endothelial cells.

According to some embodiments of the invention, the organoid comprises pancreatic (beta cells), endothelial cells and fibroblasts.

According to some embodiments of the invention, the organoid comprises neural cells (e.g. neural progenitors).

According to some embodiments of the invention, the organoid comprises neural cells (e.g. neural progenitors) and endothelial cells.

According to some embodiments of the invention, the neural progenitors can release a neurotransmitter.

According to some embodiments of the invention, the neural progenitor cells are obtainable by differentiation of induced pluripotent stem cells.

According to some embodiments of the invention, the organoid comprises renal cells.

According to some embodiments of the invention, the renal cells comprise primary human proximal tubular cells.

According to some embodiments of the invention, the renal cells comprise HK2 proximal tubular cells.

According to some embodiments of the invention, the organoid comprises mesenchymal stem cells.

According to some embodiments of the invention, the organoid comprises mesenchymal stem cells and hematopoietic stem cells.

According to some embodiments of the invention, the organoid comprises cancerous cells.

According to some embodiments of the invention, the organoid comprises glioblastoma cells.

According to some embodiments of the invention, the organoid comprises hepatocellular carcinoma cells. According to some embodiments of the invention, the cells form part of an isolated tissue in a cell culture.

According to some embodiments of the invention, the cells are human cells.

Reference is now made to FIG. 25 which is a schematic illustration of a cross sectional view of a system 10 suitable for sustaining a synchronized circadian rhythm in cells 12 of a cell culture, according to some embodiments of the present invention. System 10 comprises a fluidic device 14 having culture wells 16 for holding the cells 12. Wells 16 are preferably microwells.

The term "microwell" as used herein, generally refers to a material having a fluid depression with at least one internal cross-sectional dimension that is less than 1 mm, more preferably less than 500 µm, more preferably less than 400 µm, more preferably less than 300 µm, more preferably less than 200 µm, e.g., about 100 µm or about 10 µm. Typically, but not necessarily a microwell has a volume of less than 1 mL.

In some embodiments of the present invention one or more of wells 16 (preferably each of wells 16) has a width of from about 0.8 mm to about 1.8 mm, and a height of from about 0.4 mm to about 0.8 mm.

One or more of wells 16 (preferably each of wells 16) can optionally and preferably comprise a matrix for culturing cells thereon. The matrix can be, for example, in a form of gel. In some embodiments of the present invention the matrix comprises collagen, and in some embodiments of the present invention the matrix comprises basement membrane gel, such as, but not limited to, Matrigel®.

System 10 can also comprise one or more, more preferably two or more, inlets 18 for receiving a base culture medium and optionally and preferably also hormones. The hormones and a base culture medium can include any of the hormones and base culture media referred to herein. Shown in FIG. 25 are three inlets 18, which can be used in some embodiments of the present invention for respectively receiving a first hormone, a second hormone and base culture medium, but any number of inlets can be used. System 10 can also comprise one or more fluidic channels 20 for establishing fluid communication between inlets 18 and wells 16. Optionally and preferably channels 20 are microchannels.

The term "microchannel" as used herein refers to a fluid channel having cross-sectional dimensions the smallest of which being less than 1 mm, more preferably less than 500 μm, more preferably less than 400 μm, more preferably less than 300 μm, more preferably less than 200 μm, e.g., about 100 μm or about 10 μm.

Channels 20 can include a linear microchannel extending along a generally (e.g., within deviation of 10% or less) straight line, or a nonlinear microchannel, in which case at least part of channel 20 extends along a curved line. Channels 20 can alternatively or additionally include a plurality of interconnected segments. These embodiments include a configuration in which all the segments are linear, or configuration in which all the segments are nonlinear, or a configuration in at least one of the segments is linear and at least one of the segments is nonlinear.

FIG. 25 illustrates several inlets 18 are in fluid communication with the same channel 20. This embodiment is useful in when it is desired to allow two or more types of media (hormones, base culture medium) to flow to the wells via the same channel. For example, the media can be delivered from inlets 18 to a mixing chamber 26 at which the media are mixed to provide a mixture that is delivered by chamber 26 to fluid channel 20. Alternatively, channel 20 can by itself serve as a mixer that mixes the fluids from the inlets to provide a mixture that is delivered by channel 20 to the wells 16. However, it is not necessary for several inlets 18 to be in fluid communication with the same channel 20. For some applications, it may be desired to have a system in which two or more of the inlets 18 feed separate fluid channels 20 so that at least one of the fluid channels does not receive a fluid from at least one of the inlets. Also contemplated are embodiments in at least two inlets 18 are in fluid communication with the same channel 20, and two inlets 18 feed separate fluid channels 20.

Channel(s) 20 provide the base medium and optionally and preferably the hormones, or mixture thereof, to wells 16 via one or more fluid communication ports generally shown at 22.

In some embodiments of the present invention system 10 also comprises one or more outlets 24 for evacuating fluid from wells 16 to ensure circulation of fluids through the wells 16. Evacuation of fluid can be established by generating an under-pressure at outlet 24, for example, by means of a controllable flow control system 34 including a positive displacement pump and an arrangement of valves (not shown), that ensures delivery and evacuation of fluids to or from wells 16. Flow control system 34 is optionally and preferably in fluid communication with one or more, more preferably two or more, more preferably three or more, reservoirs 42, each optionally and preferably holding a different fluidic media (hormone, gas, culture medium).

Typically, but not necessarily, the fluidic channels and inlet(s) and outlet(s) are formed or integrated on a separate chip from culture wells 16. These chips are shown at 28 and 30, respectively. In these embodiments, a sealing member 32 is optionally and preferably disposed peripherally over chip 30, between chip 30 and chip 28.

Chip 28 can be made of one or more thermoplastic polymers.

As used herein, the term "thermoplastic" refers to a polymer which is sufficiently soft above a certain temperature so as to readily allow plastic deformation of the polymer, and which is sufficiently stiff below a certain temperature so as to retain a desired shape. The softening of a thermoplastic polymer often occurs at temperatures near and/or above a transition temperature (e.g., a glass transition temperature, a melting point) of the polymer. Such a transition temperature may be determined, for example, by calorimetry.

Representative examples for thermoplastic polymers which can be used for chip 28 include, without limitation, acrylonitrile butadiene styrene, acrylic, celluloid, cellulose acetate, ethylene-vinyl acetate, ethylene vinyl alcohol, fluoroplastics, ionomers kydex, a trademarked acrylic/PVC alloy, liquid crystal polymer, polyacetal, polyacrylates, polyacrylonitrile, polyamide, polyamide-imide, polyaryletherketone, polybutadiene, polybutylene, polybutylene terephthalate, polyethylene terephthalate, Polycyclohexylene Dimethylene Terephthalate, polycarbonate, polyhydroxyalkanoates, polyketone, polyester polyethylene, polyetheretherketone, polyetherimide, polyethersulfone, polysulfone polyethylenechlorinates, polyimide, polylactic acid, polymethylpentene, polyphenylene oxide, polyphenylene sulfide, polyphthalamide, polypropylene, polystyrene, polysulfone, polyvinyl chloride, polyvinylidene chloride, and spectralon. In a preferred embodiment, the receptive material is polyetherimide, e.g., ULTEM™.

Also contemplated, are embodiments in which chip 28 is made, at least in part from an elastomer, such as, but not limited to, polydimethylsiloxane, gelatin, agarose, polyethylene glycol, cellulose nitrate, polyacrylamide or chitosan.

Chip 30 including its fluidic components (channels 20, ports 22, etc.) can be conveniently formed of a hardenable fluid, facilitating formation via molding (e.g., replica molding, injection molding, cast molding, etc.). The hardenable liquid can be essentially any liquid that can be induced to solidify, or that spontaneously solidifies, into a solid capable of containing and/or transporting fluids contemplated for use in and with a microfluidic system. In one embodiment, the hardenable liquid comprises a polymeric liquid or a liquid polymeric precursor. Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

In some embodiments of the invention silicone polymers are used. A representative example includes the silicone elastomer PDMS, which is commercially available, e.g., from Dow Chemical Co., Midland, Mich. Silicone polymers including PDMS have several beneficial properties simplifying formation of the channels 20. For instance, such materials are inexpensive, readily available, and can be solidified from a liquid polymeric precursor via curing with heat. PDMSs are typically curable by exposure of the liquid polymeric precursor to temperatures of about 70° C. for exposure times of about an hour. Elastomeric polymer materials are also advantageous for their inertness to critical components of an analysis or synthesis to be carried out.

In some embodiments of the present invention a temperature control system 40 configured for varying the temperature of cells 12 and/or one or more of the media delivered to cells 12. The temperature control system 40 can provide or extract heat from chip 30 and/or chip 28 by means of convection, conduction or radiation. In the illustration of FIG. 25, which is not to be considered as limiting, temperature control system 40 is illustrated as being in direct thermal communication (convective, conductive or radiative) with chip 30 from below, thereby facilitating delivery or extraction of heat to or from wells 16 via the material from which chip 30 is made. However, this need not necessarily be the case, since, for some applications, it may be desired to provide convective, conductive or radiative thermal communication between system 40 and chip 28. In these embodiments, system 40 can be placed above chip 28, facilitating delivery or extraction of heat to or from wells 16 via the material from which chip 28 is made.

Also contemplated, are embodiments in which system 40 is within chip 28, shortening the thermal path between system 40 and wells 16. For example, system 40 can be formed at the surface 38 of chip 28 that paces chip 30, facilitating delivery or extraction of heat to or from wells 16 not via the material from which chip 28 is made. Further contemplated, are embodiments in which system 40 is positioned to deliver or extract heat to or from channels 20, and/or to or from mixing chamber 26, and/or to or from inlets 18, and/or to or from port 22, in which the variation of the temperature of cells 12 is by heat convection effected by the flow within channels 20. Additionally contemplated, are embodiments in which system 40 is a component within flow control system 34, whereby heat is delivered to or extracted from the media provided by system 34 to channels 20.

Temperature control system is preferable controllable by control signals, and can include any heating element, such as, but not limited to, a resistive heating element, an infrared lamp or the like.

System 10 preferably also comprises a controller 36 having a circuit, optionally and preferably a dedicated circuit, configured for executing the method described herein. Preferably, controller 36 is a computerized controller. More preferably, controller 36 is a computerized controller having dedicated circuit. Typically, controller 36 transmits operating signals to flow control system 34 to generate flow in channels 20 according to a protocol programed into the circuit of controller 36. Preferably, controller 36 ensures that wells 16 receive a continuous flow of the culture medium, and a periodic flow of fluids (hormones, gas) that stimulate the cells 12.

In some embodiments of the present invention controller 36 signals flow control system 34 to effect a single path flow for the culture medium. In these embodiments, culture medium that is evacuated by system 34 via outlet 24 is discarded. In some embodiments, controller 36 signals flow control system to effect closed fluidic path flow for the culture medium. In these embodiments, culture medium that is evacuated by system 34 via outlet 24 is redirected by system 34 into one of the inlets 18. Combination of these embodiments, wherein during some time periods the culture medium is discarded and in other time period the culture medium is redirected into one of the inlets 18, is also contemplated according to some embodiments of the present invention.

In some embodiments of the present invention controller 36 signals flow control system 34 to vary the relative amounts of the hormones and the base culture medium, while maintaining constant flow of the medium. This is optionally and preferably executed by system 34 by varying the relative amounts of media entering system 34 from reservoirs 42.

In some embodiments of the present invention controller 36 transmits control signals to temperature control system 40, to ensure variation of the temperature of the cells 12 (either via the chips 28 and/or 30, or by varying the temperature of the media provided by channel 20, as further detailed hereinabove) according to a protocol programed into the circuit of controller 36. Preferably, controller 36 transmits to system 40 control signals that effect temperature oscillation of cells 12. For example, controller 36 can transmit to system 40 control signals that effect periodic oscillation between a first temperature and a second temperature. Typically, but not necessarily, the first temperature is lower than second temperature, with a non-zero temperature difference of less than about 1° C.

In a representative protocol employed by system 10, controller 36 signals flow control system 34 to provides in an oscillating manner a first fluid and a second fluid as two separate and stimuli to the cells, wherein the first fluid is different from the second fluid, and wherein the periodicity of the oscillation is from about 20 hours to about 28 hours, e.g., 24 hours. The first fluid can be provided over a first time period and can reach a first peak that extends over a first peak time period, and the second fluid can be provided over a second time period and can reach a second peak that extends over a second peak time period. The interval between the end of the first peak time period and the beginning of the second peak time period is optionally and preferably at least 2 hours or at least 2.5 hours or at least 3 hours or at least 3.5 hours or at least 4 hours. It was found by the Inventors that such a protocol sustains the synchronized circadian rhythm in cells 12. Optionally, controller 36 signals temperature control system 40 to oscillate between the first temperature and the second temperature during the first and the second time periods, respectively.

MATRIGEL® (Becton Dickinson, USA) is a soluble preparation from Engelbreth-Holm-Swarm tumor cells that gels at room temperature to form a reconstituted basement membrane; MATRIGEL® is also available as a growth factor reduced preparation.

The repetitive day/night cycle introduces cyclical differences to the environment. Across all kingdoms, organisms developed a molecular clock circuits in order to anticipate and adapt to routine changes in the microenvironment. In higher organisms these molecular circuits are timed by circadian changes in hormone levels and metabolite abundance, predominantly affecting the liver that functions as the metabolic hub of the body. Furthermore, the circadian-metabolic axis exhibits reciprocal interaction as changes in metabolism can modify the circadian cycle, while disruption of the circadian rhythm can cause morbid alteration in metabolism. Disruption of the circadian-metabolic axis can lead to insulin resistance and metabolic syndrome, an emerging pandemic with 30% prevalence among non-diabetic populations. Regretfully, rodent models differ from humans in their physiology and show an inverted day/night cycle, while human in vitro models are usually static and do not exhibit circadian changes. Therefore, there is a great need to establish reliable, robust and sustainable human circadian liver models to enable study of these diseases. The present inventor employed the E6/E7$^{low}$ human hepatocytes that are metabolically comparable to cryopreserved human hepatocytes and has integrated E6/E7$^{low}$ hepatocytes and endothelial co-cultures into a microfluidic liver organoid-on-a-chip model. These organoid cultures are subjected to circadian hormone and temperature rhythms, thus creating a novel, robust, and sustainable circadian human liver model. Utilizing this platform, the present inventor recapitulates circadian transcriptional and metabolic profiles of the human liver and unveils the master regulators involved in circadian-metabolic physiology. This platform is also beneficial for assessment of new therapeutics that directly affect circadian-metabolic axis.

The emerging development of the microfluidics field provides a good solution for the drawbacks of human static tissue cultures. Microfluidics were already used to circulate nutrients [46]. However, the present inventor has incorporated circadian hormonal cues into microfluidic liver organoid-on-a-chip model, thus creating a novel, robust, and sustainable circadian human liver model. Using the recently characterized E6/E7$^{low}$ human hepatocytes (Upcyte® Hepatocytes, Upcyte Technologies GmBH) that demonstrate proliferative capacity, while preserving high levels of metabolic activity, mainly relaying on oxidative-phosphorylation [47], the model fully recapitulates the circadian metabolic profile of a human liver. The model is beneficial for assessment of chronotoxicity of existing drugs, while serving as a platform for new therapeutics that directly affect the rhythmic-metabolic pathways.

In this project, the oscillation of temperature, hormones, and other entrainment factors is controlled, capturing extra-hepatic synchronization of circadian rhythms in human micro-livers. Importantly, oxygen uptake is measured in real-time by infrared microspectroscopy to monitor the metabolic state of living cells non-invasively, and by tracking metabolic changes in bioreactor outflow using mass spectroscopy. Thus, the self-assembled human liver organoids cultured under conditions mimicking physiological dynamics reproduce the regulatory complexity observed in vivo.

Thus, the advanced Liver-on-Chip model reproduces the complexity of physiological rhythms, while permitting an unparalleled real-time measurement of metabolic dynamics. This model presents a quantum leap in capability, offering the opportunity to replace animal models in chronic toxicity studies (i.e. repeated dose response), unravelling the regulatory complexity of nutritional events (e.g. night shift workers diet), and providing new information for chronopharmacology.

Thus, self-assembled organoids are cultured in microwell bioreactors under circadian oscillations of temperature and hormones. Oscillations of these entrainment factors synchronizes cells and drives physiological rhythms on the transcriptional, proteome, and functional levels. Recently, the present inventor showed that the real-time measurement of oxygen uptake using oxygen nanosensors coupled with electrochemical monitoring of glucose and lactate, enables the detection of sub-threshold effects of toxins shifting mitochondrial respiration to glycolysis (Prill S., et al, 2016, Supra). Here, the present inventor utilizes the platform to monitor circadian rhythms and elucidate changes in central carbon metabolism along the circadian cycle. The physiological cues are uncoupled from the cell-autonomous clock by step-wise subtraction.

The present inventor uses a microfluidic switchboard permitting rapid sample and recovery cycles for continuous sampling of multiple bioreactors. The present inventor has uncovered that using a dual-labelled pulsed stable-isotope resolved metabolomics (pSIRM) to track differential citrate $^{13}C$ labelling due to minute changes in glycolysis, glutaminolysis or lipid peroxidation[13]. The integration of pSIRM with liver-on-chip provides insight into differential energy utilization during the circadian cycle allowing to link between gene expression and metabolic regulation. Importantly, the platform would provide dynamic information for chronopharmacology (e.g. ideal time to block cholesterol synthesis).

Thus, the FTIR microspectroscopy is utilized to non-invasively monitor key metabolic states of living cells. The key advantage is the high cell/liquid ratio in which bioreactors operate maximizing S/N of infrared measurements. Here, surface-enhanced Raman spectroscopy (SERS) is an alternative technique that is assessed in parallel. Water absorption and sample thickness play a smaller role in Raman than FTIR, but Raman is a weaker signal. Both microspectroscopy techniques have been primarily used in fixed samples. The ability of the system to monitor toxicological dynamics is validated using a list of characterized hepatotoxins developed for the SEURAT-1 cluster. Importantly, transient, sub-threshold effects of drugs that could provide critical information on each compound mechanism of action are identified.

The present inventor has envisaged the control of the oscillation of temperature, hormones, and other entrainment factors capturing extra-hepatic synchronization of circadian rhythms in self-assembled human micro-livers. This approach permits an unparalleled real-time computation of metabolic dynamics, allowing to focus on genetic manipulation and hormonal modulation that are impossible in vivo.

Liver-on-Chip: Animal research is a critical engine of discovery contributing to the safety and efficiency of many products. However, ethical considerations, transcriptional differences, and inverted day/night cycles, make metabolic predictions in murine models difficult at best. Microfluidics permit a precise and dynamic control of the cellular microenvironment allowing us to mimic physiological conditions in an in vitro setting[18]. Over the past decade, several research groups including the present inventor's research group demonstrated the long-term maintenance of hepatocyte function in a perfused bioreactor. Although bioreactor designs varied[19-22], results demonstrated the need to protect hepatocytes from the negative effects of shear forces exceeding 5 dyne/cm$^2$, while delivering oxygen at rates above 0.9 nmol/sec/10$^6$ cells. One example is LiverChip, a packed-bed design in which cells form liver-like tissue structures including hepatic, endothelial, and stellate components. Dipped oxygen probes permit monitoring of oxygen levels, albeit with low sensitivity, due to varying probe distance from the tissue. In contrast, the present inventor has designed a microwell reactor permitting maintenance of self-assembled human organoids for over 30 days under continuous perfusion. Stable gradients mimic the development of liver zonation, while embedded nanosensors permit precise measurement of oxygen uptake rate of each micro-tissue in real-time.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are

Example 1

Inducement of Physiological Rhythms in Liver-on-a-Chip with Real-Time Metabolic Flux Monitoring and Establishment of a Robust Circadian-Like Flow Pattern Rationale: The cell autonomous clock in liver cells is synchronized by daily oscillations in hormones and temperature. While in current approaches cells become desynchronized within 72 hours or less, here the present inventor uses microfluidics to match the oscillation of hormones and temperature in human plasma to synchronize oscillations indefinitely.

Methodology: Gamble K. L. and colleagues [48] and Skene D. J. and Arendt J. [3] reviewed the current literature and recent work by the groups of Irwin M. [49] Ross R. J. and others showed that melatonin, growth-hormone (GH), Triiodothyronine (T3), interleukin-6 (IL-6), adiponectin and cortisol oscillated in human plasma. The present inventor has uncovered that two predominant stimulation patterns appear. While melatonin, GH, T3 and IL-6 seem to peak during the night, cortisol and adiponectin show a peak toward the morning and show a slow decay toward the evening. Cortisol peaking in the early morning, GH and melatonin peaking in the middle of the resting period, i.e. night, and T3 peaking in between. Simplifying the patterns and grouping the hormones into "day" or "night" entraining factors, the present inventor has created a flow pattern that mimics the circadian physiology (FIG. 1A). A flow routine was designed and tested using a microfluidic-mixing chamber with the fluorescent dyes FITC and Rhodamine B for the night- and the day-peaking circadian patterns respectively. Measured signals suggest stable and robust circadian pattern (FIG. 1B).

The present inventor has uncovered that a bioreactor with three inputs should be able to simulate the observed hormonal and temperature patterns while maintaining constant shear forces across the system as shown in FIGS. 2A-D. To achieve this goal the present inventor designed day and night medium supplements. Basal medium is composed of William's E basal media supplemented with BSA, ITS and glutamine, while day medium is composed of basal medium supplemented with dexamethasone (a stable analog of cortisol). Finally, night medium is composed of basal medium supplemented with melatonin, GH and T3 (Table 1).

TABLE 1

| Component | Abbreviation | Final concentration | Product |
|---|---|---|---|
| Basal media | | | |
| ALBUMIN BOVINE, FRACTION V | BSA (bovine serum albumin) | 3.75 mg/ml | 02160069 (MP BIOMEDICALS, LLC., CA) |
| Insulin-Transferrin-Selenium (ITS -G) (100X) | ITS | 1X | 41400045 (Gibco ™, MD) |
| L-Glutamine Solution (200 mM) | Glutamine | 2 mM | 03-020-1B (Biological Industries Israel Beit Haemek LTD., Israel) |
| Day media supplements | | | |
| Dexamethasone-Water Soluble | Dexamethasone | 100 µM | D2915 (Sigma-Aldrich Co. LLC., MO) |
| Night media supplements | | | |
| Melatonin | — | 200 µM | M5250 (Sigma-Aldrich Co. LLC., MO) |
| HumanKine ® HGH, Human Recombinant Xeno-Free | GH (growth-hormone) | 30 ng/ml | GF415 (Merck Millipore, MA) |
| 3,3',5-Triiodo-L-thyronine sodium salt | T3 (triiodothyronine) | 10 nM | T5516 (Sigma-Aldrich Co. LLC., MO) |

Table 1. Media formulation. Component list of all three media that are used -basal media, day media and night media, including concentration and product catalogue numbers.

Next, the present inventor has designed and characterized a flow-control system capable of reproducing these patterns. The system uses a robust and precise air pressure controlled flow system (FLUIGENT) in order to create the required flow patterns that will correlate with human circadian rhythm as it is exhibited by the liver. Validation of oscillation is performed using fluorescent microscope measuring solution of 275 µM FITC and 1 µM Rhodamine B. Working with concentrated solution is essential in order to identify with good resolution between values during time periods with lower concentrations. FIGS. 1A and 1B, show respectively, the design of the simplified flow pattern and their realization inside a microfluidic chamber, using FITC and Rhodamine B, exhibiting patterns similar to those of the in vivo cues.

The present inventor has incorporated the flow control system with the previously developed liver-on-chip platform. This platform integrates real time monitoring of oxygen, lactate and glucose fluxes in the tissue while also enabling long term culturing of HepG2/C3A self-assembled spheroids (Prill S., et al., 2016. Arch Toxicol. 90(5):1181-91). Utilizing similar setup the present inventor monitors the oxygen uptake of liver organoids, exposed to circadian oscillating cues. Oxygen is known to be an entrainment factor of the circadian clock [4], thus raising hope to reveal the potential reciprocal connection between the two, as would be assumed due to differential metabolic activity during the cycle. In order to fully characterize the circadian central-carbon-metabolism profile of the human liver the present inventor performs metabolic flux monitoring in real time of glucose and lactate, as well as glutamine and glutamate, using microscale electrochemical sensors (Jobst Technologies GmbH) for combined measurement of all four. Data measurements is analyzed using metabolic flux analysis method, under the assumptions of steady state fluxes in the samples, minimal to none existing proliferation and limited nutrients available. First, fluxes are calculated by subtraction of outlet and inlet concentration from each other to either produce production or consumption rates. Later, balancing oxygen consumption with glucose provides oxidative-phosphorylation rate. Glutamine consumption is indicative for glutaminolysis, while excess lactate produced can be accounted as an outcome of glycolysis. Any excess of glucose consumed by the cells is referred to as part of the fatty acids anabolic processes, as consumption of glucose towards other pathways, as the pentose-phosphate (PPP) is negligible in none-proliferating cells. Based on sampling the metabolites over a course of a few days, and further analysis of the metabolic state of the cultures, the present inventor monitors the circadian output induced by the oscillating cues. Searching for cosine-like repeated metabolic state enables to confirm achievement of robust, sustainable circadian physiology.

Primary human hepatocytes do not proliferate in vitro and their hepatic-specific functions decline under conventional culture formats [51-53], on the other hand, while human hepatocellular-carcinoma lines proliferate in culture dedifferentiated and lost most liver specific metabolic functions [45, 54]. The present inventor has recently characterized several lines of E6/E7$^{low}$ human hepatocytes that are able to proliferate in culture (Upcyte® Hepatocytes), showing metabolic activity on par (Levy G., et al., Nat Biotechnol. 2015 December; 33(12):1264-1271) with cryopreserved primary cells and differentiated HepaRG cells [47]. Differentiated Upcyte® Hepatocytes preserve the natural metabolic functions of non-tumorigenic primary hepatocyte (i.e. oxidative-phosphorylation, normal urea cycle and drug metabolism). In a three-dimensional co-culture with endothelial cells Upcyte® Hepatocytes are capable of forming a functionally polarized liver organoid (FIGS. 3A-E).

The organoid containing liver-on-chip platform provides a reliable metabolic model of the human liver. This system supports studies of genetic based difference in- and idiosyncratic toxicity, as these cultures are derived from donors with different physiological states, gender, age and ethnic backgrounds (Table 2). Characterization of circadian rhythms in each background may reveal differential responses that coincide with the different background of each donor.

TABLE 2

| Donor background and characteristics | | | | | |
|---|---|---|---|---|---|
| Donor | 653 | 740 | 10 | 151 | 422A |
| Ethnicity | Caucasian | Asian | Caucasian | Caucasian | Hispanic |
| Gender | Female | Female | Female | Female | Male |
| Age (years) | 9 | 6 | 48 | 43 | 0.25 |
| UGT | 33 | 145 | 155 | 142 | 96 |
| SULT | 7 | 11 | 4 | 3 | 6 |
| GST | 28 | 88 | 14 | 32 | 20 |
| Serological analysis* | CMV+ | CMV+ | Negative | Negative | CMV+ |
| Viability | 82% | 85% | 83% | 75% | 96% |
| Cause of death | Anoxia | Head trauma | N/A | N/A | Anoxia |
| Alcohol use | No | N/A | N/A | Yes | No |
| Smoker | No | N/A | N/A | Yes | No |
| Body mass index | 17.5 | N/A | N/A | 22.7 | 15 |
| Drug use | No | N/A | N/A | No | No |
| Prescription medication | No | N/A | N/A | No | No |
| CYP3A4 Activity | 22 | 7.1 | 41.7 | 44 | 61.7 |
| Cyp3A4 Induction | x6.5 | x1.8 | x8.2 | x2.3 | x3.1 |

Table 2. Donor background and characteristics. UGT, UDP-glucuronosyltransferase activity (pmol h$^{-1}$ mg$^{-1}$ cellular protein); SULT, sulfotransferase activity (pmol h$^{-1}$ mg$^{-1}$ cellular protein); GST, glutathione-S-transferase activity (nmol h$^{-1}$ mg$^{-1}$ protein); N/A, data not available.
*Serologic analysis was performed for cytomegalovirus (CMV), hepatitis B virus and hepatitis C virus.

Human liver organoids are established in microwell bioreactors (FIGS. 8A-C and 10A-E) and exposed to microfluidic oscillations of hormones, temperature, and entrainment factors. Oxygen uptake is monitored in real-time using OPAL (FIGS. 11A-E) and outflow samples is collected for metabolic analysis. Following stabilization, organoids are harvested every 4 hours for transcriptomic, metabolomic, and proteomic analysis for 3 days. This data is used to construct a dynamic network of metabolic fluxes and their associated transcriptional regulators (FIGS. 16A-F). Results are compared to publically available rodent data sets as well as previously published human plasma results[23]. Upcyte hepatocytes (FIGS. 12A-I and 13A-B) are used and critical findings are validated in freshly isolated human hepatocytes (FIGS. 8A-C).

Example 2

Studying the Circadian Transcriptome of the Human Liver

Rationale: Metabolism is fundamentally controlled on the transcriptional level by a family of hormone and metabolite activated transcription factors called nuclear receptors [55]. To identify time dependent changes in nuclear receptors activity the present inventor actively looks for metabolic regulators as a function of time, in differentially expressed metabolic pathways. The present inventor obtains the transcriptional signature of human liver under sustained oscillation and identifies genes whose expression peaks during day or night cycles as a function of metabolic pathway.

Methodology: The present inventor performs full analysis of the circadian transcriptome of the liver by RNA sequencing. Liver organoids subjected to circadian oscillation, are sampled for mRNA extraction every four hours over a course of 3 days. Library preparation and RNA sequencing are performed at the Hebrew University Center for Genomic Technologies. Library construction is conducted using Illumina TruSeq RNA Library Prep V2 Kit (Illumina, San Diego, Calif.) and sequenced on Illumina NextSeq500 with single-end, 86 bp reads using the NextSeq500 High Output V2 Kit (Illumina, San Diego, Calif.). This method is very efficient and simple for standard transcriptome analysis [56]. Experiments provide the first transcriptional data from human in vitro liver tissue, under robust and sustained state of circadian cycling.

Full transcriptome is screened for circadian gene expression, using simple cosine curve fitting, that is thought to be comparable to JTK_CYCLE, as described by Robles, M. S and colleagues [10, 11]. Genes exhibiting circadian expression pattern, are first clustered according to phase of peak. Genes that peak either during the "day" or the "night" phases are further clustered for enrichment in metabolic categories or pathways, including oxidative Stress and nitrogen, glucose, lipid, cholesterol and drug metabolism [55] and also specifically aromatic amino acid metabolism and purine and pyrimidine metabolism, via the PPP. This allows full circadian-metabolic pathway characterization. Comparison to previously reported murine data sets [11, 12, 35, 57, 58] and available human metabolic measurements [59] is performed.

To further distinguish between core-clock controlled metabolic pathways and externally entrained circadian metabolic pathways, ΔCLOCK deficient cell lines are created, with inhibited oscillation of the internal clock. The cells are generated using CRISPR genome editing technology [60] to produce a knockout cell line. In short, cells are transfected with a mixture of Clock CRISPR/Cas9 knockout plasmids, already containing guide-RNA (Clock CRISPR/Cas9 KO Plasmid (h), Santa Cruz Biotechnology, Inc., Dallas, Tex.). Later the samples are sequenced, first searching for editions in the guidRNA complementary site and secondly for editions in off targets, thus double-selected for colonies that underwent successful single transfection. Knockout cell lines subjected to circadian oscillation are characterized metabolically, and on transcriptomic level, as described above. The WT-knockout data sets are compared, searching for transcripts that start to or fail to exhibit a circadian pattern. This reveals the metabolic response and the gene sets that are coordinated either by the cellular internal clock or by the external cues. Comparison to previously reported murine data sets [11, 12, 35, 57, 58] and available human metabolic measurements [59] is performed. This allows to identify differentially up- or down-regulated pathways suggesting internal clock controlled metabolic pathways.

Collect Samples for Transcriptomic, Metabolomics, and Proteomic Analysis

Real-time oxygen uptake measurements are taken every 15-30 minutes using the OPAL system for 7 days past metabolic stabilization (FIGS. 11A-E). Measurements are carried out by averaging 5×3 second exposures, followed by 17 second intervals, for a total of 100 seconds. Oxygen and albumin secretion are used to evaluate metabolic stabilization (about 3 to 5 days). Samples are collected automatically every hour from bioreactor outflow. ELISA is used to measure albumin and ApoB100 secretion as well as an unbiased metabolome analysis using LC-MS/MS (AB Sciex QTRAP 5500 @ Core Facility) followed by a targeted analysis, as needed, to quantify glucose, lactate and citrate in perfusate. A key advantage of microfluidics is a high cell/volume ratio offering an excellent S/N for this type of analysis.

Once metabolic function is stabilized, cell lysates are collected every 4 hours for 3 days and stored at −80° C. Samples are split for three types of analysis: RNA-Seq analysis (NextSeq 500 @ Core Facility), unbiased metabolome analysis using LC-MS/MS (AB Sciex QTRAP 5500 @ Core Facility), and tandem LC-MS shotgun proteome analysis combined with SILAC at Prof. Stefan Kempa facility (MDC, Berlin).

Example 3

Uncovering Master Regulators of Circadian Rhythm in the Liver

Rationale: Nuclear receptors (NRs) are master regulators of cellular metabolism. Recent work by Evans R. M. group showed that more than 50% of nuclear receptors showed circadian patterns in the mouse liver [61]. Identifying such master regulators in human liver cells would unveil major players in circadian physiology, providing new therapeutic targets to treat circadian abnormalities.

Methodology: Targeted mass spectrometry (MS) analysis is performed to characterize the circadian metabolome. Based on the sequencing data the two peaks of day and night clustered genes are identified. Samples providing the metabolic signatures of the day and the night are collected, as each sample is collected 1-2 hr after the peak of transcription, to enable steady metabolic state to establish in the cells. Samples are tested both for the intra- and extra-cellular metabolic content, enabling identification of fluxes as well. Shortly, samples are extracted using the classic methanol/chloroform/water method with tissue disruption in methanol followed by bi-phasic partitioning in chloroform/water mixture [62]. The polar, water soluble, fraction is mainly tested, evaluating metabolites of the central carbon metabolism pathways using LC-MS/MS [63]. The non-polar, chloroform soluble, fraction is also tested using LC-MS/MS, if required, to identify circadian changes in abundance of different fatty acids [57]. Data is analyzed for enrichment of specific metabolites in each time-clustered group, compared to standard reference metabolome, then, up- and down-regulated metabolites are clustered for pathways using Metabolite Set Enrichment Analysis/MESA (OMICtools), creating metabolic maps. This assay is performed on both co-culture of organoid containing WT and ΔCLOCK hepatocytes, for the purpose of identifying the metabolic changes that are directly controlled by the internal clock and those that can be entrained externally.

The overlapping of the mRNA sequencing and the metabolic maps is analyzed to identify the key regulators of the metabolic pathways that are being up- or down-regulated during the circadian cycle. In the present inventor's previous work [55], it was found that NRs, a family of ligand-activated transcription factors, induce a reprograming of metabolic pathways of the cells, as a response to viral infection. Furthermore, work by Evans R. M. group revealed that more than 50% of the NRs are subjected to daily oscillatory transcription patterns [61]. Based on these findings, the present inventor has proposed that nuclear receptors plays a key role in the adjustments of the metabolic state of cells during the circadian cycle in a similar way [11, 12, 35, 57, 58]; either directly by exhibiting oscillatory circadian expression pattern [61] or due to circadian oscillation of their activating ligands [12]. Following the identification of putative major regulators of circadian metabolism, these transcriptional-metabolic pathways are validated by utilizing the GFP activity reporter library. The library was constructed by cloning multiple repeats of DNA response elements upstream of a minimal CMV promoter with destabilized copGFP, with super-fast maturation (1.5 hrs) and short half-life (2 hrs) downstream. Transcription factor activation results in direct copGFP transcription, measuring transcriptional activity. Small molecules are used to either inhibit or induce activity of the putative major regulators (Table 3) and then correlate the transcriptional activity measured by the reporter and the induced metabolic state [55]. In addition, the transcriptional activity of these putative major regulators during the circadian cycle is correlated by subjecting reporter encoding organoids to circadian oscillation and real time, live measurement of their activation. Again, to enable distinguishing external effects from internal effects, WT and ΔCLOCK cell containing organoids are tested, and compared.

TABLE 3

| Name | Abbreviation | Symbol | Natural ligands | Agonists | Antagonists |
| --- | --- | --- | --- | --- | --- |
| Constitutive androstane receptor | CAR | NR1I3 | Xenobiotics | CITCO, Androstane, Phenobarbital (indiret) | |
| Hepatocyte nuclear factor 4 alpha | HNF4α | NR2A1 | Fatty acids | | Medical6, BI 6015, bezafibrate, Compound 5 |
| Retinoid X receptor | RXRα | NR2B1 | 9-cis retinoic acid and docosahexanoic acid | CD 3254 | |
| Farnesoid X receptor | FXR | NR1H4 | Bile acids | GW4064, Fexaramine, XL335, INT-747 | BML-GR235, Guggulsterone, 80-574 |
| Peroxisome proliferator-activated receptor alpha | PPARα | NR1C1 | Fatty acids | Fenofibrate, GW7647, CP-775146 | GW9662 (partial) |
| Peroxisome proliferator-activated receptor gamma | PPARγ | NR1C3 | Fatty acids | Prostaglandin J2, GW7845, GW1929, WY-14643, Thiazolidinediones (Rosglitazone, Inolitazone, ciglitazone and troglitazone) | GW9662 |
| Pregnane X receptor | PXR | NR1I2 | Xenobiotics | Rifamycin, Rifaximin, Fexaramine, Guggulsterone, PCN | Silibilin |
| Aryl Hydrocarbon Receptor | AHR | AHR | Xenobiotics | Leflunomide, ITE, FICZ | 6,2',4'-Trimethoxyflavone, CH-223191, StemRegenin 1 |
| Liver X receptor alpha | LXRα | NR1H3 | Oxysterols | GW3965, LXR-623, T0901317 | GSK2033 (17), 22S-HC, 22R-HC |
| Sterol Regulatory Element Binding Transcription Factor 1 | SREBP1 | SREBF1 | | Insulin (serum staravtion induction) | |
| Sterol Regulatory Element Binding Transcription Factor 2 | SREBP2 | SREBF2 | | Insulin (serum staravtion induction) | |
| Chicken Ovalbumin Upstream Promoter-Transcription Factor | COUP | NR2F | | | |
| Estrogen receptor | ESR1 | NR3A1 | 17β-estradiol, Estrogens | | Tamoxifen, Raloxifene, Lasofoxifene, Bazedoxifene, Fulvestrant |
| Retinoic Acid Receptor Alpha | RARα | NR1B1 | Retinoic acid | AGN 195183, Tamibarotene, AM580, BMS 753 | ER 50891, AGN 196996, BMS 195614 |

Table 3. Nuclear receptor list and their natural and synthetic agonists and antagonists. List of the nuclear receptors and few transcription factors regulating the central metabolic pathways. Marked in green are the transcription factors that have successfully constructed a copGFP activity reporter for their transcriptional activation. Natural ligands are usually agonists. Stated only synthetic agonists/antagonist with specificity.

Example 4

Organoid-on-a-Chip Microfluidic Platform

Based on the previously developed organoid-on-a-chip microfluidic bioreactors, already integrating real time oxygen flux monitoring [50], the present inventor has developed a multi-bioreactor platform. This platform allows to run several parallel experiments, increasing the throughput (FIGS. 2A-C). The present inventor has further incorporated the platform with a robust, air pressure controlled flow control by FLUIGENT. The present inventor has created three-input bioreactor that enables to simulate the observed hormonal patterns of human circadian rhythm. Real time monitoring of lactate, glucose, glutamine and glutamate fluxes was achieved by integrating the system to a novel off-the-shelf available sensor (IST AG LV5 sensor) by Jobst Technologies GmbH, for combined measurement of all four (FIG. 2D).

Example 5

Circadian Rhythms

The ability to respond to day/night cycles allows organisms to anticipate energy requirements and predict environmental conditions. In mammals, this circadian clock is controlled by the pacemaker neurons of the suprachiasmatic nucleus (SCN) that translate light/dark cycles to hormonal and nerve signalling, resetting cell-autonomous clocks throughout the body (FIGS. 3A-E). Cell-autonomous clocks are a transcriptional feedback loop in which CLOCK and BMAL1 bind E-box elements on PERiods and CRYptochromes self-inhibiting transcription[1]. This auto-regulatory loop is metabolically and post-transcriptionally regulated and controls the expression of 15% of the transcriptome and most plasma metabolites[2, 10]. Circadian rhythms are studied in mice using end-point assays that provide little dynamic information of unclear human relevance due to inverted day/night cycles and metabolic differences, while cell culture rhythms rapidly decay post-synchronization. The present inventor's approach relies on continuous microfluidic oscillation of hormones and temperature, inducing a steady circadian state that can be readily manipulated.

Model transcriptional and metabolic rhythms in sensor-integrated liver-on-chip—The present inventor's approach is to culture self-assembled organoids in physiological micro-well bioreactors under microfluidic oscillations of hormones, temperature, and entrainment factors (FIGS. 3A-E). Oxygen uptake is monitored in real-time and outflow is collected for metabolic analysis[4]. Organoids are sequentially harvested for single-cell RNA-Seq, clustered based on metabolic zonation phenotype, and sorted for metabolomic and proteomic analysis. This data is used to construct a dynamic network of metabolic fluxes and their associated transcriptional regulators based on their metabolic zonation. Results are compared to publically available rodent data sets as well as previously published human plasma results[10]. Both naïve and CRY1/2 knockout E6/E7$^{LOW}$ hepatocytes[5] are used, uncoupling physiological cues from the cell-autonomous clock by step-wise subtraction. This generates a model of stable physiological rhythms in human liver, and defines dynamic changes in the metabolic network and its transcriptional regulation during the day/night cycle.

Elucidate the effect fasting-to-feeding transition on circadian rhythm.

Night shift workers show increased risk for diabetes and obesity due to inverted feeding patterns. The present inventor's platform offers the ability to track the consequences of fast processes, such as insulin phosphorylation, operating on a slow-changing proteome landscape. The present inventor's approach is to introduce a glucose and insulin rich stimulus, mimicking breakfast, at different time points along the circadian rhythm. This introduction of nutritional dynamics provides critical data for chrono-pharmacology ranging from optimization of pharmaceutical interventions to insight into minimizing toxicological effects of current therapies.

Example 6

The ability to measure time and respond to day/night cycles allows organisms to anticipate energy requirements and predict environmental conditions. In mammals, this circadian clock is controlled by the pacemaker neurons of the suprachiasmatic nucleus (SCN) that translate light/dark cycles to hormonal and nerve signalling, resetting cell-autonomous clocks throughout the body[1, 11]. Cell-autonomous clocks are composed of a transcriptional feedback loop in which CLOCK and BMAL1 bind E-box elements on the promoters of PERiods and CRYptochromes that eventually suppress the CLOCK:BMAL1 complex inhibiting their own transcription[1]. This auto-regulatory loop is metabolically and post-transcriptionally regulated and in turn controls the expression of dozens of transcription factors and enzymes. In fact, it is estimated that 15% of hepatic transcriptome and plasma metabolome oscillates[2, 23]. Finally, indirect signals similarly contribute to rhythmic behavior including the timing of food intake, metabolism, and oscillations of body temperature from daily activity.

Transcriptional Control of Metabolism: Nuclear receptors are the largest group of transcription factors in humans, consisting of 48 different members. Their ligands include metabolites, vitamins, and hormones as well as xenobiotic[24]. Direct ligand binding triggers a conformational change in the receptor, allowing it to recruit co-regulators and initiate transcription[25]. Nuclear receptors play an essential role in metabolic homeostasis. Direct activation by metabolites, such as glucose, bile or fatty acids, allows cells to rapidly react to metabolic changes, by closing negative feedback loops[26]. For example, glucose absorbed during breakfast activates LXRα that induces fatty acid synthesis, depleting glucose from circulation. Hours later, fatty acids released during fasting will activate PPARα, blocking LXRα and inducing lipid peroxidation, thus priming the body for the next meal. Another regulatory loop involves FXR, SHP and LRH-1 leading to regulation of bile acid synthesis, uptake and secretion. Interestingly, out of 45 nuclear receptors expressed in mice, 25 were found to rhythmically cycle[27]. These include nuclear receptors directly regulated by the CLOCK:BMAL1 dimer like REV-ERBα and PPARα, as well as CAR, FXR, and SHP that play a critical role in drug and bile acid metabolism, respectively[27]. Importantly, the present inventor has already generated live GFP reporters for PPARα, FXR, CAR and REV-ERBα during the ERC starting grant offering the ability to track the cell autonomous rhythm in real-time.

Chrono-Pharmacology: Physiological rhythms have been known to affect drug distribution and clearance for over 30 years[4]. Driven by daily oscillations in drug transporters and CYP450 enzymes drugs such as acetaminophen, theophylline, and ampicillin show different pharmacokinetics in morning versus evening dosage[4]. In fact, acetaminophen also exhibits time-dependent toxicity in mice models due to the rhythmic expression of CYP2E1[28]. The molecular basis of this behavior is beginning to be understood and is thought to be driven in part by clock-regulated transcription factors such as PARbZip binding to D-box elements the promoters of CAR, CYP3A4 and MDR1. Bile acid production and excretion was similarly shown to oscillate due to the rhythmic expression of REV-ERBα and FXR, leading to diurnal patterns in ampicillin and flomoxef biliary clearance[4]. Interestingly, recent work showed the clock-independent cyclic accumulation of triglycerides in murine livers[14]. Together with daily oscillations in biliary secretion and oxidative state of liver cells it suggests a hereto-unknown time-dependent susceptibility to steatosis, cholestasis and apoptosis inducing drugs.

Pulsed Isotope Resolved Metabolomics: Mass-spectroscopy offers the ability to track the changing dynamic of metabolic fluxes using short (5-10 min) pulse of $^{13}C$-labeled metabolites[13]. The short time scale reduces the number of possible labeled metabolites to those produced along main pathways. Theoretically, changes in central carbon metabolism can be tracked by measuring patterns of $^{13}C$ integration in secreted citrate following treatment with a mixture of $^{13}C$-labeled glucose and glutamine.

Dynamic Metabolic and Transcriptional Regulatory Analysis

Based on published human plasma and mouse studies the present inventor expects albumin, ApoB100, lactate, and citrate to oscillate in the bioreactor outflow. Analysis of intracellular metabolites provides more complex data. Metabolites showing 24 hours rhythms are identified, and those with similar dynamics are clustered together using the JTK-cycle algorithm[23]. Using Cytoscape[45] oscillating metabolites are clustered based on network connectivity to identify pathways that oscillate together. A similar analysis on RNA-Seq data is carried out to identify GO/Kegg enrichment categories that similarly oscillate in phase. This analysis provides information on which metabolic pathway oscillates and suggests whether this oscillation is transcriptionally regulated.

Once metabolic pathways are identified, all the genes involved in this pathway are clustered into a metabolic category and an enrichment analysis is carried out to identify transcription factor regulating this oscillation. A transcription factor is considered to be regulating oscillation in a specific pathway, if its target genes are enriched with the oscillating genes in this pathway. Transcription factor target genes are defined using BioBase TRANSFAC based on expression analysis and binding data, supplemented with ENCODE. A similar analysis on naïve and infected hepatocytes showed excellent results (FIGS. 16A-F).

To validate this model the present inventor uses the GFP reporter library (FIG. 15) and measures changes in transcriptional activity in regulators identified computationally. In addition, nuclear receptor identified as circadian activated are blocked using small molecule inhibitors and loss of oscillation is validated on gene and metabolic flux levels (see FIGS. 16E-F). One advantage of the proposed in vitro system is that it is possible to both knock out CRY1/2 using CRISPR/Cas to assess the role of cell autonomous vs. central control of oscillations, and also decouple the activity of each factor (e.g. melatonin, cortisol) on the observed function.

Finally, in addition to the unbiased analysis CYP450 and drug transporter rhythms previously observed in HepG2 cells but not in mice are validated. Changing activity of CYP3A4 and CYP2D6 is evaluated by measuring production of 6ß-hydroxytestosterone and fluorescent AHMC in bioreactor outflow, respectively. (FIGS. 12G-H). Transporter activity is measured using CDFDA and CLF, fluorescent substrates of MRP2 and BSEP, using confocal microscopy or measuring fluorescence in the reactor outflow.

Example 7

Self-assembled organoids support long-term function of primary human hepatocytes: Primary human hepatocytes rapidly lose gene expression and metabolic function during standard culture (FIGS. 8A-C). One mechanism shown to support metabolic stabilization of hepatocytes is co-culture with non-parenchymal cells such as 3T3-J2 fibroblasts or endothelial cells restoring native heterotypic interactions[30, 31]. Over the past few years, the present inventor showed the rapid stabilization of primary human hepatocyte function in oxygenated co-cultures, and long-term stabilization of tri-cultures of hepatocytes, endothelial cells and pericytes in self-assembled organoids[7]. Organoids maintain high levels of albumin and urea secretion, and Cyp450 activity for over two months in vitro[7]. Over time, non-hepatic endothelial cells begin expressing liver sinusoid markers, such as L-SIGN, losing microvascular CD31 expression.

Non-specific absorption, bio-kinetics, and stable oscillations: In current practice, culture medium containing stimuli (i.e. drug, hormone, nutrient) is replaced in petri dishes every 24 hrs. However, non-specific absorption, cell uptake and clearance cause stimuli concentrations to rapidly decrease over time. Therefore, cell culture in vitro is subject to uncontrolled oscillations in stimuli (FIG. 9A). Microfluidics allows to control the cellular environment by constant perfusion. Under perfusion, absorption sites rapidly saturate and clearance reaches steady state, leading to constant stimulation (FIG. 9B). Once steady state is reached, flow can be mixed to create precisely controlled oscillations (FIG. 9C). The present inventor used this strategy to study drug clearance in microfluidic devices as well as the effects of insulin oscillations on liver cells.

Micro-well bioreactor supports long-term function of human organoids: The liver is highly vascularized, delivering oxygen at rates of 0.9 nmol/sec/$10^6$ cells[32], while protecting hepatocytes from shear[33, 34]. The gradient of oxygen and growth factors that develops along the sinusoid induces a demarcation of function, termed metabolic zonation. To mimic this environment the present inventor fabricated PDMS micro-well inserts using soft lithography (FIG. 4B). Inserts were covalently bonded to a glass coverslip using oxygen plasma, and housed in a CNC-machined 2" PMMA bioreactor that fits standard petri dish holders (FIGS. 4A, 10A). Primary human hepatocytes, microvascular endothelial cells and pericytes were mixed in ice-cold collagen gel and seeded in an open configuration. The small diameter of the micro-wells leads to rapid aggregation, creating liver organoids overnight (FIGS. 10B, 4B-C). Albumin and ApoB100 production were measured in bioreactor outflow, showing long-term stabilization of function and stable gene expression (FIGS. 10C, 4E). Numerical modeling (FIGS. 10D-E) showed physiological shear forces under 0.1 Pa inside the micro-wells for perfusion rates of 10 µl/min. The high flow rate results in equal oxygen distribution across the array. Oxygen consumption produces a gradient along the organoid mimicking the in vivo microenvironment (FIG. 10E).

Real-time focus independent measurement of oxygen uptake in microfluidic bioreactor: Oxygen uptake is a critical measurement of mitochondrial function and metabolic activity[35, 36]. However, electrochemical electrodes require frequent re-calibration, while optical sensors are affected by small changes in focus, cell migration and stage movement, making them unreliable for real time measurements of oxygen uptake. Therefore, the present inventor designed an optical system in which organoids are embedded with nanoprobes containing RuP dye and excited at 532 nm (FIGS. 11A-E). Oxygen is a quencher of RuP phosphorescence, leading to a decrease in decay time. Importantly, decay time is not sensitive to changes in probe concentration or excitation intensity (i.e. cell migration, mechanical movement). To measure in real-time, the present inventor used a novel two-frequency sinusoidal intensity-modulated light, allowing us to filter background interference while measuring phase shift in the emitted light. Measurements were taken every 15 minutes for 28 days (FIGS. 4A-E) with no phototoxicity, signal drift, or relevant loss of intensity.

Importantly, the real-time high sensitivity measurement of oxygen uptake uncovered a novel mechanism of acetaminophen toxicity. The present inventor showed that acetaminophen causes an immediate, reversible, dose-dependent loss of oxygen uptake followed by a slow, irreversible, dose-independent death (FIG. 11E). Importantly, the high sensitivity of the system allowed to detect a minute transient loss of mitochondrial respiration below the threshold of acetaminophen toxicity. The phenomenon was repeated in HeLa cells that lack CYP2E1 and 3A4, and localized to mitochondrial C3, suggesting a NAPQI-independent mechanism might be responsible for dermal and renal toxicity. These results mark the importance of tracking toxicity over time.

Induction of conditional proliferation in primary human hepatocytes: Primary human hepatocytes (PHH) are essential for the study of liver metabolism. However, scarcity and intermitted supply of freshly isolated cells limits scientific discovery. Cryopreserved hepatocytes are prohibitively expensive, as human hepatocytes fail to expand in vitro. The recent discovery of molecules capable of inducing few rounds of proliferation offers hope, but is far from robust[37]. Immortalized lines, like HepG2 or hTERT hepatocytes, rapidly de-differentiate losing gene expression and function. Recently, the present inventor utilized the E6/E7 expression system to conditionally release hepatocytes from Go (FIG. 12A). Muted E6/E7 expression is insufficient to induce proliferation, but causes an up-regulation of IL6ST/gp130, OSM liver regeneration receptor[38, 39]. Indeed, OSM stimulation caused Jak-STAT3 dependent proliferation, with 40 hrs doubling time (FIG. 12C). However, Jak-STAT3 activation caused epithelial-to-mesenchymal transition (EMT) and rapid loss of function. To block EMT the present inventor expanded cells in the presence of U0126 a MEK1/2 inhibitor, stabilizing epithelial morphology and cell polarization (FIGS. 12D-F). The present inventor generated cell banks from 5 different donors, reaching $10^{13}$ cells from each isolate. Importantly, upon removal of OSM, E6/E7 hepatocytes differentiate in 4 days and acquire mature phenotype. CYP450 activity profile of differentiated E6/E7 hepatocytes was not different from primary cells (p=0.44, n=5) and much higher than HepG2 cells (FIG. 11A-E). Testosterone metabolism by CYP3A4, an enzyme responsible for clearance of 35% of drugs on the market, and its induction by PXR-agonist rifampicin, remained high up to 42 population doublings (FIG. 12H). Finally, quantitative expression analysis showed strong nuclear receptor, enzymes, and transporter expression on population doubling 25 (FIG. 12I).

Importantly, serum shock induced oscillations in PER2 and CRY, suggesting that the cell-autonomous clock is functional.

Accurate detection of acute toxicity and toxicological end-points with proliferating hepatocytes: To critically evaluate the metabolic competence of the proliferating human hepatocytes (designated Upcyte® hepatocytes by Medicyte GmbH) the present inventor produced a list of 9 compounds known to induce steatosis, cholestasis and apoptosis in patients and 3 control compounds (Table 4). Acute toxicity was evaluated using Live/Dead staining after 24 hrs and is expressed as the concentration inducing 50% cell death, $TC_{50}$ (FIG. 13A). Remarkably, $TC_{50}$ values showed an $R^2$ correlation of 0.96 with primary hepatocytes, compared with 0.62 for HepG2 cells. Importantly, to demonstrate the appropriate toxicological end points, the present inventor carried out: CDFDA staining to show bile canaliculi disruption leading to bile acid accumulation (Cholestasis); Nile red and LipioTOX staining to quantify lipid accumulation (Steatosis); and TUNEL labeling to evaluate apoptosis (FIG. 13B). The proliferating hepatocytes showed accurate toxicological end points for all drugs, but could provide little dynamic information due to the destructive nature of the assay.

Pulsed isotope resolved metabolomics unravels metabolic switch controlling pluripotency: Recently, the present inventor showed that the metabolism of pluripotent stem cells changes during the first hours of differentiation[40], establishing a direct connection between inhibition of glycolysis and histone acetylation. Concomitantly, others showed a connection between glutaminolysis and methylation[41]. This dynamic between metabolic fluxes and chromatin could be mirrored during fasting-to-feeding transition (i.e. breakfast). A 15 min pulse of $^{13}$C-labeled glucose and glutamine was used to track glycolysis and glutaminolysis in cells using LC-MS/MS. A 3-fold down-regulation of glycolysis was shown supplanted by massive up-regulation of glutaminolysis (FIG. 14). Importantly, these changes in central carbon metabolism were clearly reflected in citrate $^{13}$C incorporation, suggesting the similar assessment could be carried out without destroying the cells (FIG. 14).

Transcriptional Activity Reporters:

Nuclear receptors are a family of ligand-activated transcription factors that play a critical role in the regulation of metabolic processes. Binding of hormones (i.e. cortisone) or metabolites (i.e. glucose) triggers a conformational change in the receptor, allowing it to recruit co-regulators and initiate transcription[25]. This means that while the activity of some nuclear receptors might be circadian, their mRNA levels or chromatin binding patterns may stay unchanged. This might explain why mRNA levels of HNF4α and PXR did not oscillate although their ligands and target genes appear to be rhythmically modulated. To address this issue the present inventor developed a GFP-reporter library by cloning multiple repeats of DNA response elements upstream of a minCMV promoter. Transcription factor activation transcribes destabilized copGFP, with super-fast maturation (1.5 hrs) and short half-life (2 hrs), directly measuring transcriptional activity (FIG. 15). Reporters to NFκB, STAT3, SREBP2, C/EBP, LXR, PXR, CAR, FXR, PPARα, PPARγ, AP-1, and ISRE (STAT1) were generated and validated by the present inventor. This library is used to elucidate metabolic regulatory mechanism serving as a critical tool for drug discovery.

Transcriptional-Metabolic Characterization of HCV Infection: Chronic HCV infection is associated with the development of fatty liver disease and type-2 diabetes.

Recently, a model of primary human hepatocytes that permits the coupling of system-level measurement of metabolic fluxes with regulatory analysis under steady state conditions was established. The present inventor's analysis uncovered HCV-induced activation of HNF4α, PPARα, PXR, and FXR that leads to induction of glycolysis, fatty acid oxidation (FIGS. 16A-F), drug metabolism, and inhibition of cholesterol biosynthesis, respectively. Pharmaceutical inhibition of each receptor reversed the corresponding metabolic change. Importantly, HCV-infected primary human hepatocytes become dependent on glycolysis resembling the Warburg effect described in proliferating cancer and stem cells. Inhibition of HNF4α not only reverses glycolysis, but also increases apoptosis and blocks viral replication in HCV-infected cells.

Taken together, the present inventor engineered a liver-on-chip platform supporting real-time measurements of metabolic changes induce by physiological rhythms, by adapting a liver-on-chip (FIGS. 10A-11E) to support physiological rhythm by oscillating temperature and hormones. The dynamics of transcriptional and metabolic changes using end-point assays are characterized. The device has been integrated to MS/MS to dynamically measure metabolites in the bioreactor outflow (FIG. 14). Metabolic fluxes are tracked using SIRM. FTIR or SERS are developed to non-invasively monitor the metabolic state of the cells. The system is validated by tracking the dynamics of drug toxicity (FIGS. 13A-B). Finally, the Chip-MS and FTIR/SERS are integrated to permit tracking of fast and slow processes during a single nutritional event.

Integrate infrared (IR)-microspectroscopy for real-time monitoring of metabolic state Approach: Infrared spectroscopy permits a non-invasive metabolic fingerprint analysis of living cells, allowing to monitor dynamic changes in lipid or bile accumulation due to physiological rhythms or drug induced toxicity (FIGS. 12A-J). FTIR Spectrometer is connected to an automated Olympus IX83 with an MCT detector connected in transmission (FTIR) or reflection (ATR or SERS) modes. Drug-induced steatosis and cholestasis is evaluated with: (1) FTIR transmission through thin $CaF_2$ or silicon-surfaced bioreactors, (2) Attenuated total reflection (ATR) mode with high NA objective into Ge-surfaced bioreactor, and (3) Surface-enhanced Raman scattering (SERS) in quartz-surfaced bioreactors. Imaging modality is selected based on S/N ratio and ease of use. IR-microspectroscopy is used to track the metabolic dynamics of liver cells through the day/night cycle, critically comparing these findings to recent murine studies[2, 14]. Importantly, the dynamics of toxicological end-points using 11 known compounds is tracked (FIGS. 13A-B) attempting to detect alterations in metabolism below the threshold of toxicity.

Comparing FTIR, ATR-FTIR, and SERS for the Evaluation of Lipid and Bile Accumulation FTIR microspectroscopy is an established methodology, recently reviewed in Nature Protocols[43] that provides clear spectra of molecular vibrations. Liver cells, especially, produce a classical fingerprint region in which glycogen (1180-950 $cm^{-1}$) and lipid signatures (1740-1710 $cm^{-1}$) are clear. However, water absorption can significantly attenuate the signal necessitating work on dried samples. In addition, dense samples such as FFPE tissues are cut to 8-12 μm thickness to permit transmission. Finally, glass mid-IR absorption requires transmission windows to be fabricated from $CaF_2$ or silicon. Thin $CaF_2$ windows are fabricated for the bioreactor (FIGS. 10A-E) and limit the optical path to 80 μm, trapping organoids between the windows while perfusing around them. Silicon is used in FTIR multiwell plates (e.g. Bruker, Pike) and could provide a simpler alternative to $CaF_2$. As organoids are less dense than tissue and water is not in the optical path it is possible to collect transmission signals using an HgCdTe (MCT) detector.

Another alternative is to use an ATR crystal like a germanium or diamond for the reactor bottom surface. Using a 0.6 NA infrared objective it is possible to bounce a signal and collect the ATR signal through the same objective. In this case, only the first 1-2 μm of the sample is probed, making sample thickness and water volume immaterial.

Finally, surface-enhanced Raman scattering (SERS), recently reviewed in Nature Protocols[48], probes inelastic scattering using metallic nanostructures to enhance the signal. SERS can amplify the traditionally weak Raman signature by several orders-of-magnitude. In contrast to FTIR, water gives a very weak Raman signature and a simple quartz surface shows little to no absorption at the 500-3000 $cm^{-1}$ region. This simplifies the integration of Raman with the bioreactor and standard microscopy. 50 nm diameter gold nanoparticles are dispersed in the organoids on seeding. Gold nanoparticles show no toxicity in living cells, but show strong photoluminescence at 550 nm. Therefore, a 680 nm laser is used where autofluorescence and photo damage are minimal, while the Raman signature is still strong.

Liver organoids are treated for 48 hrs with amiodarone, an antiarrhythmic agent, known to induce steatosis and phospholipidosis, or chlorpromazine, a dopamine antagonist, known to induce cholestasis. Hepatocyte accumulation of lipids or bile acids are quantified using LipidTOX and CDFDA (FIGS. 13A-B). Perfusate medium is switched to PBS buffer with $Ca^{2+}$ and $Mg^{2+}$ for the scanning period. Spectra is acquired using all 3 methods, processed using commercially available software, and assessed for the presence of fatty acids, bile acids, and glycogen. Imaging modality is selected based on S/N ratio, and the simplicity of set up and bioreactor fabrication/cost (i.e. SERS>Transmission>ATR-FTIR).

Utilize pSIRM to Detect Changes in Intracellular Fluxes

Pulsed SIRM offers insight into minute changes in intracellular metabolic fluxes (FIGS. 7-14). SIRM is used as an end-point assay to confirm results using $^{13}C$-labeled glucose, glutamine or palmitate. However, $^{13}C$-labeled products, like citrate, can also be measured in bioreactor outflow, providing dynamic non-invasive information on intracellular fluxes.

The liver is classically a sink for citrate that, like lactate, is primary produced by muscle activity. Indeed citrate and lactate were shown to oscillate together in plasma[47]. However, significant parts of the liver do produce or recycle lactate and citrate under certain conditions. Therefore, citrate can potentially be found in the perfusate. Mixtures of 25 mM glucose and 4 mM glutamine $^{13}C$ are introduced for 15 to 30 min and citrate is assessed in perfusate as previously described (FIGS. 7-14). This quantification provides a rapid non-invasive snapshot of intracellular pathways that could be measured continuously with minute resolution.

Run Real-Time IR-Spectroscopy Fingerprinting on Physiologically Oscillating Liver-On-Chip Recent work showed a rhythmic accumulation of lipids in the mouse liver[14] and a similar circadian behaviour for bile production. Surprisingly, CLOCK-deficient mice showed similar day/night rhythm, albeit at a different sequence, suggesting that endocrine, nutritional and behavioural cycles play a role in regulating this transient metabolic state. The present inventor uses IR-spectroscopy to track this metabolic signature in real time. Wild type and CRY1/2 knockout hepatocytes are perfused with (1) all hormones and factors (FIGS. 17A-B), or with time-average concentrations of (2) melatonin, (3) cortisol, (4) $T_3$, (5) growth hormone, and (6) average temperature. Signature is analysed by IR-spectroscopy every 30 min for 24 hours. IR-spectra is critically compared to intracellular metabolites quantified by LC-MS/MS, as well as specific quantification of triglycerides and bile acids using commercially available kits (FIGS. 16A-F). Interestingly, recently the present inventor showed that melatonin could induce lipid accumulation in human hepatocytes. Without being bound by any theory the present inventor has hypothesized that melatonin plays a role in the transient accumulation of lipids in the liver, suggesting that without melatonin Clock-deficient hepatocytes won't show transient triglyceride accumulation. Mechanism is evaluated by systematically perturbing regulators whose activity changed prior to steatosis.

tracked closely using oxygen and IR-spectroscopy every hour. The 24 spectra is segmented by time and principle component analysis is used to identify drugs that change the normal metabolic fingerprint at each time point. The present inventor specifically focuses on the rate of lipid and bile acid accumulation and release and whether it is affected by drug therapy.

Elucidation of the effect fasting-to-feeding transition on circadian rhythm Night shift workers forced to eat at night show an increased risk for diabetes and obesity. Glucose and insulin rich stimuli are provided mimicking breakfast during morning and evening and track changes in oxygen consumption, lipid and glycogen accumulation (IR-spectroscopy) and metabolism (Chip-MS). Cell samples are collected during the transition using ice-cold solvent to flash fix the cells for proteome and phosphoproteome analysis. In addition, the SIRM is used 10 min before and after the transition to track

TABLE 4

Establishment of the relationship between drug-induced toxicity and physiological cycles

| Compound | Sigma-Aldrich ® Catalogue number | Classification | Activation | Toxicity |
|---|---|---|---|---|
| Cyclosporine A | C3662 | Immunosuppressant | Yes | Cholestasis |
| Chlorpromazine | C8138 | Antipsychotic | No | Cholestasis |
| Troglitazone | T2573 | Anti-diabetic | Yes | Cholestasis |
| Valproate | P4543 | Anticonvulsant | Yes | Steatosis |
| Aspirin | A5376 | Analgesic | No | Steatosis |
| Amiodarone | A8423 | Antiarrhythmic | No | Steatosis |
| Diclofenac | D6899 | Analgesic | Yes | Apoptosis |
| Acetaminophen | A7085 | Analgesic | Yes | Apoptosis |
| Aflatoxin B1 | A6636 | Toxin | Yes | Apoptosis |
| Mannitol | M4125 | Flavoring | n.a. | Control |
| Menthol | M2772 | Flavoring | n.a. | Control |

Table 4. Liver-specific Gold compound list develop in SEURAT-1 and critically evaluated ir static hepatocyte cultures for acute toxicity (FIGS. 12A-J).

Drug-induced liver toxicity is currently evaluated using end-point assays following a 24-hour exposure in static conditions. Transient effects below the threshold of toxicity (FIG. 11E) are regularly missed, leading to poor assessment of clinical toxicity and post-market withdrawals with disastrous financial and clinical consequences. In fact, it is currently impossible to assess whether a drug will accelerate hepatic lipid accumulation precisely at the cycle height, or block the critical release of bile acids before the morning meal.

Here model is used to track the chrono-toxicity of a well-characterize compound library (Table 4) developed for SEURAT-1 cluster. $TC_{50}$ values were already determined in Upcyte hepatocytes cultured under static condition (FIGS. 12A-J). First the cells are exposed in the bioreactor, cultured under constant conditions, to increasing concentrations of each drug, collecting oxygen uptake data and IR-spectra for 24 hours. Oxygen consumption is monitored for changes in respiration. The IR-spectra of each drug is used and a principle component analysis is run attempting to discover populations in which metabolism shifted from the normal. Based on the results (FIG. 14) the effects on cellular metabolism (e.g. glycogen depletion) are determined and a sub-threshold metabolic shift is identified.

The lowest drug concentration that produces a metabolic effect is exposed to physiologically oscillating organoids. Drugs are dosed in the 'morning' cycle and its clearance are quantified by perfusate Chip-MS. Metabolic cycles are changes in glycolysis and glutaminolysis using $^{13}$C-labeled substrates. Without being bound by any theory, it is expected that insulin phosphorylation pattern would be superimposed on a different proteome landscape, creating a different metabolic program yet to be described.

Following the Hepatic Insulin Response Through the Day/Night

Glycemic meal is composed of 75 mM glucose and 60 µU/ml insulin introduced over 20 minutes at either 08:00 or 20:00 equivalent of the day/night cycle. Bioreactor without meal serves as negative control. The present inventor tracks changes in oxygen consumption, lipid and glycogen accumulation (IR-spectroscopy) and metabolism (Chip-MS) through 24 hours. Oxygen consumption and IR-spectroscopy are measured every 5 minutes for the first 2 hours and every 30 minutes thereafter for 24 hrs. Chip-MS, used for targeted analysis and unlimited by chromatography are similarly used every 5 minutes. The present inventor is looking at (1) short and long-term differences in metabolic rhythms due to a meal (e.g. entrainment), and (2) differences between the day and night patterns of metabolic changes.

If changes in glucose, lactate, or glutamine are observed in the bioreactor perfusate $^{13}$C-labeled glutamine and glucose are pulsed for pSIRM analysis. SIRM analysis is used 15 minutes before, during and after the meal to measure rapid changes in central carbon metabolism. Finally, cell samples are collected during the transition using ice-cold solvent to flash fix the cells for proteome and phosphoproteome analysis. Samples are stored at −80° C. and split for a unbiased metabolome analysis using LC-MS/MS (AB Sciex QTRAP 5500 @ Core Facility), and tandem LC-MS shotgun proteome analysis combined with SILAC to be carried out at Prof. Stefan Kempa's laboratory (MDC, Berlin).

Computational Model Day and Night Feeding Transitions

The present inventor has modeled the metabolism of primary human hepatocytes (FIGS. 16A-F) under steady state conditions, the derivation of metabolic flux analysis (MFA) under non-stable conditions is a massive computational and experimental challenge, recently reviewed by Wiechert and Noh[49]. The in vitro analysis provides the critical variables needed, including: (1) quantitative measurements of both intracellular and secreted metabolites, including oxygen uptake; (2) three time points for each event; (3) specific focus on central carbon metabolism limiting the network examined, and (4) a readily available computer cluster. Therefore, based on Wiechert and Noh's original formulation and the recently published MATLAB-based INCA model ENREF 48[50] the isotopically nonstationary MFA (INST-MFA) is solved. The enzymatic activity is found and correlated to protein phosphorylation providing unparalleled understanding of metabolic shifts and how they are influenced by slow regulatory changes.

Example 8

E6/E7$^{low}$ Upcyte™ hepatocytes line 422, from a male Hispanic donor, and line 653, from a female Caucasian old donor, were seeded in OSM-free differentiation media as previously described (Levy et al. *Nature Biotechnology* 2015). Following 5 days of differentiation, cells were synchronized in corticosteroid-free culture medium for 24 hours, followed by high 100 μM Dexamethasone dose (day medium), entraining a circadian cycle. Triplicate cell-lysate and media samples were collected every 4 hours in the following 2 days. RNA was extracted from lysate samples, using NucleoSpin® RNA (Qiagen, Valencia, Calif.) according to manufacturer's direction. RNA were further reverse-transcribed to increase stability of the molecules and tagmented with in-house produced primers containing unique-per-molecule tags along with unique-per-sample tag, using an in-house developed TN5 enzyme. Samples were pooled together into a single library and further processed for next generation sequencing by the Hebrew University Center for Genomic Technologies. Library construction was conducted using Illumina TruSeq RNA Library Prep V2 Kit (Illumina, San Diego, Calif.) according to manufacturer's protocol and sequenced on Illumina NextSeq500 with single-end, 86 bp reads using the High Output V2 Kit. Sequencing reads were filtered to unique reads only and mapped to the UCSC human transcriptome (genome build hg38) using Bowtie 2. Expression levels of all genes were quantified using bed-tools. Gene accessions were converted to gene symbols using DAVID, and later used to collapse transcript variants under the same gene symbol using an in-house program. For further analysis of circadian expression patterns, the expression matrix was submitted to the R package JTK_CYCLE, and filleted for genes exhibiting an oscillatory expression with 24±4 hours period. E6/E7$^{low}$ 653 hepatocytes showed 41 genes with circadian expression pattern, while E6/E7$^{low}$ 422 hepatocytes showed 267 genes with circadian expression pattern, adjusted p-values less than 0.005. FIGS. 23A-H show gene expression levels, as counts, for several circadian and metabolic regulators, error bars represent the SEM.

Example 9

HepG2/C3A cells and CPOx-50-RuP beads (Colibri Photonics, Germany) were suspended in rat tail collagen at a density of 7×10$^5$ cells per μl. A volume of 1.1 μl of the suspension-gel was injected into each microwell and left to form organoid spontaneously until metabolic activity stabilized around day 5. Real-time oxygen measurements were performed optically using on-chip lifetime-based luminescence quenching (LBLQ) as previously described (Bavli et al. PNAS 2016). Bioreactor outflow was connected to 4 analyte sensors purchased from Innovative Sensor Technology (IST, Switzerland). Glucose, lactate, and glutamine measurements were made continuously during the entire experiment. FIG. 24 shows the circadian metabolic rhythms produces by exposing the HepG2/C3A cells to day medium and temperature oscillation.

Although the invention has been described in conjunction with specific embodiments thereof, it is evident that many alternatives, modifications and variations are apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

1. Bell-Pedersen, D., et al., *Circadian rhythms from multiple oscillators: lessons from diverse organisms*. Nat Rev Genet, 2005. 6(7): p. 544-56.
2. Bass, J. and J. S. Takahashi, *Circadian integration of metabolism and energetics*. Science, 2010. 330(6009): p. 1349-54.
3. Skene, D. J. and J. Arendt, *Human circadian rhythms: physiological and therapeutic relevance of light and melatonin*. Ann Clin Biochem, 2006. 43(Pt 5): p. 344-53.
4. Adamovich, Y., et al., *Rhythmic Oxygen Levels Reset Circadian Clocks through HIF1alpha*. Cell Metab, 2017. 25(1): p. 93-101.
5. Balsalobre, A., F. Damiola, and U. Schibler, *A serum shock induces circadian gene expression in mammalian tissue culture cells*. Cell, 1998. 93(6): p. 929-37.
6. Mistlberger, R. E., *Food-anticipatory circadian rhythms: concepts and methods*. Eur J Neurosci, 2009. 30(9): p. 1718-29.
7. Johnston, J. D., *Physiological responses to food intake throughout the day*. Nutr Res Rev, 2014. 27(1): p. 107-18.

8. Bollinger, T. and U. Schibler, *Circadian rhythms—from genes to physiology and disease.* Swiss Med Wkly, 2014. 144: p. w13984.
9. Green, C. B., J. S. Takahashi, and J. Bass, *The meter of metabolism.* Cell, 2008. 134(5): p. 728-42.
10. Robles, M. S., J. Cox, and M. Mann, *In-vivo quantitative proteomics reveals a key contribution of post-transcriptional mechanisms to the circadian regulation of liver metabolism.* PLoS Genet, 2014. 10(1): p. e1004047.
11. Reddy, A. B., et al., *Circadian orchestration of the hepatic proteome.* Curr Biol, 2006. 16(11): p. 1107-15.
12. Eckel-Mahan, K. L., et al., *Coordination of the transcriptome and metabolome by the circadian clock.* Proc Natl Acad Sci USA, 2012. 109(14): p. 5541-6.
13. Maury, E., K. M. Ramsey, and J. Bass, *Circadian rhythms and metabolic syndrome: from experimental genetics to human disease.* Circ Res, 2010. 106(3): p. 447-62.
14. Koren, D., K. L. O'Sullivan, and B. Mokhlesi, *Metabolic and glycemic sequelae of sleep disturbances in children and adults.* Curr Diab Rep, 2015. 15(1): p. 562.
15. Laermans, J. and I. Depoortere, *Chronobesity: role of the circadian system in the obesity epidemic.* Obes Rev, 2016. 17(2): p. 108-25.
16. Eckel-Mahan, K. L., et al., *Reprogramming of the circadian clock by nutritional challenge.* Cell, 2013. 155(7): p. 1464-78.
17. Udoh, U.S., et al., *Chronic ethanol consumption disrupts diurnal rhythms of hepatic glycogen metabolism in mice.* Am J Physiol Gastrointest Liver Physiol, 2015. 308(11): p. G964-74.
18. Zhou, P., et al., *Dissociation between diurnal cycles in locomotor activity, feeding behavior and hepatic PERIOD2 expression in chronic alcohol-fed mice.* Alcohol, 2015. 49(4): p. 399-408.
19. Paschos, G. K., et al., *Obesity in mice with adipocyte-specific deletion of clock component Arntl.* Nat Med, 2012. 18(12): p. 1768-77.
20. Marcheva, B., et al., *Disruption of the clock components CLOCK and BMAL1 leads to hypoinsulinaemia and diabetes.* Nature, 2010. 466(7306): p. 627-31.
21. Tao, H., et al., *Inhibition of expression of the circadian clock gene Period causes metabolic abnormalities including repression of glycometabolism in Bombyx mori cells.* Sci Rep, 2017. 7: p. 46258.
22. Englund, A., et al., *NPAS2 and PER2 are linked to risk factors of the metabolic syndrome.* J Circadian Rhythms, 2009. 7: p. 5.
23. Dupuis, J., et al., *New genetic loci implicated in fasting glucose homeostasis and their impact on type 2 diabetes risk.* Nat Genet, 2010. 42(2): p. 105-16.
24. Dashti, H. S., et al., *CRY1 circadian gene variant interacts with carbohydrate intake for insulin resistance in two independent populations: Mediterranean and North American.* Chronobiol Int, 2014. 31(5): p. 660-7.
25. Sookoian, S., et al., *Genetic variants of Clock transcription factor are associated with individual susceptibility to obesity.* Am J Clin Nutr, 2008. 87(6): p. 1606-15.
26. Alberti, K. G., P. Zimmet, and J. Shaw, *Metabolic syndrome—a new world-wide definition. A Consensus Statement from the International Diabetes Federation.* Diabet Med, 2006. 23(5): p. 469-80.
27. Boudreau, D. M., et al., *Health care utilization and costs by metabolic syndrome risk factors.* Metab Syndr Relat Disord, 2009. 7(4): p. 305-14.
28. Rutter, J., et al., *Regulation of clock and NPAS2 DNA binding by the redox state of NAD cofactors.* Science, 2001. 293(5529): p. 510-4.
29. Ramsey, K. M., et al., *Circadian clock feedback cycle through NAMPT-mediated NAD+ biosynthesis.* Science, 2009. 324(5927): p. 651-4.
30. Peek, C. B., et al., *Circadian clock NAD+ cycle drives mitochondrial oxidative metabolism in mice.* Science, 2013. 342(6158): p. 1243417.
31. O'Neill, J. S., et al., *cAMP-dependent signaling as a core component of the mammalian circadian pacemaker.* Science, 2008. 320(5878): p. 949-53.
32. Dibner, C. and U. Schibler, *Circadian timing of metabolism in animal models and humans.* J Intern Med, 2015. 277(5): p. 513-27.
33. Zhang, E. E., et al., *Cryptochrome mediates circadian regulation of cAMP signaling and hepatic gluconeogenesis.* Nat Med, 2010. 16(10): p. 1152-6.
34. Lemmer, B., *Clinical chronopharmacology: the importance of time in drug treatment.* Ciba Found Symp, 1995. 183: p. 235-47; discussion 247-53.
35. Mauvoisin, D., et al., *Circadian clock-dependent and -independent rhythmic proteomes implement distinct diurnal functions in mouse liver.* Proc Natl Acad Sci USA, 2014. 111(1): p. 167-72.
36. Doherty, C. J. and S. A. Kay, *Circadian surprise—it's not all about transcription.* Science, 2012. 338(6105): p. 338-40.
37. Johnston, J. D., *Physiological links between circadian rhythms, metabolism and nutrition.* Exp Physiol, 2014. 99(9): p. 1133-7.
38. Ley, R. E., et al., *Obesity alters gut microbial ecology.* Proc Natl Acad Sci USA, 2005. 102(31): p. 11070-5.
39. Swanson, K. S., et al., *Phylogenetic and gene-centric metagenomics of the canine intestinal microbiome reveals similarities with humans and mice.* ISME J, 2011. 5(4): p. 639-49.
40. Brown, R. P., et al., *Physiological parameter values for physiologically based pharmacokinetic models.* Toxicol Ind Health, 1997. 13(4): p. 407-84.
41. Chandrasekera, P. C. and J. J. Pippin, *Of rodents and men: species-specific glucose regulation and type 2 diabetes research.* ALTEX, 2014. 31(2): p. 157-76.
42. Rangarajan, A. and R. A. Weinberg, *Opinion: Comparative biology of mouse versus human cells: modelling human cancer in mice.* Nat Rev Cancer, 2003. 3(12): p. 952-9.
43. SABOLIĆ, I., BRELJAK, D., LJUBOJEVIĆ, M., BRZICA, H., *Are mice, rats, and rabbits good models for physiological, pharmacological and toxicological studies in humans?* PERIODICUM BIOLOGORUM, 2011. 113(1): p. 7-16.
44. Rao, S. and A. S. Verkman, *Analysis of organ physiology in transgenic mice.* Am J Physiol Cell Physiol, 2000. 279(1): p. C1-18.
45. Nyberg, S. L., et al., *Primary hepatocytes outperform Hep G2 cells as the source of biotransformation functions in a bioartificial liver.* Ann Surg, 1994. 220(1): p. 59-67.
46. Marx, U., et al., *'Human-on-a-chip' developments: a translational cutting-edge alternative to systemic safety assessment and efficiency evaluation of substances in laboratory animals and man?* Altern Lab Anim, 2012. 40(5): p. 235-57.
47. Levy, G., et al., *Long-term culture and expansion of primary human hepatocytes.* Nat Biotechnol, 2015. 33(12): p. 1264-1271.

48. Gamble, K. L., et al., *Circadian clock control of endocrine factors.* Nat Rev Endocrinol, 2014. 10(8): p. 466-75.
49. Redwine, L., et al., *Effects of sleep and sleep deprivation on interleukin-6, growth hormone, cortisol, and melatonin levels in humans.* J Clin Endocrinol Metab, 2000. 85(10): p. 3597-603.
50. Bavli, D., et al., *Real-time monitoring of metabolic function in liver-on-chip microdevices tracks the dynamics of mitochondrial dysfunction.* Proc Natl Acad Sci USA, 2016. 113(16): p. E2231-40.
51. Ware, B. R. and S. R. Khetani, *Engineered Liver Platforms for Different Phases of Drug Development.* Trends Biotechnol, 2017. 35(2): p. 172-183.
52. Kidambi, S., et al., *Oxygen-mediated enhancement of primary hepatocyte metabolism, functional polarization, gene expression, and drug clearance.* Proc Natl Acad Sci USA, 2009. 106(37): p. 15714-9.
53. Nahmias, Y., F. Berthiaume, and M. L. Yarmush, *Integration of technologies for hepatic tissue engineering.* Adv Biochem Eng Biotechnol, 2007. 103: p. 309-29.
54. Wilkening, S., F. Stahl, and A. Bader, *Comparison of primary human hepatocytes and hepatoma cell line Hepg2 with regard to their biotransformation properties.* Drug Metab Dispos, 2003. 31(8): p. 1035-42.
55. Levy, G., et al., *Nuclear receptors control pro-viral and antiviral metabolic responses to hepatitis C virus infection.* Nat Chem Biol, 2016. 12(12): p. 1037-1045.
56. Conesa, A., et al., *A survey of best practices for RNA-seq data analysis.* Genome Biol, 2016. 17: p. 13.
57. Aviram, R., et al., *Lipidomics Analyses Reveal Temporal and Spatial Lipid Organization and Uncover Daily Oscillations in Intracellular Organelles.* Mol Cell, 2016. 62(4): p. 636-48.
58. Koike, N., et al., *Transcriptional architecture and chromatin landscape of the core circadian clock in mammals.* Science, 2012. 338(6105): p. 349-54.
59. Dyar, K. A. and K. L. Eckel-Mahan, *Circadian Metabolomics in Time and Space.* Front Neurosci, 2017. 11: p. 369.
60. Cong, L. and F. Zhang, *Genome engineering using CRISPR-Cas9 system.* Methods Mol Biol, 2015. 1239: p. 197-217.
61. Yang, X., et al., *Nuclear receptor expression links the circadian clock to metabolism.* Cell, 2006. 126(4): p. 801-10.
62. Wu, H., et al., *High-throughput tissue extraction protocol for NMR-and MS-based metabolomics.* Anal Biochem, 2008. 372(2): p. 204-12.
63. Pietzke, M. and S. Kempa, *Pulsed stable isotope-resolved metabolomic studies of cancer cells.* Methods Enzymol, 2014. 543: p. 179-98.
64. Russell, W., et al., *Free triiodothyronine has a distinct circadian rhythm that is delayed but parallels thyrotropin levels.* J Clin Endocrinol Metab, 2008. 93(6): p. 2300-6.
65. Balsalobre, A., et al., *Resetting of circadian time in peripheral tissues by glucocorticoid signaling.* Science, 2000. 289(5488): p. 2344-7.
66. Gronfier, C. and G. Brandenberger, *Ultradian rhythms in pituitary and adrenal hormones: their relations to sleep.* Sleep Med Rev, 1998. 2(1): p. 17-29.

---

What is claimed is:

1. An in-vitro method of sustaining a synchronized circadian rhythm in mammalian cells a in cell culture, the method comprising:
   exposing the mammalian cells to a continuous flow of medium with a constant total volumetric flow rate in which at least two hormones are present in an oscillating manner with a periodicity of 24±4 hours,
   wherein a first hormone and a second hormone of said at least two hormones are distinct,
   wherein said exposing comprises flowing over said mammalian cells in culture a first medium comprising said first hormone, a second medium comprising said second hormone, a third medium devoid of said first hormone and said second hormone or a combination of said media and wherein changing concentrations of said at least two hormones are exposed to said mammalian cells by varying a volumetric flow rate of each of said media while keeping a constant total volumetric flow rate over the cells,
   wherein an interval between a maximum concentration of said first hormone exposed to said mammalian cells and a maximum concentration of said second hormone exposed to said mammalian cells is at least 2 hours,
   and wherein said first hormone is selected from the group consisting of: cortisol, testosterone, adiponectin, insulin, thyroxine (T4), and fibroblast growth factor 21 (FGF21), and said second hormone is selected from the group consisting of: melatonin, growth hormone, Triiodothyronine (T3), ghrelin, prolactin, TSH, vasopressin, and leptin, thereby sustaining a synchronized circadian rhythm in mammalian cells in a cell culture.

2. The in-vitro method of claim 1, wherein said continuous flow of medium at a constant total volumetric flow rate produces a constant shear force on said mammalian cells.

3. The in-vitro method of claim 1, wherein said interval is no more than about 6 hours.

4. The in-vitro method of claim 1, wherein duration of said maximum concentration of said first hormone exposed to said mammalian cells is at least 30 minutes and no more than about 24 hours.

5. The in-vitro method of claim 1, wherein duration of said maximum concentration of said second hormone exposed to said mammalian cells is at least 10 seconds and no more than about 6 hours.

6. The in-vitro method of claim 1, wherein said first hormone is cortisol.

7. The in-vitro method of claim 1, wherein said second hormone is melatonin.

8. The in-vitro method of claim 1, wherein said mammalian cells are characterized by a synchronized metabolic activity no later than within 72 hours after being exposed to said at least two hormones.

9. The in-vitro method of claim 1, wherein said mammalian cells are comprised in an organoid.

10. The in-vitro method of claim 9, wherein said organoid comprises hepatic cells and endothelial cells.

11. The in-vitro method of claim 10, wherein said organoid further comprises fibroblasts.

12. The in-vitro method of claim 9, wherein said organoid comprises enterocytes.

13. The in-vitro method of claim 12, wherein said organoid further comprises endothelial cells.

14. The in-vitro method of claim 9, wherein said organoid comprises cardiomyocytes and endothelial cells.

15. The in-vitro method of claim 14, wherein said cardiomyocytes are obtainable by differentiation of induced pluripotent stem cells.

16. The in-vitro method of claim 9, wherein said organoid comprises neural progenitor cells and endothelial cells.

17. The in-vitro method of claim 16, wherein said neural progenitor cells are obtainable by differentiation of induced pluripotent stem cells.

18. The in-vitro method of claim 9, wherein said organoid comprises renal cells.

19. The in-vitro method of claim 1, wherein each maximum concentration of said first hormone or maximum concentration of said second hormone occurs once during said 24±4 hours.

20. The in-vitro method of claim 1, wherein said first hormone is cortisol and said second hormone is melatonin.

21. The in vitro method of claim 1, wherein said first medium comprises a constant concentration of said first hormone and said second medium comprises a constant concentration of said second hormone.

22. The in vitro method of claim 1, wherein said mammalian cells are adherent cells.

23. The in vitro method of claim 22, wherein said exposing comprises:
 a. flowing over said adherent cells in culture at least said first medium and said third medium;
 b. decreasing the volumetric flow rate of said first medium while simultaneously increasing the volumetric flow rate of said third medium, said second medium or both so as to maintain a constant total volumetric flow rate;
 c. flowing over said adherent cells at least said second medium and said third medium;
 d. increasing the volumetric flow rate of said second medium while simultaneously decreasing the volumetric flow rate of said first medium, said third medium or both so as to maintain a constant total volumetric flow rate;
 e. decreasing the volumetric flow rate of said second medium while simultaneously increasing the volumetric flow rate of said third medium, said first medium or both so as to maintain a constant total volumetric flow rate; and
 f. repeating steps a-e with a periodicity of 24±4 hours.

* * * * *